US009597117B2

(12) United States Patent
Sanders et al.

(10) Patent No.: US 9,597,117 B2
(45) Date of Patent: Mar. 21, 2017

(54) CLAMPING DEVICE FOR USE WITH AN ANATOMIC EXTERNAL FIXATION SYSTEM

(71) Applicant: FOOT INNOVATIONS, LLC, Tampa, FL (US)

(72) Inventors: Roy W. Sanders, Tampa, FL (US); Sergio Gutierrez, Tampa, FL (US)

(73) Assignee: FOOT INNOVATIONS, LLC, Tampa, FL (US)

( * ) Notice: Subject to any disclaimer, the term of this patent is extended or adjusted under 35 U.S.C. 154(b) by 0 days.

(21) Appl. No.: 14/871,618

(22) Filed: Sep. 30, 2015

(65) Prior Publication Data

US 2016/0095624 A1    Apr. 7, 2016

Related U.S. Application Data

(60) Provisional application No. 62/058,262, filed on Oct. 1, 2014.

(51) Int. Cl.
A61B 17/00 (2006.01)
A61B 17/64 (2006.01)
A61B 17/60 (2006.01)

(52) U.S. Cl.
CPC .......... A61B 17/6416 (2013.01); A61B 17/60 (2013.01); A61B 17/645 (2013.01);
(Continued)

(58) Field of Classification Search
CPC ..... A61B 17/62; A61B 17/66; A61B 17/6466; A61B 17/6416; A61B 17/645;
(Continued)

(56) References Cited

U.S. PATENT DOCUMENTS 2,346,346 A    4/1944 Anderson
4,433,677 A    2/1984 Ulrich et al.
(Continued)

FOREIGN PATENT DOCUMENTS

DE    29916855 U1    1/2000

OTHER PUBLICATIONS

International Search Report for PCT/US2015/053316 mailed Apr. 8, 2016.
(Continued)

Primary Examiner — Mary Hoffman
Assistant Examiner — Tara R Carter
(74) Attorney, Agent, or Firm — Foley & Lardner LLP; Christopher J. McKenna; Shabbi S. Khan

(57) ABSTRACT

A clamping device for an external fixation system includes a clamp body and a locking assembly. The clamp body includes a first and second jaw that define a slot in communication with a first channel. The first channel can accommodate a first fixation element along a longitudinal axis of the first channel. The first jaw defines a first opening and the second jaw defines a second opening that are sized to receive a portion of the locking assembly. The locking assembly includes a first fastening element to pass through the first and second openings, and define a second channel to accommodate a bone pin. The locking assembly includes a second fastening element configured to engage with the first fastening element. The locking assembly is configured to restrict movement of the first fixation element and the bone pin relative to the clamp body in response to tightening of the locking assembly.

17 Claims, 55 Drawing Sheets

(52) U.S. Cl.
CPC ...... *A61B 17/6425* (2013.01); *A61B 17/6458* (2013.01); *A61B 17/6466* (2013.01)

(58) Field of Classification Search
CPC . A61B 17/6458; A61B 17/60; A61B 17/6425; A61B 17/6433; A61B 17/64; A61B 17/6441; A61B 17/6475; A61B 19/203; A61B 17/663
USPC ...................................... 606/53–59, 250–279
See application file for complete search history.

(56) References Cited

U.S. PATENT DOCUMENTS

| | | | |
|---|---|---|---|
| 4,895,141 A | 1/1990 | Koeneman et al. | |
| 5,116,334 A | 5/1992 | Cozad et al. | |
| 5,380,325 A | 1/1995 | Lahille et al. | |
| 5,443,464 A | 8/1995 | Russell et al. | |
| 5,443,465 A | 8/1995 | Pennig | |
| 5,624,440 A | 4/1997 | Huebner | |
| 5,653,707 A | 8/1997 | Taylor et al. | |
| 5,707,372 A | 1/1998 | Errico et al. | |
| 7,465,303 B2 | 12/2008 | Riccione et al. | |
| 7,803,174 B2 * | 9/2010 | Denis ................ | A61B 17/7035 606/250 |
| 2003/0187432 A1 | 10/2003 | Johnson et al. | |
| 2005/0228376 A1 | 10/2005 | Boomer et al. | |
| 2006/0229602 A1 | 10/2006 | Olsen | |
| 2006/0229604 A1 | 10/2006 | Olsen et al. | |
| 2007/0149973 A1 | 6/2007 | Clement et al. | |
| 2007/0161983 A1 | 7/2007 | Cresina et al. | |
| 2007/0161987 A1 * | 7/2007 | Capote ............... | A61B 17/7037 606/86 A |
| 2009/0118733 A1 | 5/2009 | Orsak et al. | |
| 2010/0318084 A1 | 12/2010 | Hajianpour | |

OTHER PUBLICATIONS

Partial International Search Report on International Application No. PCT/US2015/053316 mailed on Jan. 26, 2016.
US Office Action for U.S. Appl. No. 14/871,598 dated Feb. 11, 2016.
US Office Action on U.S. Appl. No. 14/871,613 DTD May 5, 2016.
Written Opinion of the Searching Authority for PCT/US2015/053316 mailed Apr. 8, 2016.
US Notice of Allowance on U.S. Appl. No. 14/871,598 DTD Jun. 8, 2016.
US Office Action on U.S. Appl. No. 14/871,613 DTD Aug. 26, 2016.

* cited by examiner

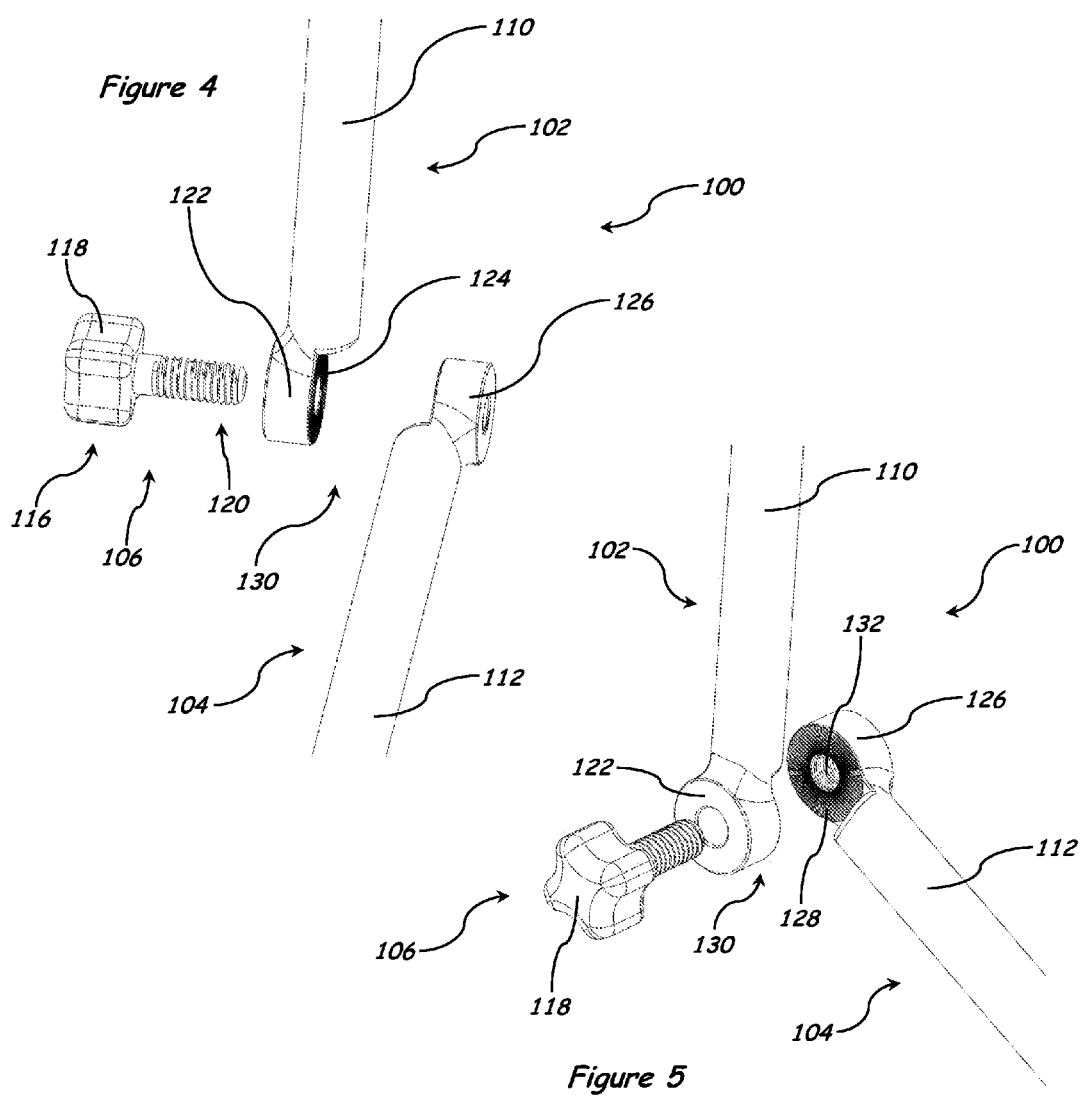

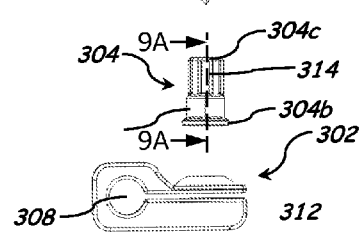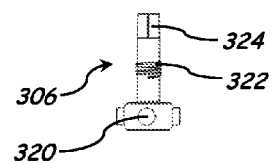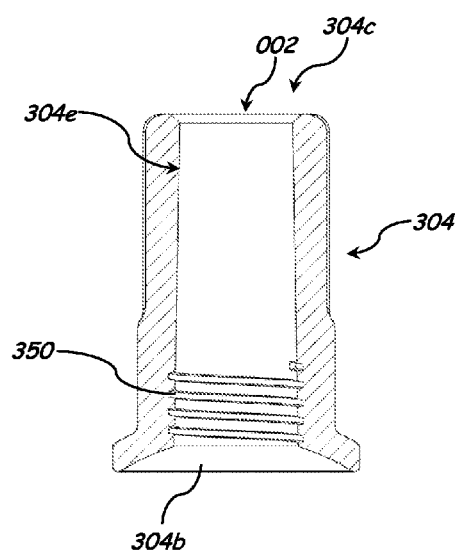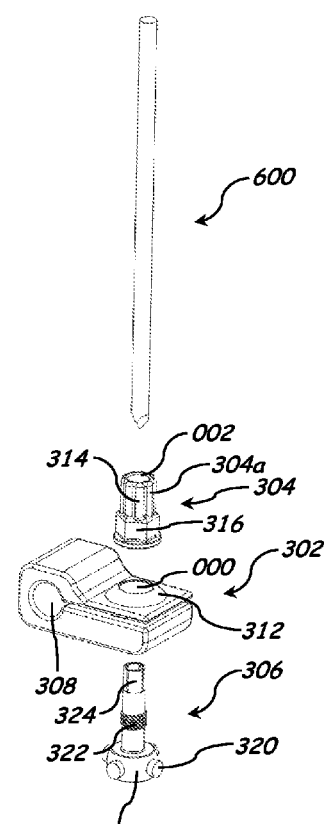
Figure 9
Figure 9A
Figure 10

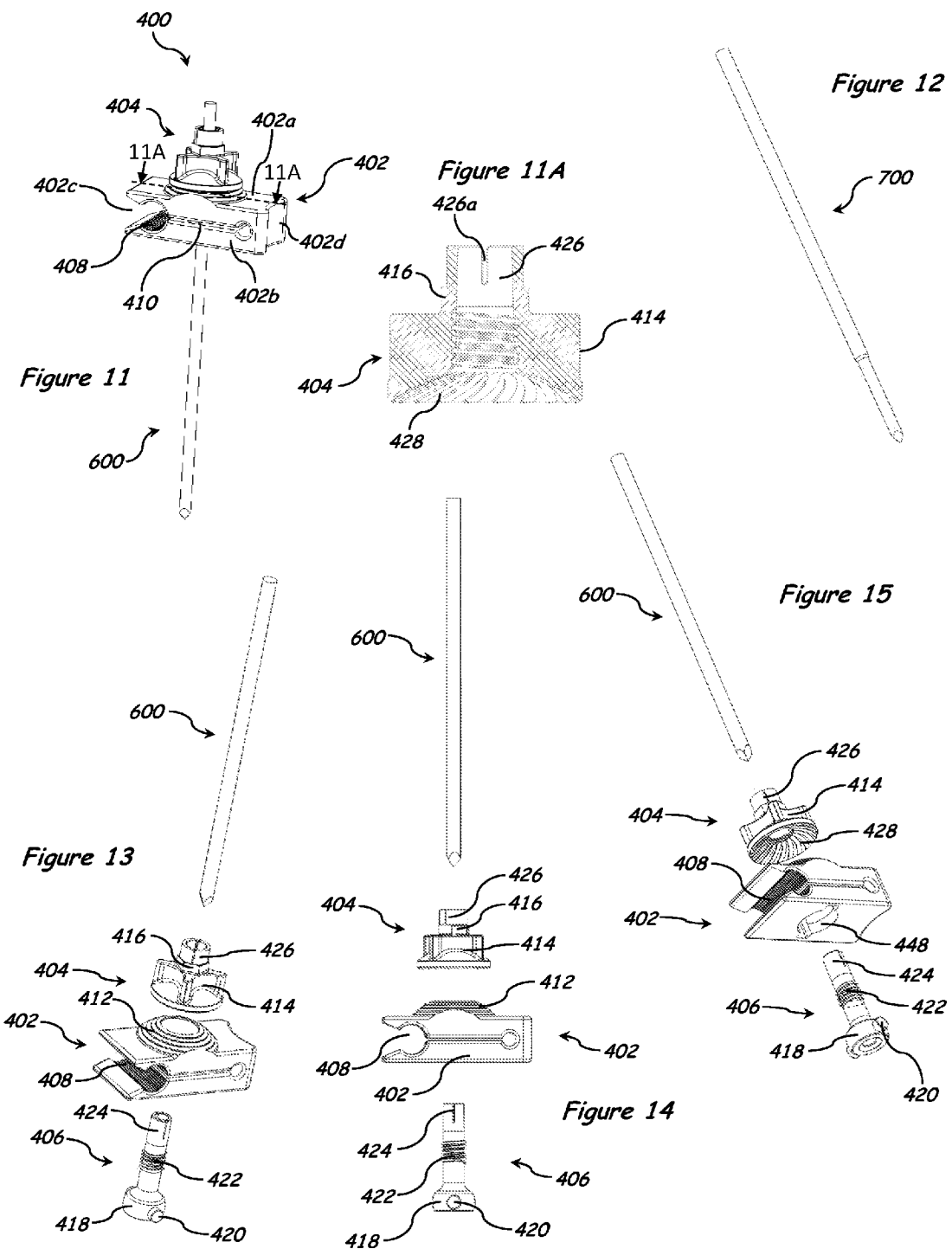

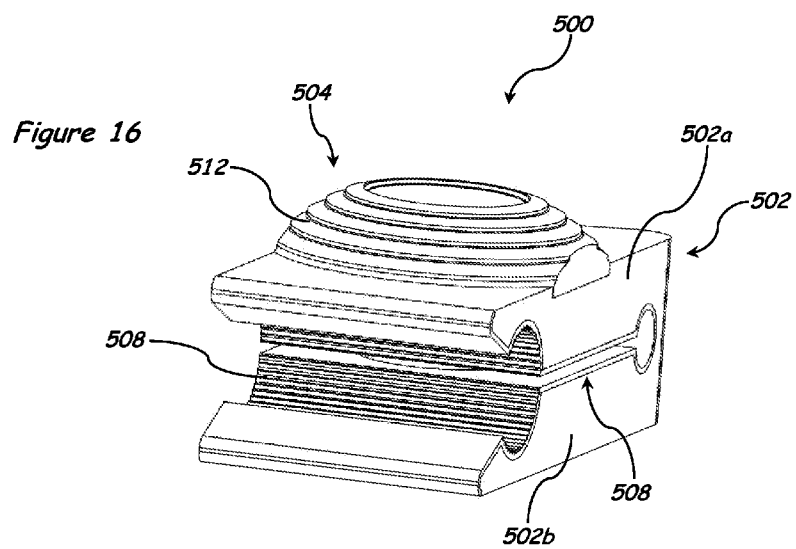
Figure 16
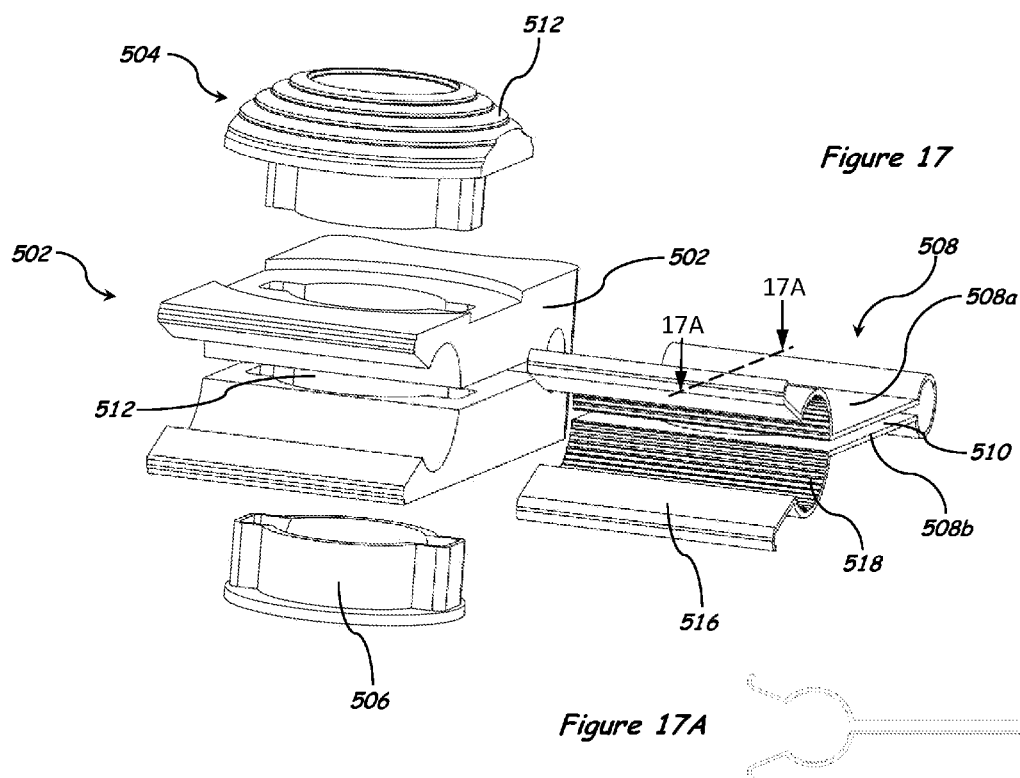
Figure 17
Figure 17A

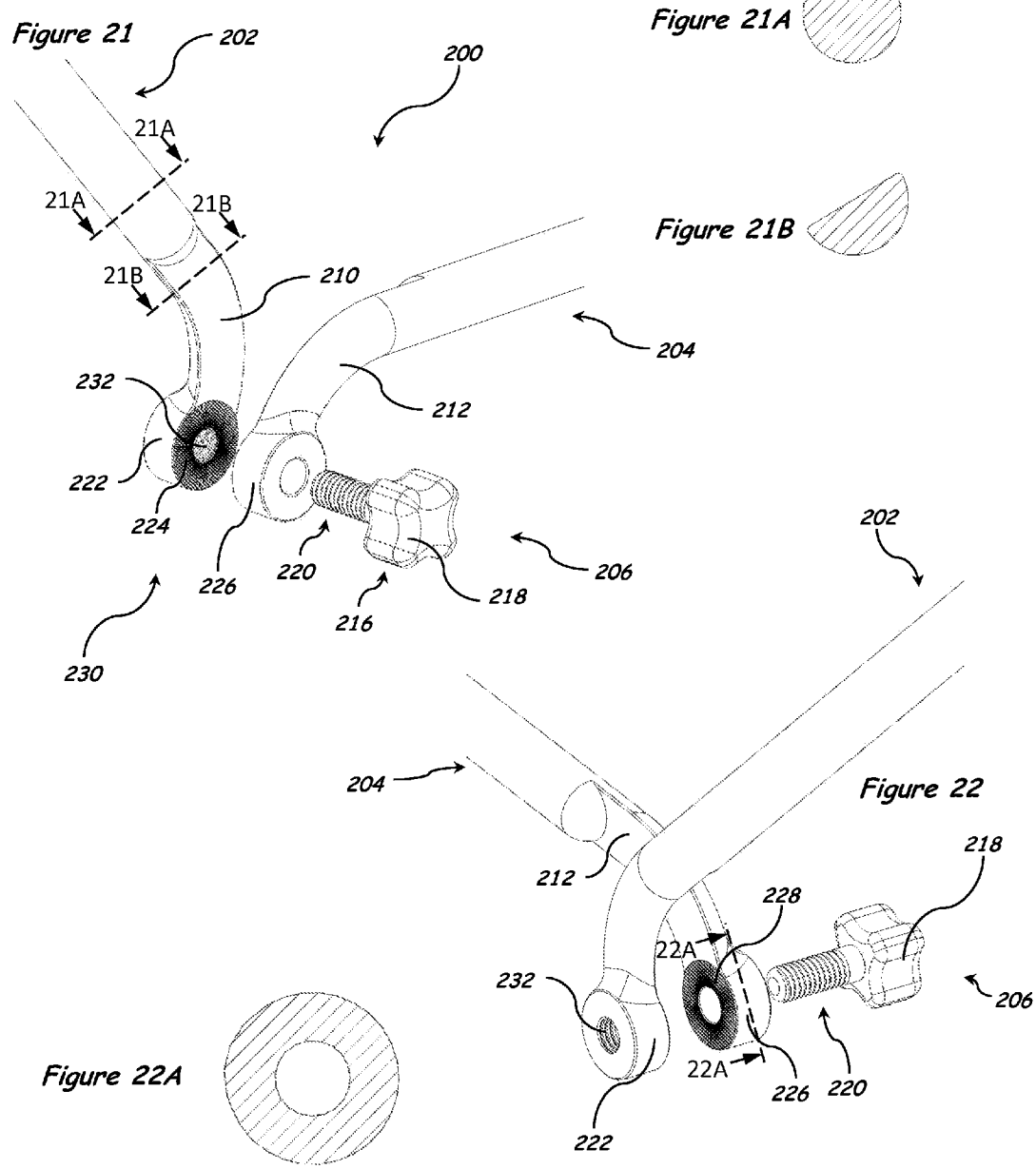

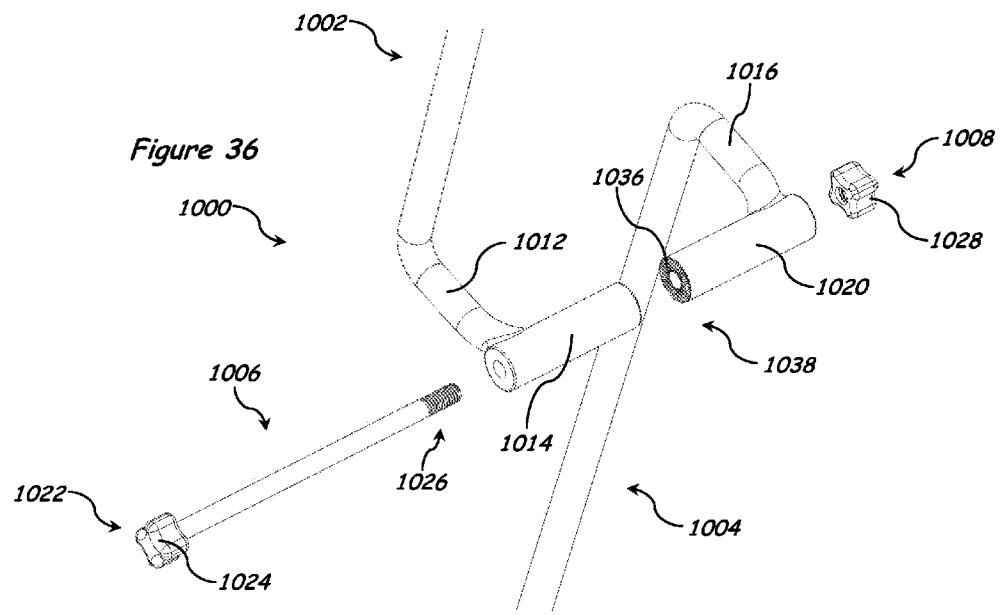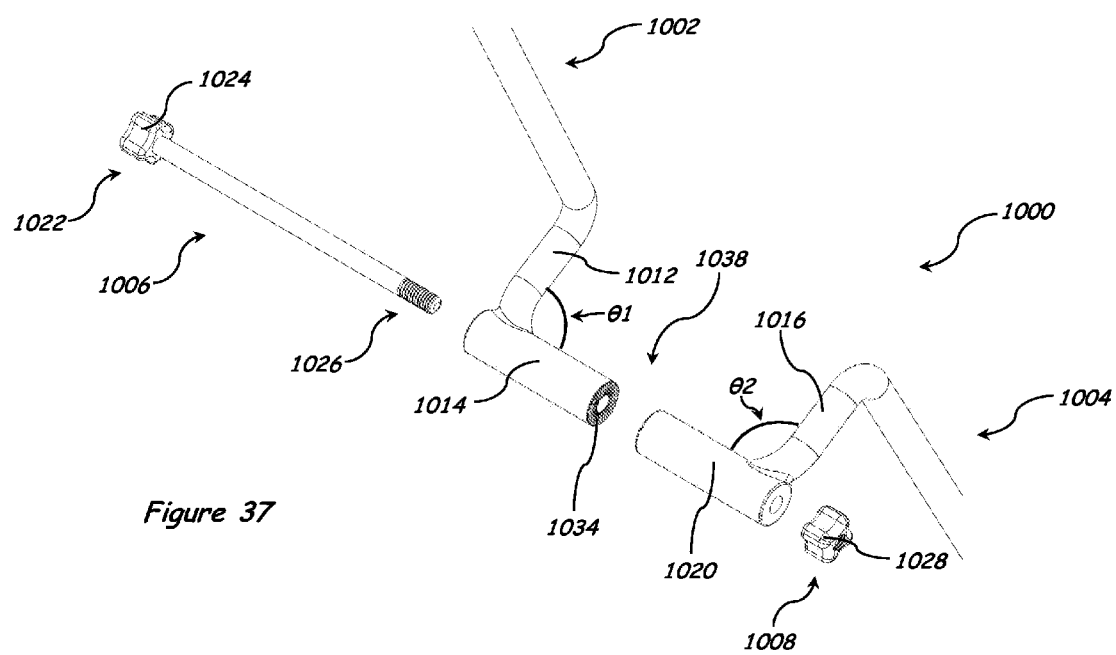

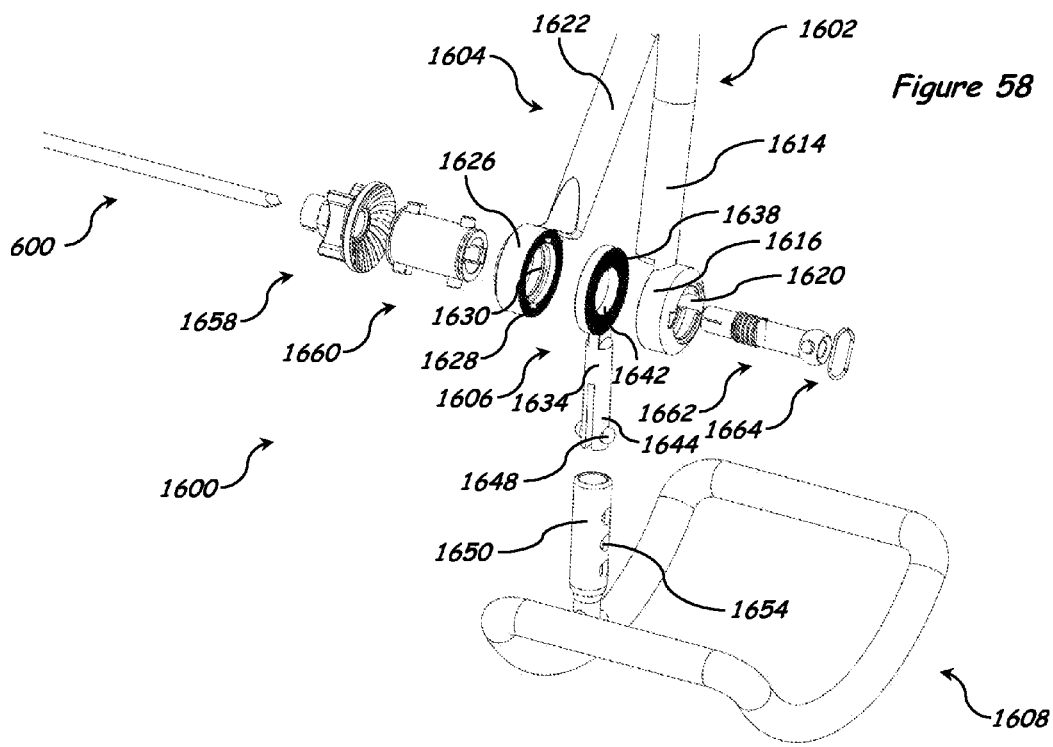
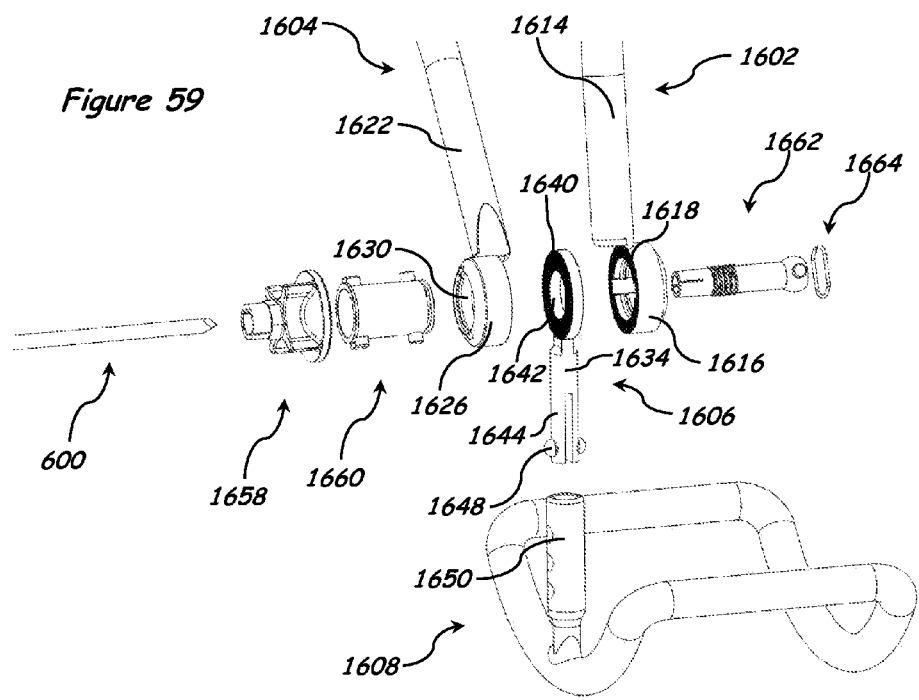

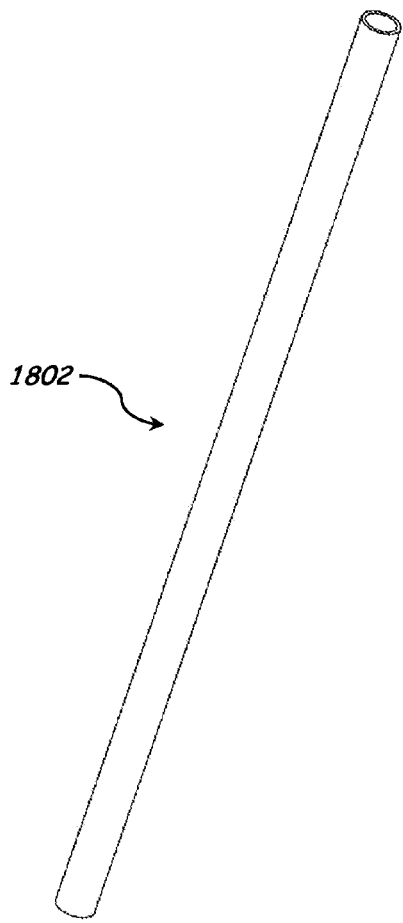
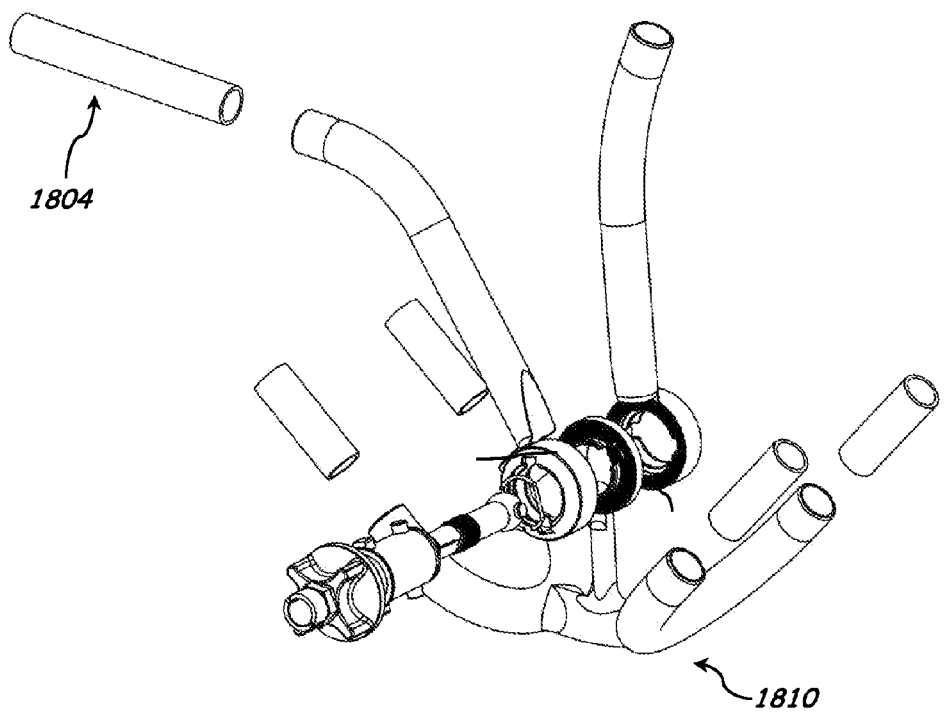
Figure 68

CLAMPING DEVICE FOR USE WITH AN ANATOMIC EXTERNAL FIXATION SYSTEM

RELATED APPLICATION

This application claims priority to U.S. Application 62/058,262, entitled "Anatomic External Fixation Device," filed on Oct. 1, 2014, which is incorporated herein by reference in its entirety for all purposes.

TECHNICAL FIELD

The present disclosure relates generally to fracture fixation systems, methods, and components. More particularly, the disclosure relates to improved anatomic external fixation systems, methods, and components. Particular embodiments described herein can be used to set bone fragments in long bone fractures (e.g., tibia fractures, femur fractures, fibula fractures, etc. . . . ).

BACKGROUND

External fixation devices have been widely used in the treatment of long bone fractures and are best suited in cases of unstable, comminuted fractures. An example of this would be a compound fracture of the tibia that would generally be fixed with a cast. If the fracture is too comminuted, the cast will be unable to provide enough support to the fragments, thus leading to a malunion or a nonunion. The external fixation device helps stabilize the bone fragments and allow the patient a quicker recovery time with fewer complications.

Current external fixation devices consist of straight rods and ring-frames made of carbon fiber that can be interconnected through the use of clamps. The clamps can be two sided with one side clamping to the straight bar and the other side clamping to a bone pin that is fixed to a bone or bone fragment. These two clamps are connected to each other via a ball joint that allows for some adjustability, thus allowing various angles in between the rods and the pins. Once the surgeon has adjusted the rods and pins to the desired positions, they have to lock everything in place by tightening nuts on each side of the clamp. The process of locking each clamp in place can be cumbersome and may require multiple assistants to aid in the procedure. This adds complexity and wastes valuable resources.

External fixator devices with hinges for fixing injury around joints such as the elbow, the knee, and the ankle are generally designed for use only on the right side or only on the left side of the joint or limb. These hinged systems must be mounted on the bone with the mechanical pivot axis of the device aligned with the natural pivot axis of the joint. These designed limitations not only demand that hospitals dedicate a large inventory for accommodating high volume of external fixator devices, but also increase surgical time and complexity in installing the devices on patients.

Therefore, a need exists for improved external fixation systems, methods, and components for use in fracture fixation.

SUMMARY

The present disclosure provides components and systems for externally fixing and precisely adjusting fractures in general, and more particularly fractures in a bone or near a joint, such as fractures near the elbow, knee, and ankle. The components and systems according to some exemplary embodiments wherein the same system can be used on either the right side or the left side of a bone or joint. According to some other exemplary embodiments, a single system can be used across both sides of the bone or joint simultaneously. The systems and their components include unitary construction, unitary modular construction and modular construction.

According to an aspect of the present disclosure, a hinged external fixator system for use adjacent to a joint such as the elbow includes a first fixation component coupled to a first bone portion having a first component proximal end portion and a first component distal end portion formed with a first pivot structure having a first through-bore and a first rough surface; a second fixation component coupled to a second bone portion having a second component distal end portion and a second component proximal end portion formed with a second pivot structure having a second through-bore and a second rough surface; a first fastener comprising a head and external threads; and optionally a second fastener, wherein at least one of said first through-bore, said second through-bore and said second fastener having an internal thread, wherein said first fastener extending from said first through-bore through said second through-bore, and optionally through said second fastener to form a threaded connection with at least one of said first pivot structure, said second pivot structure and optionally said second fastener which is disposed farthest from the head of the fastener to form a lockable articulator for hinging and locking said first and second fixation components in position.

According to another aspect of the present disclosure, the system as described above is used to treat a joint such as the ankle, further comprises a distal frame such as a foot frame having an inferior to posterior curvature or profile to protect the inferior and posterior aspects of a foot. At least a portion of a curved frame section of the foot frame is operatively positioned relative to the heel area of the foot. In some embodiments, the foot frame is an integral part of the first or second external fixation component. In other embodiments, the foot frame is permanently or removably connected to a third fixation component or frame connector formed with a third pivot structure comprising a third through-bore and a third rough surface and a fourth, opposing rough surface. A cartridge system for receiving a bone pin for coupling to a bone portion, such as the calcaneous, and locking the fixator system is configured to extend through the through-bores of the first, second and third fixation components, hinges and locks the fixation components. In use, the cartridge is coupled to a calcaneous or talus via the bone pin to provide further stability to the system and the injured joint. The cartridge can also provide fixed angular orientation to the bone pin.

According to another aspect of the present disclosure, the system or systems as described includes at least one novel clamping device which provides clamping or locking of multiple fixation elements (e.g. wire, pin, rod, bar) simultaneously by fastening a single knob. The clamping device of the present invention includes a clamp body comprising an upper jaw coupled to a lower jaw to form a first groove for accommodating a first fixation element along a longitudinal axis of the groove and a slot in communication with said groove. Each of the upper and lower jaws comprises a through-bore configured for receiving and cooperatively interacting with at least a portion of a locking assembly, which locking assembly configured to receive a second fixation element. The locking assembly includes a cannulated knob with internal threads and one or more tapered structure(s) and a cannulated shaft configured for clamping onto a bone pin extending through the clamp body and into the knob. The cannulated shaft includes a stopper on its external surface for preventing the shaft from passing completely through the clamp body, one or more slits, and external threads for engaging with the internal threads of the knob. In use, tightening of the knob flexes the upper and lower jaws toward each other to clamp the first fixation element and simultaneously circumferentially compress the slit portion guided through the knob via said internal tapered structure to clamp the second fixation element. In an alternative embodiment, the stopper formed with one or more slits cooperatively interact with a clamp body inner surface comprising varied diameters during locking or fastening to provide the clamping force onto the second fixation element. The novel clamping device thus provides dual function of a pin clamp and a fastener.

According to another aspect of the present disclosure, an external fixator system includes a first fixation component, a second fixation component, and a first fastener. The first fixation component extends between a first proximal end portion and a first distal end portion of the first fixation component, includes a first pivot structure including a first engagement surface and a first engagement feature, and is configured to support one or more first clamping devices that secure bone pins inserted within a first bone connected to a joint of a subject. The second fixation component extends between a second proximal end portion and a second distal end portion of the second fixation component, includes a second pivot structure including a second engagement surface configured to frictionally engage with the first engagement surface of the first fixation component, and is configured to support one or more second clamping devices that secure bone pins inserted within a second bone connected to the joint of the subject. The first fastener is configured to couple the first pivot structure to the second pivot structure and includes a first fastening element that includes a second engagement feature configured to engage the first engagement feature of the first pivot structure to maintain a first angle between a first longitudinal axis extending between the first proximal end portion and the first distal end portion of the first fixation component and a second longitudinal axis extending between the second proximal end portion and the second distal end portion of the second fixation component.

According to another aspect of the present disclosure, a surgical kit includes a first proximal end portion, a first distal end portion, a second proximal end portion, a second distal end portion, and a first fastener. The first proximal end portion is configured to support one or more first clamping devices that secure bone pins inserted within a first bone connected to a joint of the subject. The first distal end portion is configured to be coupled to the first proximal end portion, and includes a first pivot structure including a first engagement surface and a first engagement feature. The second proximal end portion is configured to support one or more second clamping devices that secure bone pins inserted within a second bone connected to the joint of the subject. The second distal end portion is configured to be coupled to the second proximal end portion and includes a second pivot structure including a second engagement surface configured to frictionally engage with the first engagement surface of the first fixation component. The first fastener is configured to couple the first pivot structure to the second pivot structure, and includes a first fastening element that includes a second engagement feature configured to engage the first engagement feature of the first pivot structure to maintain a first angle between a first longitudinal axis extending along the first proximal end portion and the first distal end portion when the first proximal end portion is coupled to the first distal end portion, and a second longitudinal axis extending along the second proximal end portion and the second distal end portion when the second proximal end portion is coupled to the second distal end portion.

According to another aspect of the present disclosure, an external fixator system includes a proximal frame configured to restrict motion in a lower extremity of a subject, and a frame connector assembly. The proximal frame includes a first fixation component, a second fixation component, and a third fixation component. The first fixation component is configured to support a first clamping device to secure a first bone pin inserted within a first bone extending between a foot and a knee of the lower extremity. The second fixation component includes a first end and a second end, the first end extending from a proximal end of the first fixation component. The third fixation component extends from a second end of the second fixation component. The first fixation component, the second fixation component, and the third fixation component have longitudinal axes that are substantially coplanar. The third fixation component includes an extension configured to extend over a dorsal portion of the foot of the subject and to support a second clamping device to secure a second bone pin inserted within a dorsal surface of a second bone of the bone. The frame connector assembly extends from the second fixation component to support a third clamping device to secure a third bone pin inserted within a third bone of the foot.

According to another aspect of the present disclosure, an external fixator system includes a first fixation component and a second fixation component. The first fixation component extends between a first proximal end portion and a first distal end portion of the first fixation component. The first fixation component includes a first pivot structure including a first engagement feature. The first fixation component is configured to support a first clamping device to secure a first bone pin inserted within a first bone extending between a foot and a knee of the lower extremity. The second fixation component extends between a second proximal end portion and a second distal end portion of the second fixation component. The second fixation component includes a second pivot structure including a second engagement feature configured to engage with the first engagement feature to restriction motion between the first fixation component and the second fixation component. The second fixation component is configured to support a second clamping device to secure a second bone pin inserted within a second bone of the foot. The first fixation component or the second fixation component includes an extension configured to support a third clamping device to secure a third bone pin inserted within a medial or lateral surface of a heel of the foot.

According to another aspect of the present disclosure, an external fixator system includes a first fixation component, a second fixation component, a fastener, and a bone pin insertion opening. The first fixation component extends between a first proximal end portion and a first distal end portion of the first fixation component. The first fixation component includes a first pivot structure and is configured to support a first clamping device to secure a first bone pin inserted within a first bone extending between a foot and a knee of the lower extremity. The second fixation component extends between a second proximal end portion and a second distal end portion of the second fixation component. The second fixation component includes a second pivot structure, and is configured to support a second clamping device to secure a second bone pin inserted within a second bone of the foot. The fastener is configured to engage the first pivot structure and the second pivot structure to restrict motion between the first fixation component and the second fixation component. The bone pin insertion opening is defined through the fastener, the first pivot structure, and the third pivot structure, to allow a third bone pin to pass through the defined opening for insertion within a medial or lateral surface of a heel of the foot.

According to another aspect of the present disclosure, a surgical kit includes a first fixation component, a second fixation component, a third fixation component, an extension, and a first frame connector. The first fixation component is configured to support a first clamping device to secure a first bone pin inserted within a first bone extending between a foot and a knee of a lower extremity of a subject. The first fixation component extends from a first proximal end to a first distal end. The second fixation component extends from a second proximal end to a second distal end and is configured to be coupled to the first distal end of the first fixation component. The third fixation component extends from a third proximal end configured to be coupled to the second distal end of the second fixation component to a third distal end. The extension is configured to be coupled to the third fixation component and to extend over a dorsal portion of the foot and to support a second clamping device to secure a second bone pin inserted within a dorsal surface of a second bone of the foot. The first frame connector extends from a first proximal frame end configured to be coupled to the second fixation component to a first distal frame end, and is configured to support a third clamping device to secure a third bone pin inserted within a third bone of the foot.

According to another aspect of the present disclosure, a clamping device for an external fixation system includes a clamp body and a locking assembly. The clamp body includes a first jaw and a second jaw. The first jaw and the second jaw define a slot extending between a first surface of the first jaw and a second surface of the second jaw and in communication with a first channel. The first channel is configured to accommodate a first fixation element along a longitudinal axis of the first channel. The first jaw defines a first opening and the second jaw defines a second opening that are sized to receive a portion of the locking assembly. The locking assembly includes a first fastening element configured to pass through the first opening and the second opening, and define a second channel configured to accommodate a bone pin for insertion into a bone of a subject. The locking assembly includes a second fastening element configured to engage with the first fastening element. The locking assembly is configured to restrict movement of the first fixation element relative to the clamp body and restrict movement of the bone pin relative to the clamp body in response to tightening of the locking assembly.

According to another aspect of the present disclosure, a surgical kit includes a bone pin, a first fixation element, a clamp body, a first fastening element, and a second fastening element. The bone pin is configured to be inserted into a bone connected to a joint of a subject. The first fixation element is configured to support the clamp body. The clamp body includes a first jaw and a second jaw defining a slot extending between a first surface of the first jaw and a second surface of the second jaw and in communication with a first channel. The first channel is configured to accommodate the first fixation element along a longitudinal axis of the first channel. The first jaw defines a first opening and the second jaw defines a second opening. The first fastening element is configured to pass through the first opening and the second opening and define a second channel configured to accommodate the bone pin. The second fastening element is configured to engage with the first fastening element. The fastening elements are configured to restrict movement of the first fixation element relative to the clamp body and restrict movement of the bone pin relative to the clamp body in response to tightening of the second fastening element to the first fastening element.

According to another aspect of the present disclosure, a method of fixating a bone fixator system about a target joint is disclosed. The bone fixator system includes a first bone fixator component pivotally coupled to a second bone fixator component. The method includes aligning the bone fixator components with at least one target bone disposed adjacent to the target joint. The method includes aligning a clamp with the at least one target bone. The method includes attaching a bone pin to the at least one target bone using the clamp as a drill guide. The method includes locking the clamp to one of the bone fixator components. The method includes locking the bone fixator system in a desired orientation.

According to another aspect of the present disclosure, a method of fixating a bone fixator system about a target ankle joint is disclosed. The bone fixator system includes a first frame coupled to a second frame, the second frame including an inferior frame portion and a posterior frame portion. The method includes aligning the first frame with a lower extremity adjacent to the target ankle. The method includes aligning the second frame to at least partially surround the target ankle such that the inferior frame portion is disposed in an inferior position relative to the target ankle, the posterior frame portion is disposed in a posterior position relative to the target ankle, and the posterior frame portion extends angularly from the inferior frame portion. The method includes aligning a first clamp with a first target bone of the lower extremity. The method includes attaching a first bone pin to the first target bone using the first clamp as a drill guide. The method includes locking the first clamp to the first frame.

Some or all of the systems, components and subcomponents of the present invention can be single-use or disposable. Also some or all of the systems, components and subcomponents of the present invention can be made of a unitary construction (formed from a single piece of metal or material) or unitary modular construction (plurality of components and/or subcomponents permanently connected by standard means, such as welding or soldering), or of modular construction (plurality of components and/or subcomponents removably connected by standard means, such as threading or snap-fitting).

These and other features of various embodiments can be understood from a review of the following detailed description in conjunction with the accompanying drawings.

It is to be understood that both the foregoing general description and the following detailed description are exemplary and explanatory and are not restrictive of the present invention, as claimed.

BRIEF DESCRIPTION OF THE DRAWINGS

FIG. 4 is a detailed anterior-medial exploded view of the first embodiment of the elbow external fixator.

FIG. 5 is a detailed anterior-lateral exploded view of the first embodiment of the elbow external fixator.

FIG. 9 is an exploded side view of the first embodiment of the closed clamp that can be utilized in all the embodiments of the external fixator.

FIG. 9A is a cross-sectional view taken along the line 9A-9A of FIG. 9

FIG. 10 is an exploded top perspective view of the first embodiment of the closed clamp that can be utilized in all the embodiments of the external fixator.

FIG. 11 is a perspective view of a first embodiment of an open clamp that can be utilized in all the embodiments of the external fixator.

FIG. 11A is a cross-sectional view taken along the line 11A-11A of FIG. 11

FIG. 12 is a perspective view of a double diameter pin used in the first embodiment of the open clamp.

FIG. 13 is an exploded top perspective view of the first embodiment of the open clamp that can be utilized in all the embodiments of the external fixator.

FIG. 14 is an exploded side view of the first embodiment of the open clamp that can be utilized in all the embodiments of the external fixator.

FIG. 15 is an exploded bottom perspective view of the first embodiment of the open clamp that can be utilized in all the embodiments of the external fixator.

FIG. 16 is a perspective view of a third embodiment of a multiple-part/multiple-material open clamp that can be utilized in all the embodiments of the external fixator.

FIG. 17 is an exploded perspective view of the third embodiment of the multiple-part/multiple-material open clamp that can be utilized in all the embodiments of the external fixator.

FIG. 17A is a cross-sectional view taken along the line 17A-17A of FIG. 17.

FIG. 21 is a detailed posterior-lateral exploded view of the second embodiment of the elbow external fixator.

FIG. 21A is a cross-sectional view taken along the line 21A-21A of FIG. 21.

FIG. 21B is a cross-sectional view taken along the line 21B-21B of FIG. 21.

FIG. 22 is a detailed anterior-lateral exploded view of the second embodiment of the elbow external fixator.

FIG. 22A is a cross-sectional view taken along the line 22A-22A of FIG. 22.

FIG. 36 is a detailed superior-lateral exploded view of the third embodiment of the knee external fixator.

FIG. 37 is a detailed superior-medial exploded view of the third embodiment of the knee external fixator.

FIG. 58 is a detailed posterior-lateral exploded view of the fourth embodiment of the ankle external fixator.

FIG. 59 is a detailed posterior-medial exploded view of the fourth embodiment of the ankle external fixator.

FIG. 68 is a detailed posterior-medial exploded view of the sixth embodiment of the ankle external fixator.

DETAILED DESCRIPTION

Figure 1:
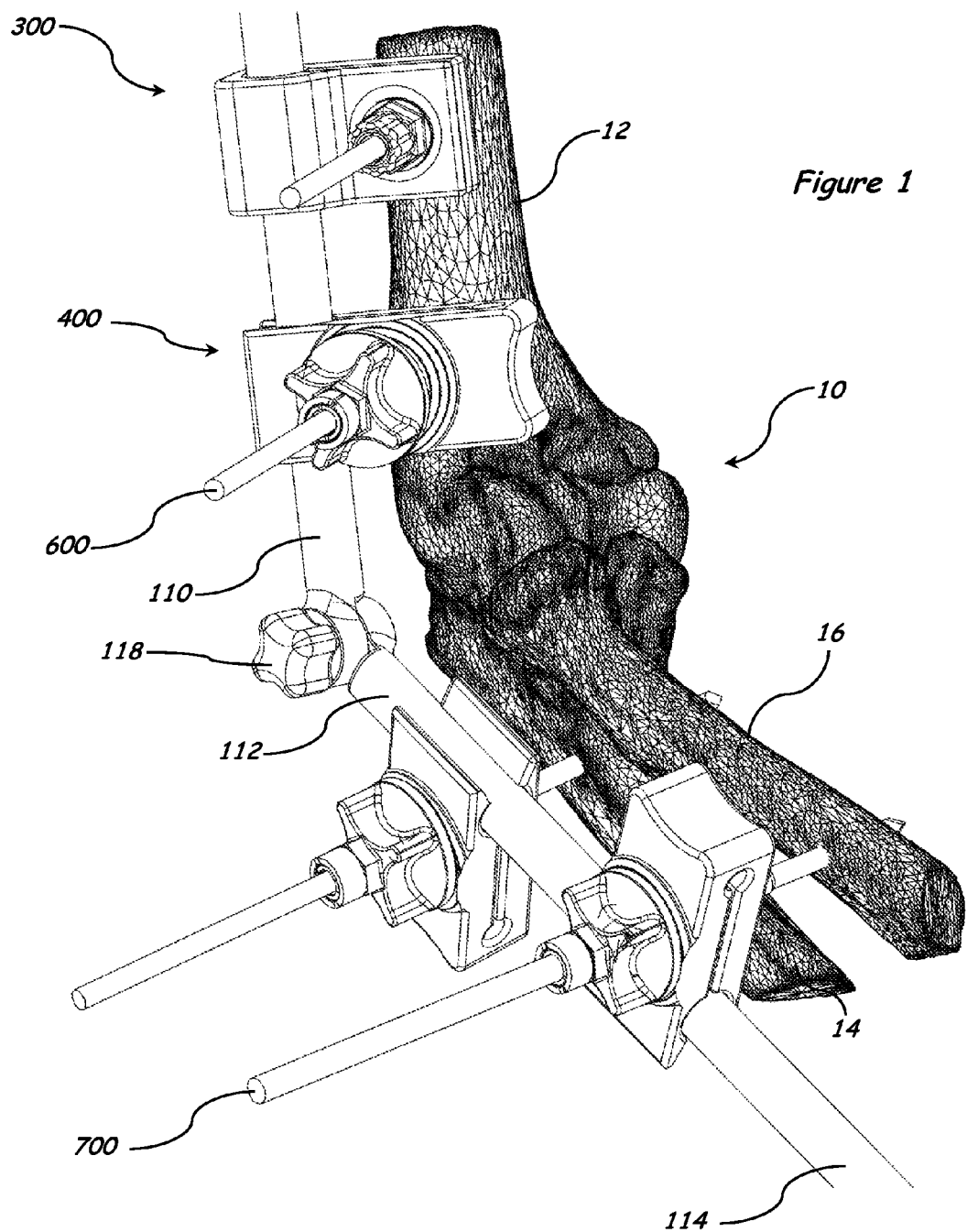
FIG. 1 is a superior-lateral perspective view of an elbow with a first embodiment of the elbow external fixator and its associated clamps.

The following detailed description and the appended drawings describe and illustrate various exemplary external fixation systems, methods, and components. The description and drawings are exemplary in nature and are provided to enable one skilled in the art to make and use one or more exemplary external fixation systems and/or components, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" and "coupled" grammatically related terms refers to the fixed, releasable, or integrated association of two or more elements and/or devices with or without one or more other elements in between. Thus, the term "attached" or "coupled" and grammatically related terms includes releasably attaching or fixedly attaching two or more elements and/or devices in the present or absence of one or more other elements in between. As used herein, the terms "proximal" and "distal" are used to describe opposing axial ends of the particular elements or features being described in relation to anatomical placement. As used herein, the terms "proximal," "distal," "inferior," "posterior," and any other relative position terms are intended to facilitate clarity regarding the disclosed embodiments, and do not limit the disclosure to any particular frame of reference.

While the systems, methods, and components described herein are exemplified by systems and methods for external fixation of bones, the systems, methods, and components described and illustrated herein can be used to treat any suitable ailment or joint within the body of an animal, including, but not limited to, humans. Skilled artisans will be able to select a suitable ailment and/or joint within the body of an animal to utilize a system and/or method described herein according to a particular embodiment based on various considerations, including the type of ailment and/or the structural arrangement at a treatment site. Example joints considered suitable to utilize a system, method, and/or component described herein include, but are not limited to, the elbow joint, the knee joint, and the ankle joint.

In some embodiments, components disclosed herein may be disposed in a substantially perpendicular orientation (e.g., having longitudinal axes that are less than 20 degrees from 90 degrees apart, less than 10 degrees from 90 degrees apart, less than 5 degrees from 90 degrees apart, less than 1 degree from 90 degrees apart, etc.). In some embodiments, components disclosed herein may be disposed in a substantially coplanar (e.g., being disposed in planes that are less than 20 degrees from coplanar, less than 10 degrees from coplanar, less than 5 degrees from coplanar, less than 1 degree from coplanar, etc.).

Figure 2:
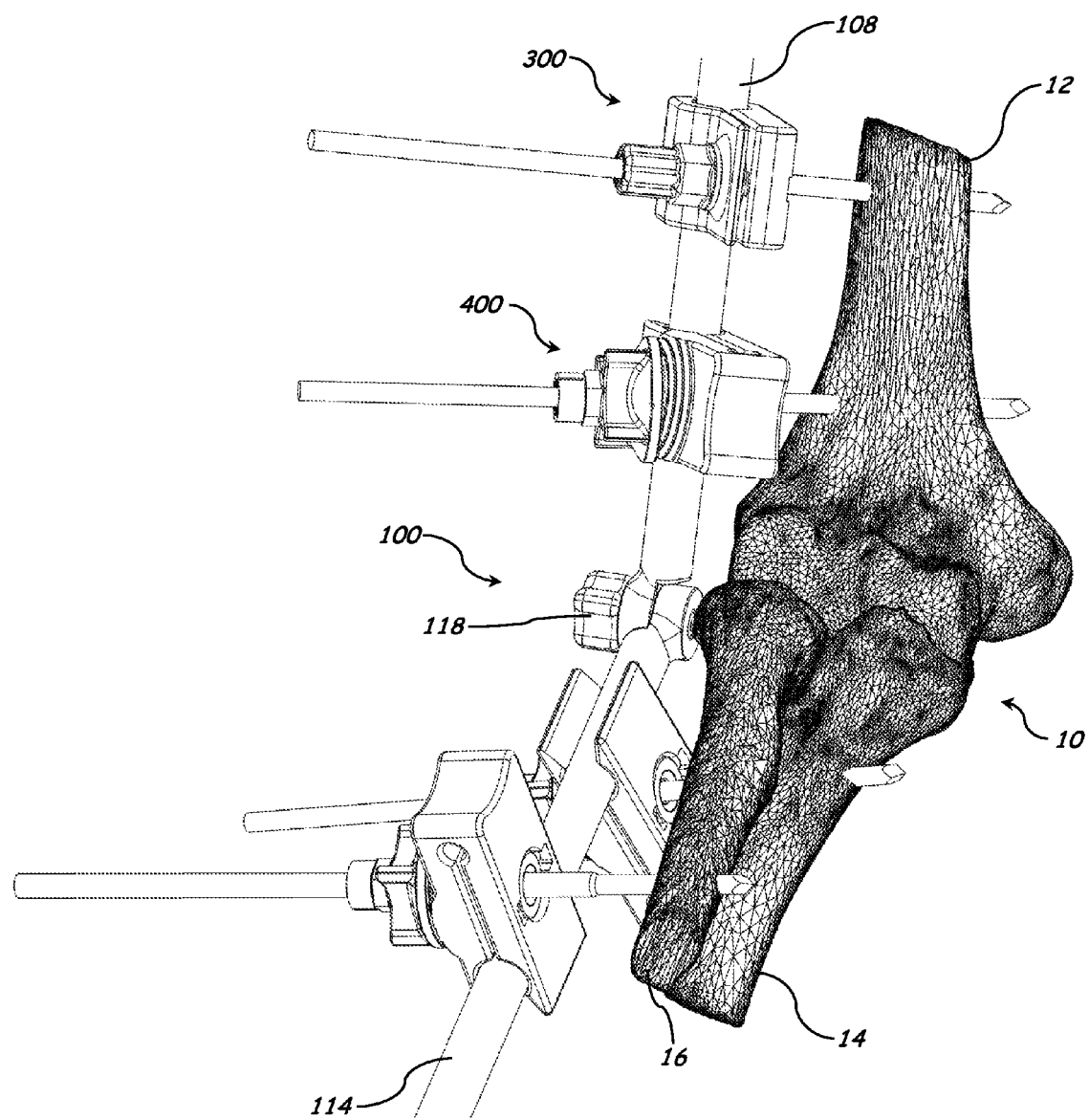
FIG. 2 is a superior-medial perspective view of an elbow with the first embodiment of the elbow external fixator and its associated clamps.
Figure 3:
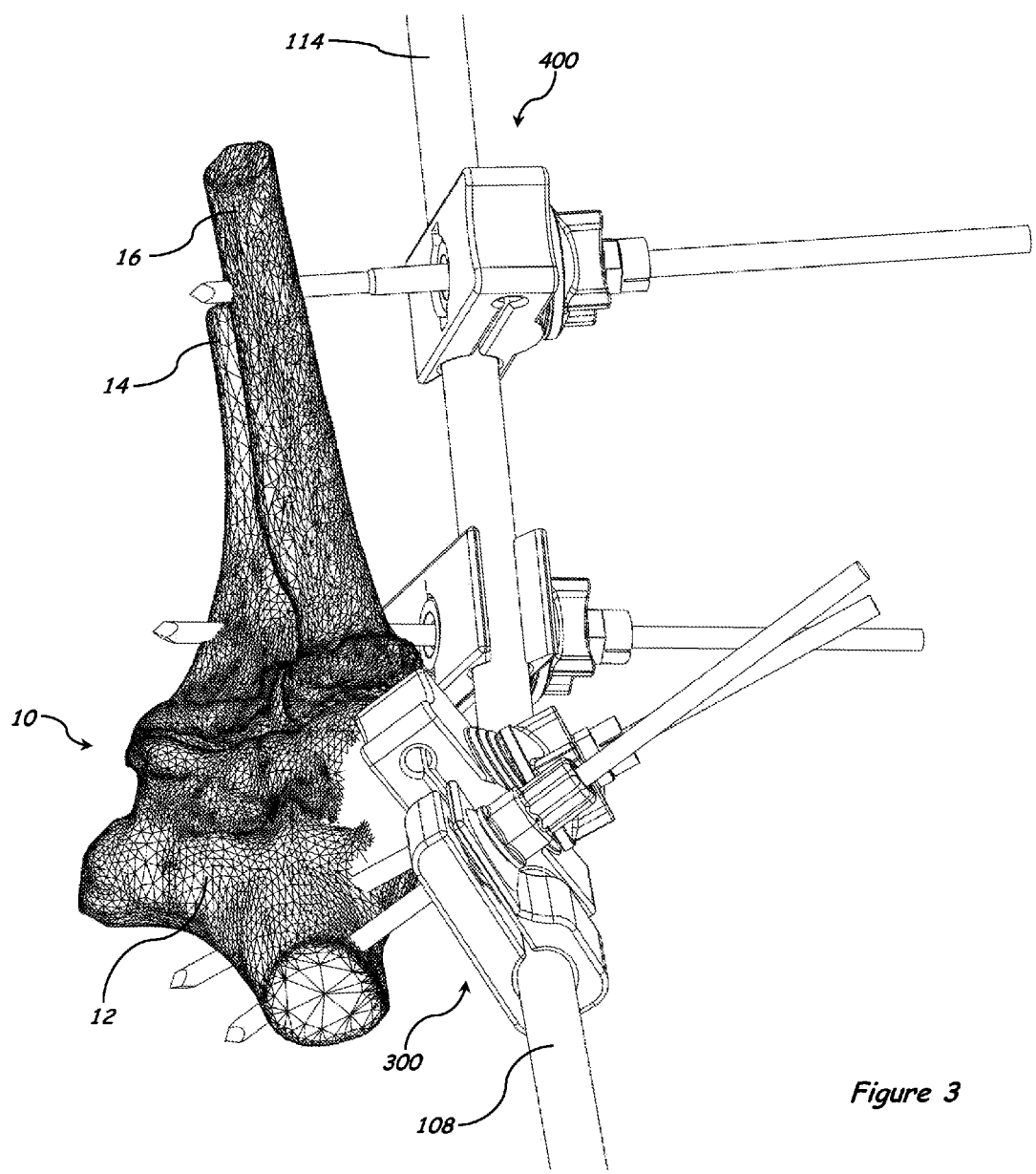
FIG. 3 is a superior perspective view of an elbow with the first embodiment of the elbow external fixator and its associated clamps.
Figure 6:
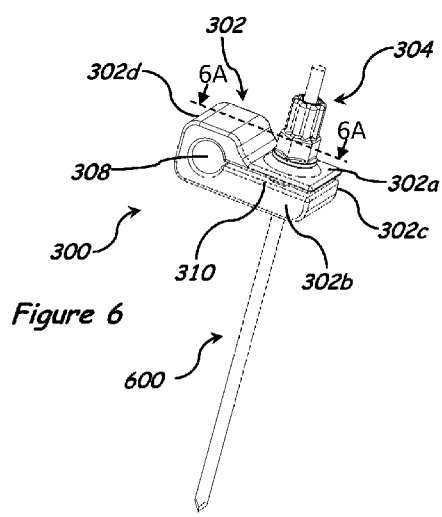
FIG. 6 is a perspective view of a first embodiment of a closed clamp that can be utilized in all the embodiments of the external fixator.
Figure 7:
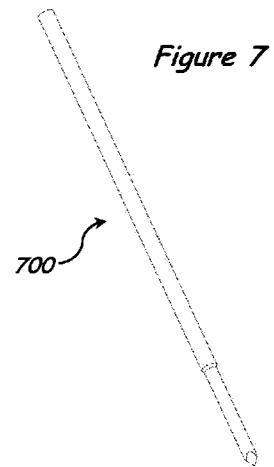
FIG. 7 is a perspective view of a double diameter pin that can be utilized in the first embodiment of the closed clamp.
Figure 6A:
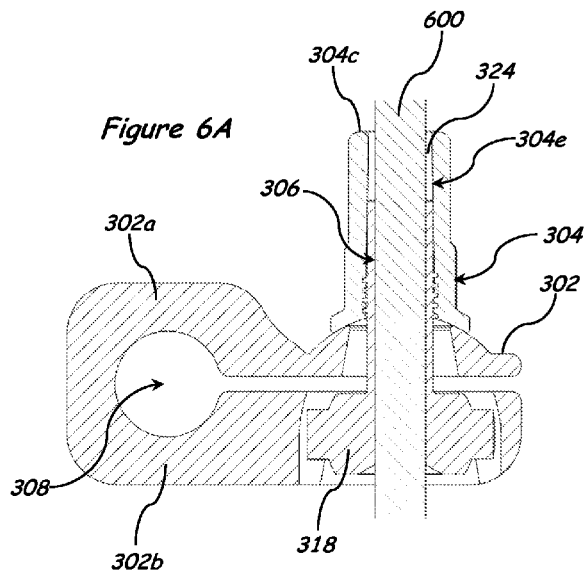
FIG. 6A is a cross-sectional view taken along the line 6A-6A of FIG. 6
Figure 8:
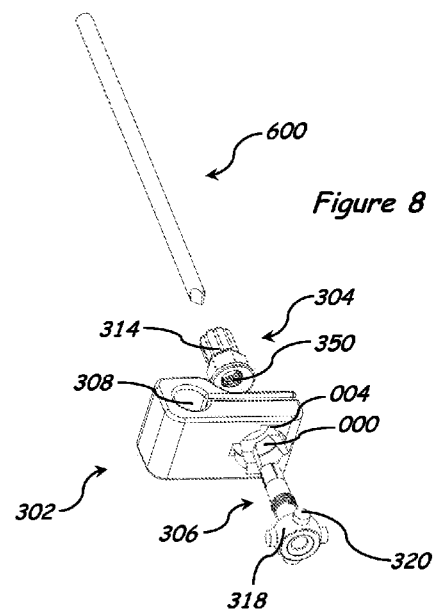
FIG. 8 is an exploded bottom perspective view of the first embodiment of the closed clamp that can be utilized in all the embodiments of the external fixator.
Figure 15A:
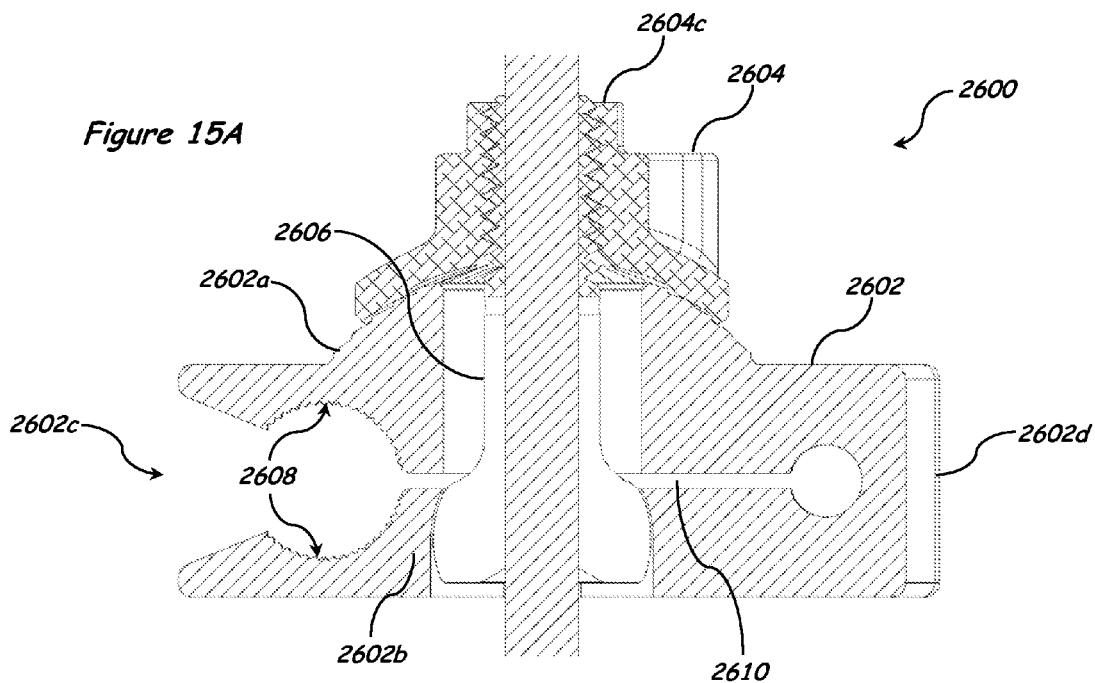
FIG. 15A is a cross-sectional view of a second embodiment of the open clamp system that can be utilized in all the embodiments of the external fixator.
Figure 15B:
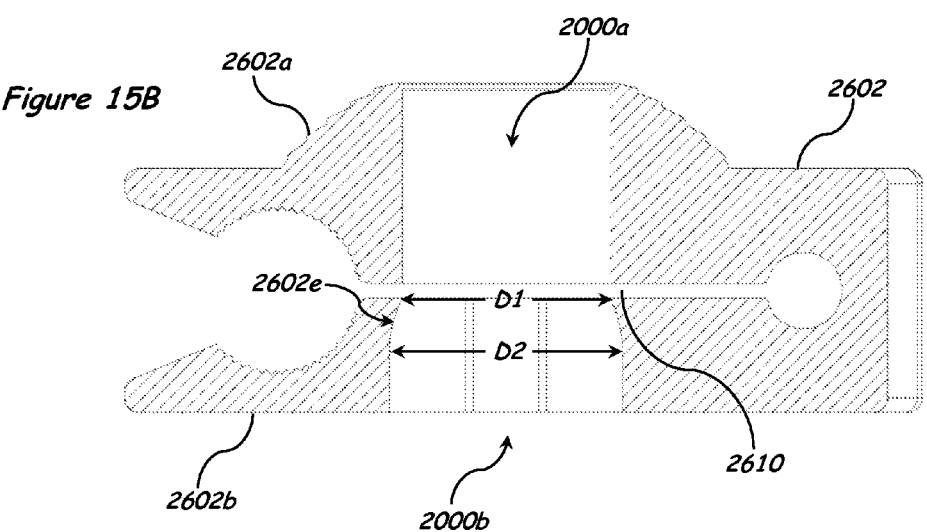
FIG. 15B is a cross-sectional view of the clamp body of FIG. 15A.
Figure 15C:
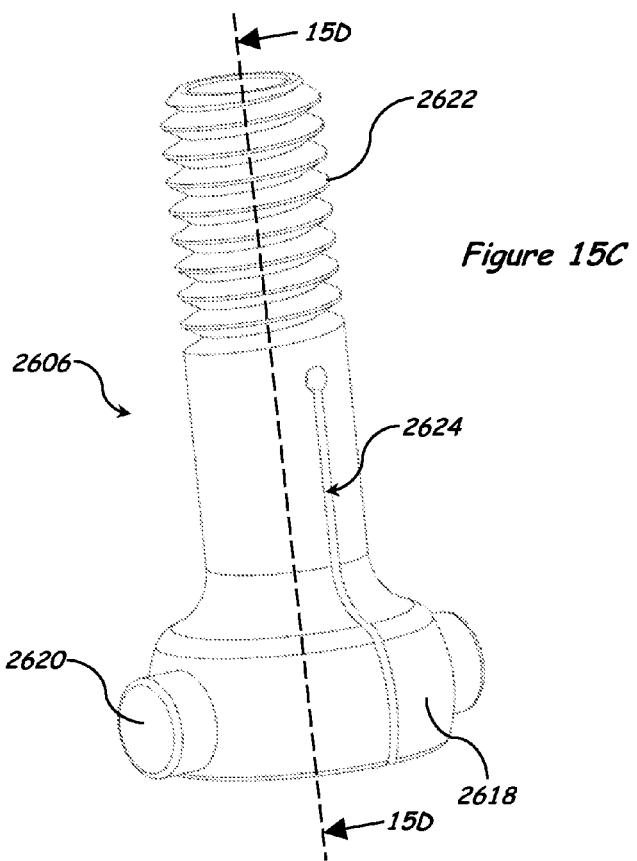
FIG. 15C is a side view of the shaft of FIG. 15A.
Figure 15D:
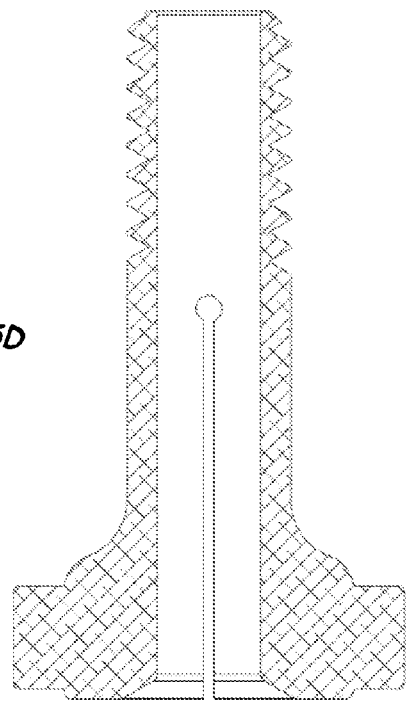
FIG. 15D is a cross-sectional view taken along the line 15D-15D of FIG. 15C.

FIGS. 1-3 illustrate an exemplary human elbow 10 comprising a humerus 12, ulna 14, and radius 16 and one embodiment of an exemplary elbow-spanning external fixation system 100.

FIGS. 1-5 illustrate a first embodiment of an exemplary elbow-spanning external fixation system 100 comprising a first external fixation component 102, a second external fixation component 104, a fastener or locking means 106, a closed-end clamp system 300 and an open-end clamp system 400. The first external fixation component 102 can be adapted to attach to the humerus 12, the ulna 14 and/or the radius 16 by use of the closed-end clamp system 300 and/or open-end clamp system 400. The second external fixation component 104 can be adapted to attach to the humerus 12, the ulna 14 and/or the radius 16 by use of the closed-end clamp system 300 and/or open-end clamp system 400.

The first external fixation component 102, second external fixation component 104, fastener 106, closed-end clamp system 300 and open-end clamp systems 400 and 500 (shown in FIGS. 16-17) can be formed of any suitable material known to one skilled in the art that provides an adequate stiffness or resistance to torsion, stress, torque and/or other forces that may be applied to the system 100, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 100 shown in FIGS. 1-5, the first external fixation component 102 comprises a first component proximal (e.g., first) end portion 108 and a first component distal (e.g., second) end portion 110. At least a portion of the first component proximal end portion 108 and at least a portion of the first component distal end portion 110 can be straight or curved. The first component distal end portion 110 includes a pivot structure 122 having a rough surface 124 and a through-bore having a circular cross-sectional shape for receiving a fastener such as fastener 106. The second external fixation component 104 comprises a second component proximal (e.g., first) end portion 112 and a second component distal (e.g., second) end portion 114. At least a portion of the second component proximal end portion 112 can be straight or curved. The second component proximal end portion 112 also includes a pivot structure 126 having a rough surface 128 and a threaded through-bore 132 having a circular cross-sectional shape for receiving a fastener such as fastener 106. The first external fixation component 102 and second external fixation component 104 are coupled and locked via a locking means such as a fastener 106 having a head 116 and at least a portion of its shaft threaded 120. The fastener 106 is configured to extend through the through-bore of the first pivot structure 122 and the threaded through-bore of the second pivot structure 126 to form a threaded connection with the second pivot structure 126 to form a movable hinge, articulator or mechanical joint 130. The hinge 130 is then locked in position by further tightening the fastener 106 which then interlocks the rough surface 124 of the first pivot structure 122 with the rough surface 128 of the second pivot structure 126. The interlocking or engagement of the rough surfaces 124 and 128 prevents the first and second external components 102 and 104 from rotating relatively to each other in a locking state.

Each of the first and second external fixation components 102 and 104 including their respective pivot structures 122 and 126 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). The first and second external fixation components 102 and 104 each can have any cross-sectional shape including circular, and non-circular such as oval, square, rectangle, triangle, or any polygonal shapes, and the cross-sectional shape can be different along the length of each component (e.g. semi-circle, circle). Each of the first and second external fixation components 102 and 104 can have uniform or varying diameter or thickness along its length. The first external fixation component 102 can be dimensioned and/or shaped to be the same or different from the second external fixation component 104.

The pivot structures 122 and 126 can be integrally formed or permanently attached by standard means such as welding or soldering or gluing, or removably coupled by standard means such as threading or snap-fitting, to any locations along the length of their respective first and second external fixation components 102 and 104 including the portion disposed between the distal end portion and the proximal end portion of each external fixation components 102 and 104. The pivot structures 122 and 126 can have any cross-sectional shape including circular, and non-circular such as oval, square, rectangle, triangle, or any polygonal shape. The length of each of the pivot structures 122 and 126 as measured along its axis of rotation or mechanical pivot axis X can be the same or different from the diameter or thickness of their respective first and second external fixation components 102 and 104. The end surfaces 124 and 128 of pivot structures 122 and 126 comprising the rough surface each lies in a plane perpendicularly intersecting the mechanical pivot axis, but can also lie in a plane intersecting the mechanical pivot axis at an angle other than 90 degrees. The rough surfaces 124 and 128 can include serration or radial interdigitation or other irregularly shaped features which provide friction enhancement or anti-rotation to the fixation components in a locking state. One skilled in the art may choose to have the rough surfaces be disposed on an outer surface of one of the first and second pivot structures 122 and 126 and on an inner surface of the other of the first and second pivot structures 122 and 126 to provide anti-rotation. The rough surfaces can also be provided as separate inserts coupled to the pivot structures 122 and 126. The pivot structures 122 and 126 can be an integral part of their respective external fixation components 102 or 104 or can be formed separately and assembled together later by welding, soldering or threading, for example. The pivot structures 122 and 126 each can be made of a unitary structure, a unitary modular or multi-component structure, or modular structure. An example of a modular pivot structure may include a pivot structure 122 or 126 having a non-circular cross-sectional shaped through-bore for receiving an insert having a matching, non-circular cross-sectional shape and a circular cross-sectional shaped through-bore with or without threads.

The locking means, such as fastener 106, comprises an enlarged structure, such as a head 116, with secure gripping surface features or geometry 118 for ease of handling the fastener during surgery, and a shaft 120 having engagement features such as threads which establish a threaded connection with the threaded through-bore 132 of the pivot structure 126 in the second external fixation component 104 during coupling and locking the external fixation components. The engagement features on the shaft can also include fins, protrusions or other fastening features known to one skilled in the art. The fastener 106 can also be a unitary, unitary modular or modular structure. An example of a modular fastener include a fastener as described but without the engagement features on is shaft, and a sleeve having engagement features on its outer surface adapted to cover the shaft of the fastener. The locking means can also include a first fastener such as fastener 106 and a second fastener such as a threaded nut. In this exemplary dual fastener system, both pivot structures 122 and 126 can have through-bores without threads or any engagement features, and arranged between the head of the first fastener and the nut. As the first fastener 106 or the second fastener (the threaded nut) is tightened down, the external fixation components 102 and 104 are coupled and locked in position.

FIGS. 6-15 describe various embodiments of a novel bone clamp configured to provide simple locking of various fixation elements such as wires, pins, rods and bars simultaneously. These clamping devices as described below can be used with the external fixation systems of the present invention to couple to bones, or with any existing or commercialized external fixation systems.

FIGS. 6-10 show an embodiment of a closed-end clamp system 300 comprising a clamp body 302, a knob 304 and a shaft 306. The clamp body 302 having an open end 302c and a close or hinged end 302d connecting an upper jaw 302a to a lower jaw 302b forming a groove or aperture 308 for receiving an external fixation element such as the first or second external fixation components 102 and 104, and a slot or spacing 310 in communication with the aperture 308. Each of the upper and lower jaws 302a and 302b have a through-bore 000 formed in alignment and configured for receiving and operatively interacting with at least a portion of a locking element or locking assembly such as the shaft 306 configured for operably interacting with the knob 304 for locking the clamp system 300.

The knob 304 comprises a knob body 304a having a clamp body facing end 304b and an opposing end 304c and a through-bore dimensioned for receiving and operatively interacting with a shaft, such as shaft 306, and extending longitudinally from the clamp body facing end 304b to the opposing end 304c. The knob body 304a includes a funnel-like or frusto-conical internal surface 304e or an internal surface having one of more tapered facets to guide, receive and alternatively compress and release a slit end, or a funnel-like or tapered external surface, of a shaft such as the shaft 306 for clamping a fixation element such as bone pin 600. The funnel-like or frusto-conical internal surface 304e, or more generally the through-bore bound by walls extending from the clamp body facing end 304b to the opposing end 304c of the knob body 304a, is designed to be larger toward the clamp body facing end 304b than toward the opposing end 304c of the knob body 304a, and includes a first locking feature such as threads 350. The tapered internal surface 304e can also be an insert. The through-bore 002 or opening in the opposing end 304c of the knob 304 has a diameter smaller than the uncompressed diameter of the slit end 324 of the shaft 306 to provide interference fit among the inner surface 304e of the knob 304, the slit end 324 and the bone pin such as bone pin 600. The opposing end 304c of the knob body 304a can include one or more slits 426a or breakable lines as shown in FIG. 11A for accommodating a broader range of dimensional tolerances of the bone pin 600 or 700. The knob 304 can have irregularly shaped geometry 314 for providing a secure grip surface and optionally a hexagonally shaped geometry 316 that interfaces with a wrench.

The variable position shaft or shaft 306 includes an elongated body with a through-bore extending longitudinally along its length and dimensioned for receiving a fixation element, such as a bone pin 600 or 700, an end portion including a stopper or an enlarged structure or structures, such as head 318, which operatively interacts with at least a portion of an internal surface of one of said upper and lower jaws, such as jaws 302a and 302b, for preventing the shaft 306 from passing completely through the clamp body 302 or through the jaw 302a or 302b, which the stopper 318 first comes in contact with, and a locking or engagement feature such as threads 322 on the external surface of the shaft 306, and one or more breakable lines or slits 324 on an opposing end portion of the shaft. The slits 324 can also be disposed on the stopper 318 to provide similar compression onto the bone pin 600 or 700 during locking as shown in alternative embodiments of this invention. The tapered internal surface 304e of the knob body 304a and the interaction of the engagement features such as the threads 322 and 350 guide and releasably compress the slit end 324 of the shaft 306 to provide clamping of a fixation element, such as bone pin 600. In the case where no slits are provided to the end 324 of the shaft, or even if slits are provided, the end 324 of the shaft 306 can be tapered or have a funnel-like shape to match the tapered internal surface 304e of the knob body 304a. A portion of the shaft 306 or the stopper 318 can include an at least partially spherical surface to permit the shaft 306, and thus, the bone pin 600 or 700 disposed in the through-bore of the shaft 306 to orient relative to the clamp body 302, and can have at least one anti-rotation feature such as protrusion 320 adapted to sit in a key way 004 in the clamp body 302. Other anti-rotation features can be pins, recesses, splines, and the like. The shaft 306 is configured to extend through the clamp body 302 via the through-bores 000 in the upper and lower jaws 302a and 302b and into the through-bore of the knob 304 such that the stopper 318 is disposed in the clamp body 302 and at least a portion of the threads 322 of the shaft and the slit end 324 disposed inside the knob body 304a. The shaft threads 322 operably engage the internal threads 350 of the knob 304 in forming a threaded connection between the shaft 306 and the knob 304 to form a cannulation or reception for receiving a bone pin such as bone pin 600 of uniform diameter or bone pin 700 of varying diameter.

In operation, the tightening of the knob 304 shortens the distance between the knob 304 and the stopper 318 and thus, flexes the upper and lower jaws 302a and 302b towards each other to clamp on an external fixation element such as the first or second external fixation components 102 and 104 disposed in aperture 308. Simultaneously, the slit end 324 of the shaft 306 is pushed and guided by the tapered internal surface 304e of the knob body 304a toward the opposing end 304c of the knob 304 and compressed circumferentially onto the bone pin 600 or 700 at the opposing end 304c of the knob 304 as the slit end 324 is pushed through the smaller opening 002 at the opposing end 304c of the knob 304, and thus, clamping onto the bone pin 600 or 700 by interference fit.

The clamp body 302 can include an annular protrusion such as a convex annular protrusion 312 disposed adjacent to the through-bore of the upper jaw 302a for operably engaging with the clamp body facing end 304b of the knob 304 for secure engagement. The annular protrusion 312 can have engagement features on its external convex surface to lock angularly with other engagement features on an underside of the clamp body facing end 304b of the knob 304.

FIGS. 11-15 illustrate an alternative embodiment 400 of the closed-end clamp system 300. The open-end clamp device 400 is similar in design to the closed-end clamp device 300 except that the groove or aperture 408 is disposed adjacent to the open end 402c of the clamp body 402. The outer edges of the sides of the groove or aperture 408 along its length are chamfered to allow the clamp system 400 to easily snap onto a fixation element such as fixation components 102 and 104. The knob 404 has an under surface 428 having a rough surface such as a radial interdigitation pattern operably engaging a convex protrusion 412 having a rough surface such as circular steps disposed adjacent to the through-bore in the upper jaw 402a.

FIGS. 15A-15D illustrate an alternative embodiment 2600 of the open-end clamp system 400. The open-end clamp system 2600 comprises a clamp body 2602, a knob 2604 and a shaft 2606. The clamp body 2602 having an open end 2602c and a close or hinged end 2602d connecting an upper jaw 2602a to a lower jaw 2602b forming a groove or aperture 2608 for receiving an external fixation element such as the first or second external fixation components 102 and 104, and a slot or spacing 2610 in communication with the aperture 2608. The upper and lower jaws 2602a and 2602b have through-bores 2000a and 2000b formed in at least partial alignment and dimensioned for receiving at least a portion of a locking element or assembly, such as the illustrated assembly comprising the knob 2604 and the shaft 2606. One of the through-bores 2000a and 2000b of the upper and lower jaws 2602a and 2602b, such as through-bore 2000b, defines a first diameter D1 and a second diameter D2, wherein D1 is smaller and located closer to the slot 2610. The inner surface 2602e containing D1 and D2 is shown as partially spherical, but it can be conical, partially conical or frusto-conical, or faceted. The inner surface 2602e is configured and dimensioned to operatively interact with an external surface of a slit portion of the shaft 2606 to clamp onto a fixation element, such as bone pin 600 or 700, received in a through-bore formed along a length of the shaft 2606.

The knob 2604 comprises a longitudinally formed through-bore having an internal thread and dimensioned for receiving and operatively interacting with the shaft 2606. Other engagement features, such as tabs and fins, can be used in place of or in addition to the thread on the internal surface of the knob 2604. The opposing end 2604c of the knob body 2604 can include one or more slits, such as slits 426a as shown in FIG. 11A for accommodating a broader range of dimensional tolerances of the bone pin 600 or 700. The knob 2604 can have an external surface and/or shape for providing a secure grip surface and optionally a hexagonally shaped geometry that interfaces with a wrench.

The variable position shaft or shaft 2606 includes an elongated body with a through-bore extending longitudinally along its length and dimensioned for receiving a fixation element, such as a bone pin 600 or 700, a locking or engagement feature such as threads 2622 on the external surface of the shaft 2606, and a stopper or an enlarged structure, such as head 2618, formed with one or more slits 2624 extending longitudinally along at least a portion of the length of the shaft 2606, and operatively interacting with at least a portion of an inner surface of one of said upper and lower jaws, such as inner surface 2602e, for compressing the slit stopper 2618 to clamp onto the bone pin 600 or 700. The inner surface 2602e also, but not necessary, prevents the shaft 2606 from passing completely through the clamp body 2602, or through at least one of the jaws 2602a or 2602b which the stopper 2618 first comes in contact with, such as the jaw 2602b. Other features and designs on the inner surface of the clamp body 2602, or of any of its upper and lower jaws that operatively interact with at least a portion of the shaft 2606 to prevent the shaft 2606 from passing completely through are still within the spirit and scope of the present invention. The stopper 2618 has a partially spherical external shape and at least one anti-rotation feature, such as anti-rotation pin 2620 configured to mate with a feature, such as a key way, on an inner surface of the clamp body 2602. Other anti-rotation features can be splines, recesses, protrusions or the like. Other shapes including conical and faceted external shapes of the stopper are considered within the spirit and scope of the present invention. The through-bore of the shaft 2606 and the width of the slit 2624 are dimensioned to receive a fixation element, such as bone pin 600 or 700, with very little play between the shaft 2606 and the bone pin 600 in an uncompressed state and a tight fit between the shaft 2606 and the bone pin 600 or 700 in a compressed state. The shaft 2606 can comprise a tapered end. The engagement feature 2622 on the external surface of the shaft 2606 can have other forms such as fins and tabs for interacting with the corresponding engagement feature on the inner surface of the knob 2604 to form a mechanical connection for clamping the fixation components and elements. The shaft 2606 is configured to extend through the clamp body 2602 via the through-bores in the upper and lower jaws 2602a and 2602b and into the through-bore of the knob 2604 such that the stopper 2618 is disposed in the clamp body 2602 and at least a portion of the threads 2622 of the shaft is disposed and operatively interacts with the threads on the inner surface of the knob 2604a.

FIGS. 16-17 and 17A describe an alternate embodiment 500 of the open-end clamp system 400. The open-end clamp system 500 is of a modular type. The open-end clamp system 500 is similar to the open-end clamp system 400 except that the convex annular protrusion 512 being a two-piece insert made of a separate upper part 504 and a separate lower part 506, and each of the parts 504 and 506 being formed with two key ways matching the key ways on the inner surfaces of the through-bores in the upper and lower jaws 502a and 502b of the clamp body 502 for receiving the anti-rotation features 320, or 420. The open-end clamp system 500 further includes a separate clip or insert 508 disposed between the upper and lower jaws 502a and 502b of the clamp body 502 for modifying the space therein. The insert 508 including an upper jaw jacket 508a connected to a lower jaw jacket 508b to form an insert groove 518 for laterally receiving a fixation element such as fixation components 102 or 104. A through-bore is formed in each of said upper and lower jaw jackets 508a and 508b of the insert 508 and aligned with aligned through-bores formed in the upper and lower jaws 502a and 502b of the clamp body 502 for receiving the convex annular protrusion insert 512. The insert 508 includes a slot or spacing between said jaw jackets 508a and 508b and in communication with said insert groove 518 to allow the upper and lower jaws 502a and 502b of the clamp body 502 and the jaw jackets 508a and 508b of the insert 508 to flex during locking and unlocking of the clamp system 500. The insert 508 is configured to have an outer cross-sectional shape (FIG. 17A) being substantially the same as an inner cross-sectional shape of the clamp body 502 to allow the insert 508 to easily slide into the space between the upper and lower jaws 502*a* and 502*b* of the clamp body 502 and mate or attach to the inner surface of the clamp body 502. The insert groove 518 can include splines to help secure gripping onto the fixation element.

Although the foregoing exemplary embodiments describe clamping systems having upper and lower jaws joined together by a hinged or closed end, the clamping systems of various embodiments of the present invention can comprise two or pairs of two separate upper and lower jaws spaced apart via a flexible structure, such as a spring coil surrounding a fastener, such as shaft 306, extending through the through-bores in the upper and lower jaws of the clamp to form one or more grooves for receiving external fixation elements such as rods, bars, pins, and a slot between the upper and lower jaws to allow the jaws to flex during locking and unlocking.

Figure 18:
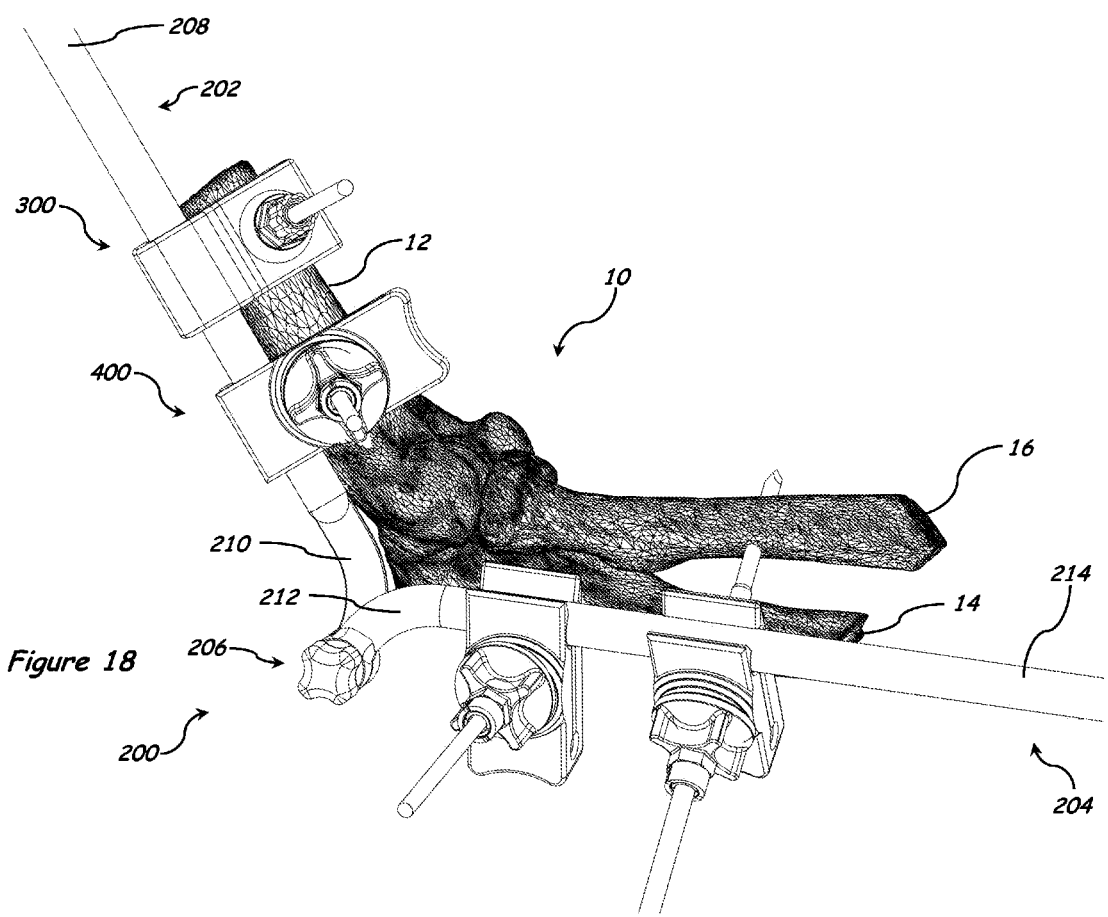
FIG. 18 is a lateral perspective view of an elbow with a second embodiment of the elbow external fixator and its associated clamps.
Figure 19:
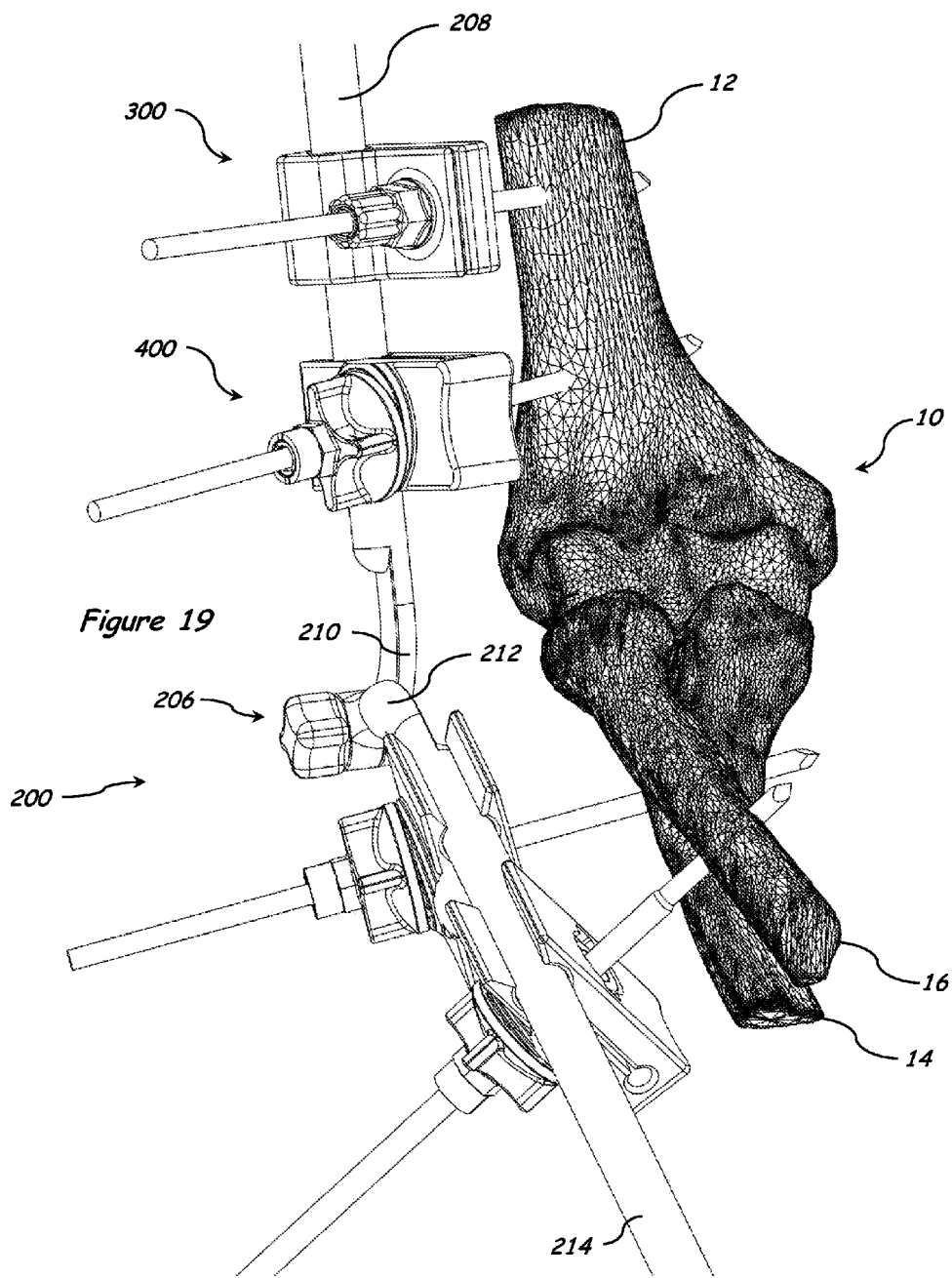
FIG. 19 is a superior-lateral perspective view of an elbow with the second embodiment of the elbow external fixator and its associated clamps.
Figure 20:
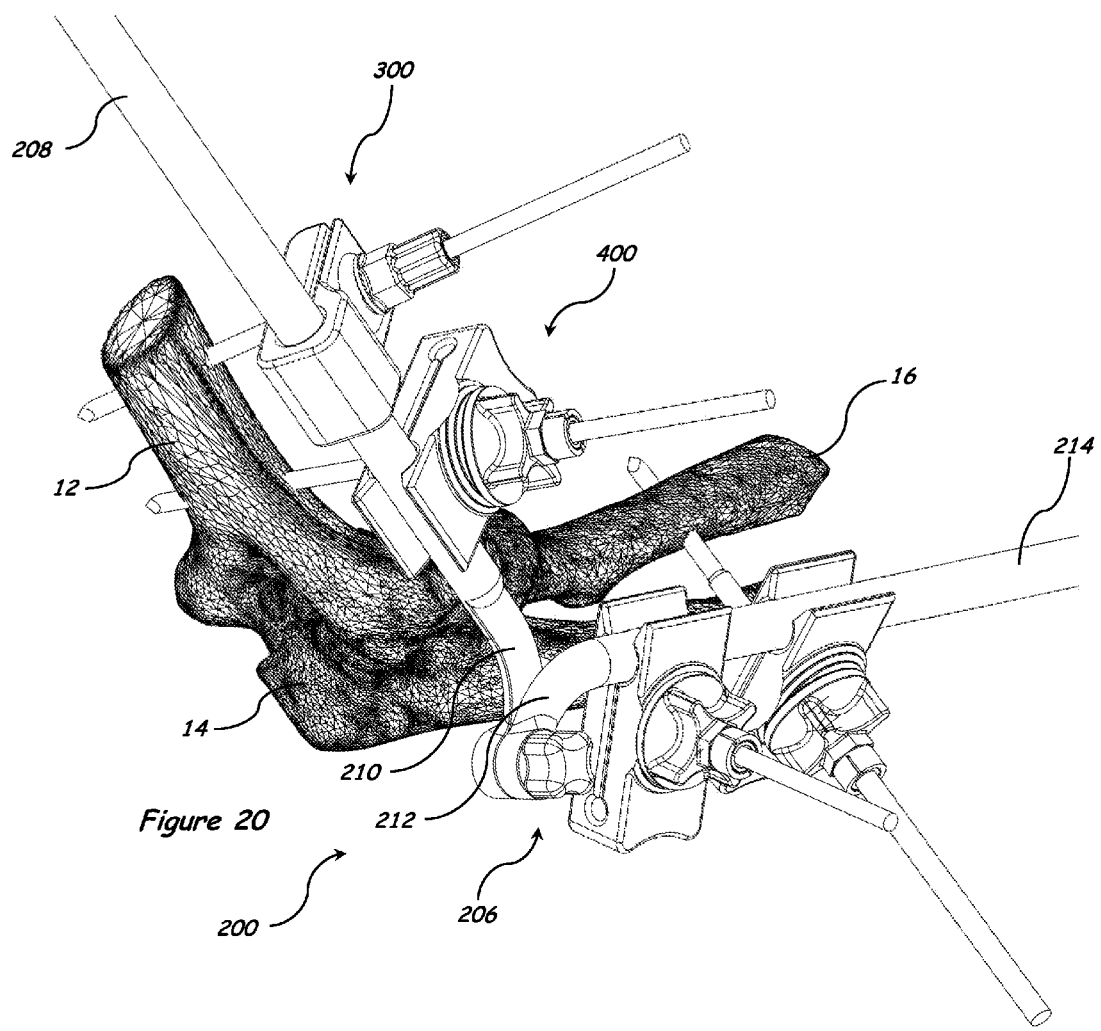
FIG. 20 is a posterior-lateral perspective view of an elbow with the second embodiment of the elbow external fixator and its associated clamps.

FIGS. 18-20 show an exemplary embodiment of an elbow-spanning hinged external fixation system 200 using the external fixator system including the novel clamp devices of the present invention. The system 200 is coupled to a human elbow 10 comprising a humerus 12, ulna 14, and radius 16. FIGS. 21-22 show exploded views of the hinge or articulator of the system 200.

Now referring to FIGS. 18-22, the elbow-spanning hinged external fixation system 200 comprising a first external fixation component 202, a second external fixation component 204, a fastener 206, a closed-end clamp system 300 and an open-end clamp system 400. The first external fixation component 202 can be adapted to attach to the humerus 12, the ulna 14 and/or the radius 16 by use of the closed-end clamp system 300 and/or open-end clamp system 400 and fixation elements such as bone pins. The second external fixation component 204 can be adapted to attach to the humerus 12, the ulna 14 and/or the radius 16 by use of the closed-end clamp system 300 and/or open-end clamp system 400.

The first external fixation component 202, second external fixation component 204, fastener 206, closed-end clamp system 300 and open-end clamp system 400 can be formed of any suitable material known to one skilled in the art that provides an adequate stiffness or resistance to torsion, stress, torque and/or other forces that may be applied to the system 200, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 200 in FIGS. 18-22, the first external fixation component 202 comprises a first component proximal (e.g., first) end 208 having a straight portion with circular cross-sectional shape (FIG. 21A) and a first component distal (e.g., second) end 210 comprising a curved portion with a semi-circular cross-sectional shape (FIG. 21B) formed with a first pivot structure 222 having a circular cross-sectional shape (FIG. 22A), and a through-bore with an internal thread 232 and a rough end surface 224. The first component proximal end 208 can be straight or curved. The second external fixation component 204 comprises a straight portion of cylindrical structure and a curved portion with semi-circular cross-sectional shape (FIG. 21B), a second component distal (e.g., first) end 214 and a second component proximal (e.g., second) end 212 comprising the curved portion formed with a second pivot structure 226 having a circular cross-sectional shape (FIG. 22A), a through-bore with no internal threads and a rough end surface 228. The second component distal end 214 can be straight or curved. Each of the first and second external fixation components 202 and 204 including their respective pivot structures 222 and 226 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). A fastener 206 having threads on its shaft 220 is configured to extend through the through-bore in the cylindrical pivot structure 226 of the second external fixation component 204 and the through-bore in the cylindrical pivot structure 222 of the first external fixation component 202, and forms a threaded connection with the cylindrical pivot structure 222. The first external fixation component 202 and second external fixation component 204 are attached to each other via the fastener 206 to form a movable hinge or joint 230. This movable hinge or joint 230 is then fixed in position by further tightening the fastener 206 which then interlocks the rough end surface 224 of the first pivot structure 222 with the rough end surface 228 of the second pivot structure 226. Thus, the first external fixation component 202 and the second fixation component 204 are now locked in position to reduce the bone fracture. The fastener 206 can have a distal end 216 with irregularly shaped external geometry 218 to provide a secure gripping surface, and a shaft 220 with engagement features that can interface with the engagement features such as fins or threads 232 in the second external fixation component 204.

The elbow-spanning hinged external fixation system 200 uses a combination of foregoing described embodiments of novel clamp systems 300, 400, and 500 for coupling the external fixation system 200 to the bone for fixing bone injury. This novel hinged system 200 significantly reduces surgical time by providing surgeons with flexibility in using the system on either side of the joint/body without having to align the mechanical pivot axis with the natural pivot axis of the joint, and ease of locking multiple fixation elements at once with a single tightening of a knob.

Figure 23:
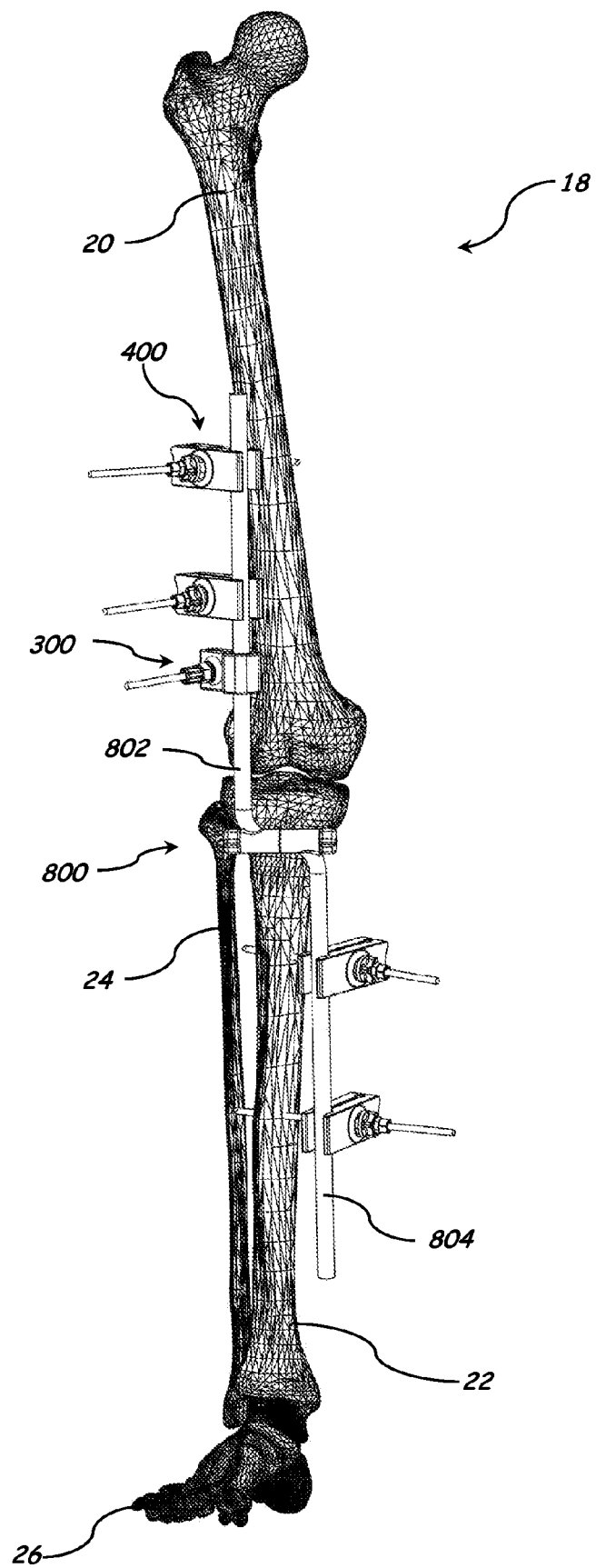
FIG. 23 is an anterior perspective view of a leg with a first embodiment of the knee external fixator and its associated clamps.
Figure 24:
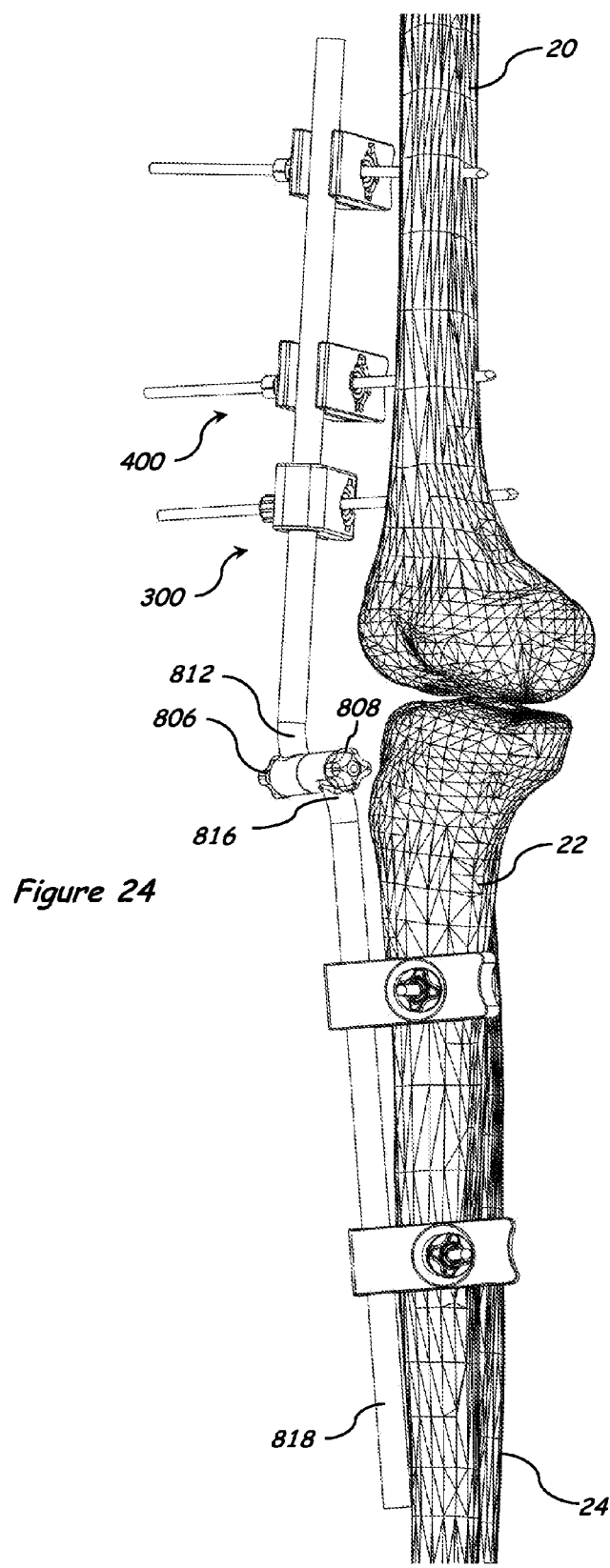
FIG. 24 is an anterior-medial perspective view of a leg with the first embodiment of the knee external fixator and its associated clamps.
Figure 25:
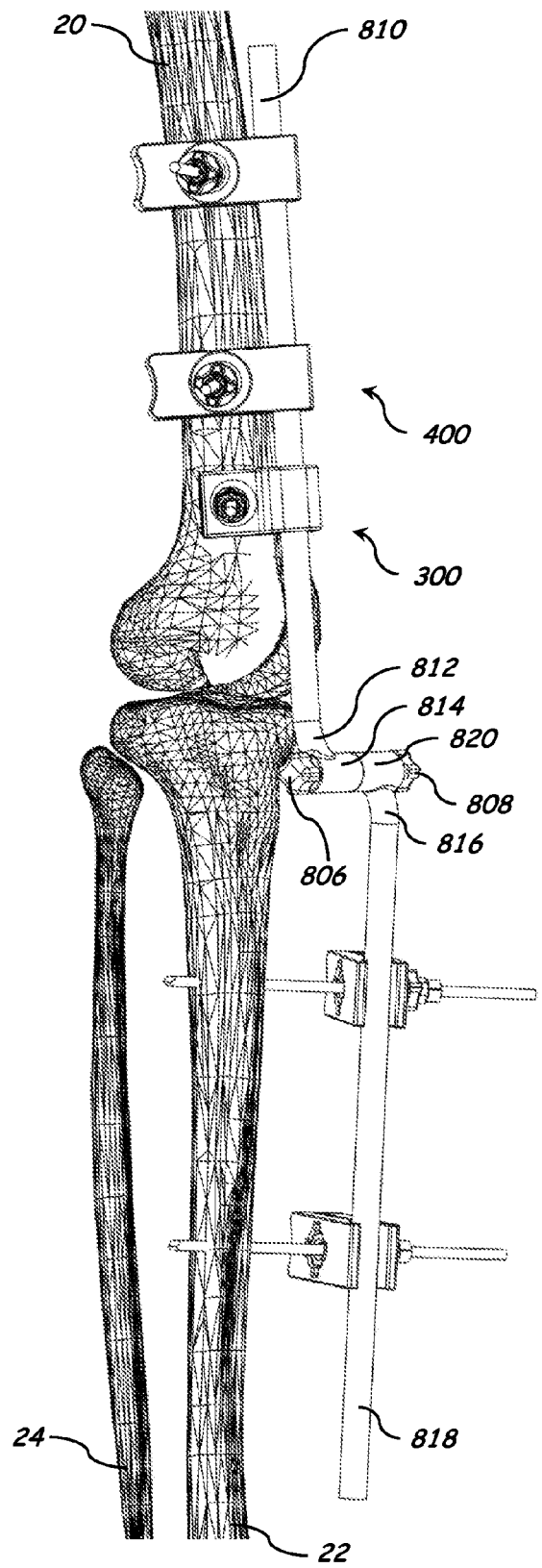
FIG. 25 is an anterior-lateral perspective view of a leg with the first embodiment of the knee external fixator and its associated clamps.
Figure 26:
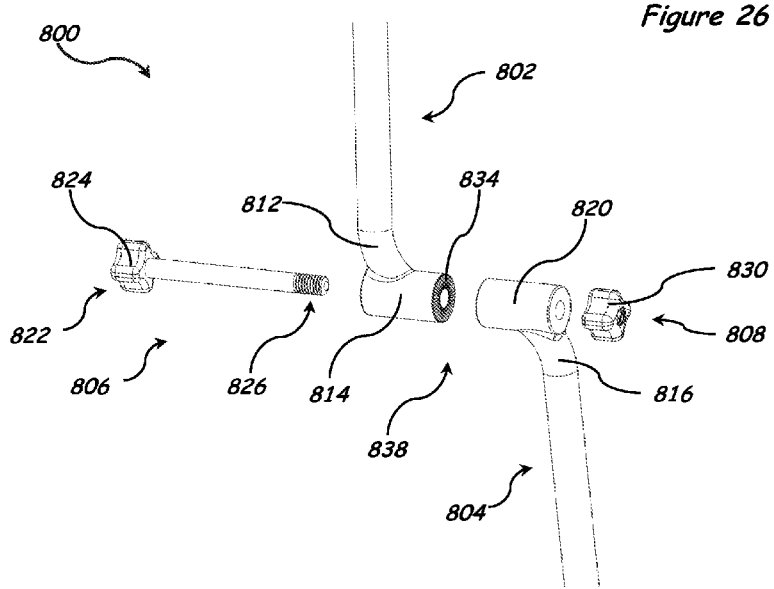
FIG. 26 is a detailed anterior-medial exploded view of the first embodiment of the knee external fixator.
Figure 27:
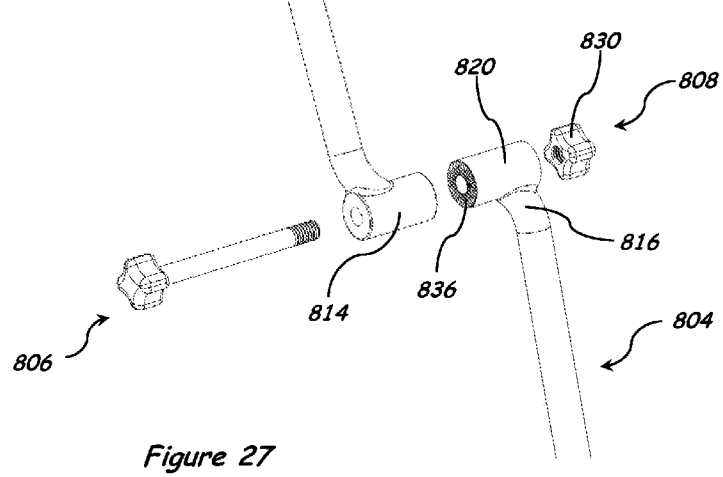
FIG. 27 is a detailed anterior-lateral exploded view of the first embodiment of the knee external fixator.
Figure 28:
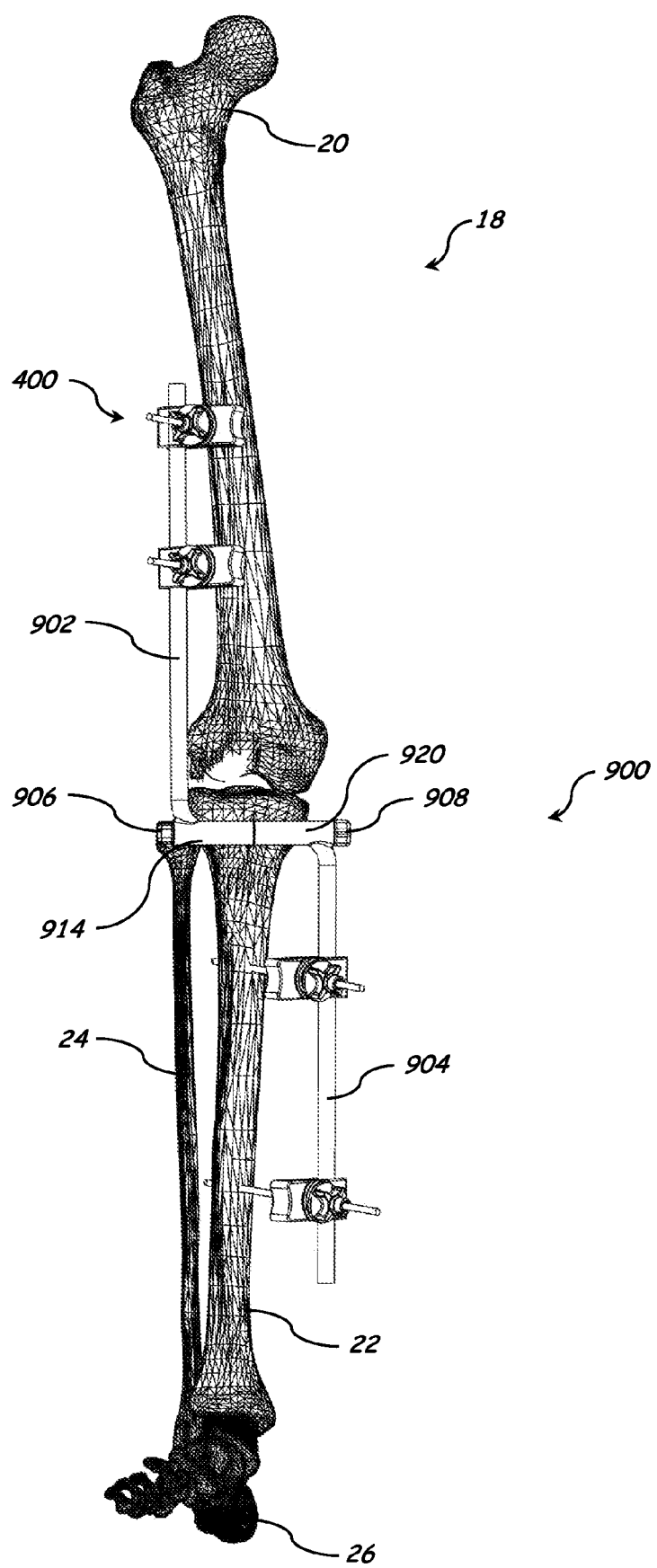
FIG. 28 is an anterior perspective view of a leg with a second embodiment of the knee external fixator and its associated clamps.
Figure 29:
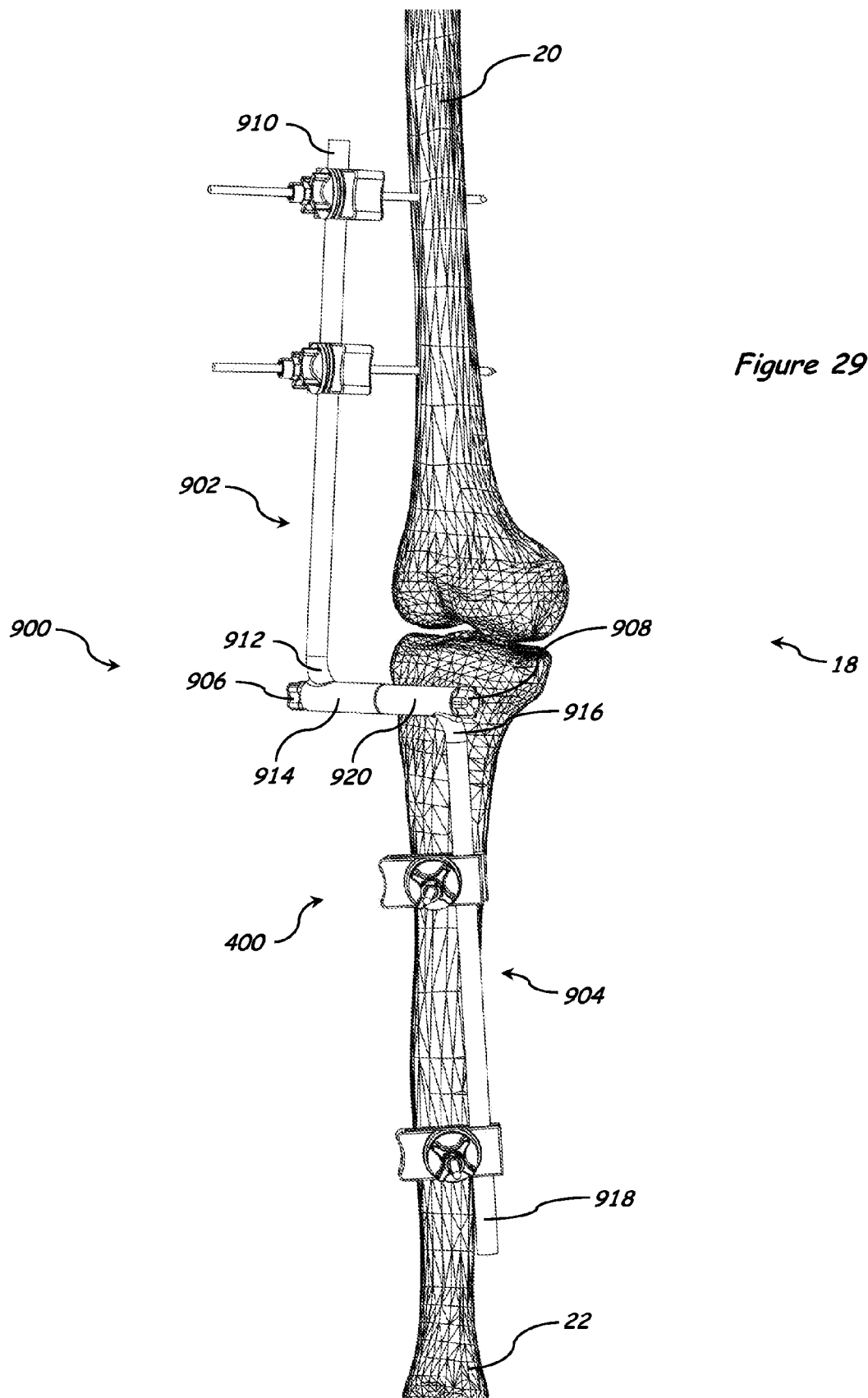
FIG. 29 is an anterior-medial perspective view of a leg with the second embodiment of the knee external fixator and its associated clamps.
Figure 30:
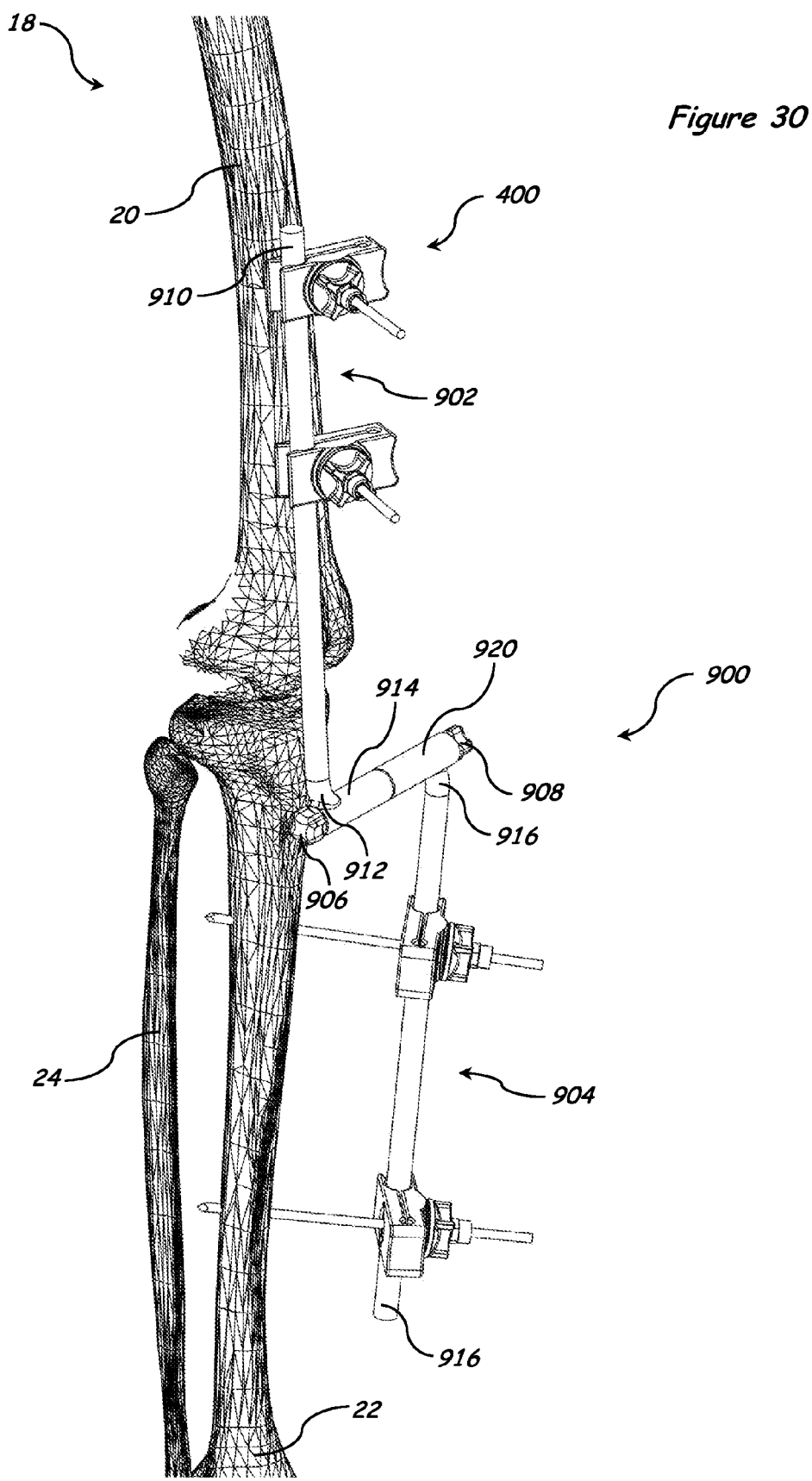
FIG. 30 is an anterior-lateral perspective view of a leg with the second embodiment of the knee external fixator and its associated clamps.
Figure 31:
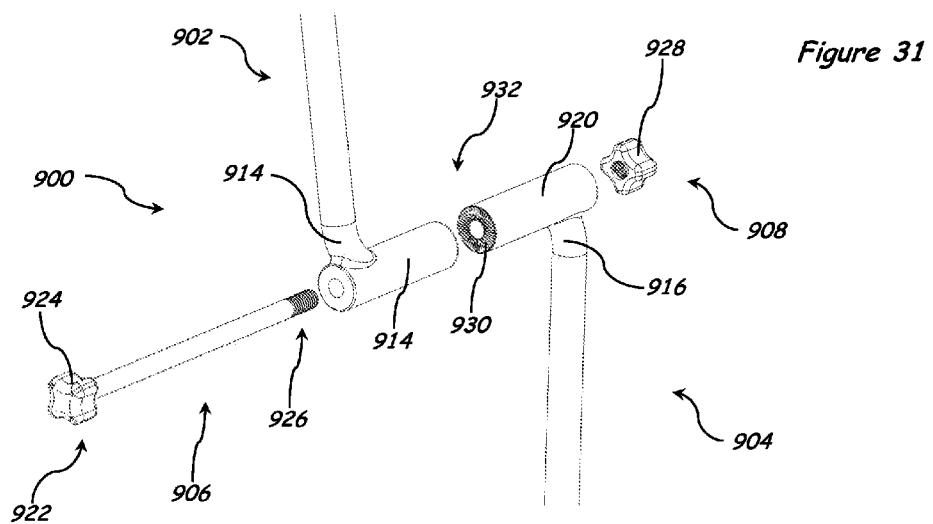
FIG. 31 is a detailed anterior-lateral exploded view of the second embodiment of the knee external fixator.
Figure 32:
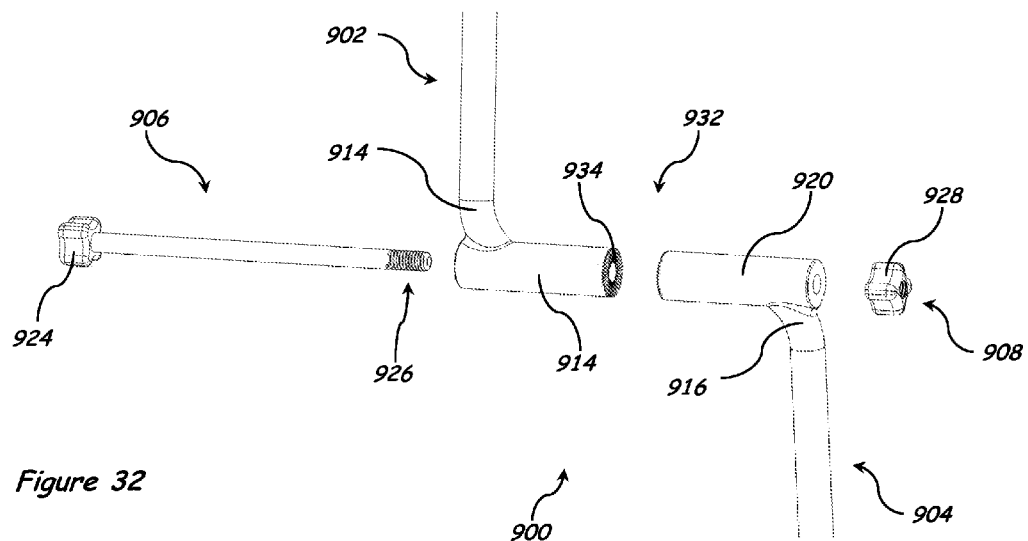
FIG. 32 is a detailed anterior-medial exploded view of the second embodiment of the knee external fixator.
Figure 33:
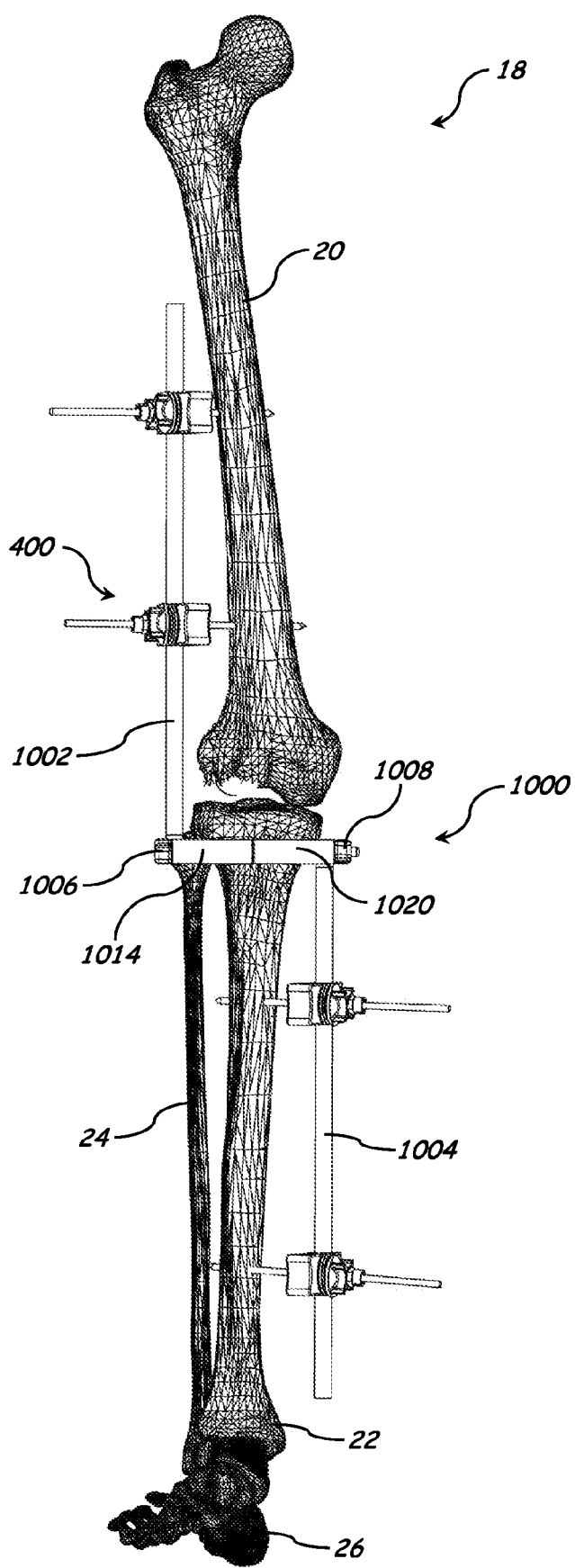
FIG. 33 is an anterior perspective view of a leg with a third embodiment of the knee external fixator and its associated clamps.
Figure 34:
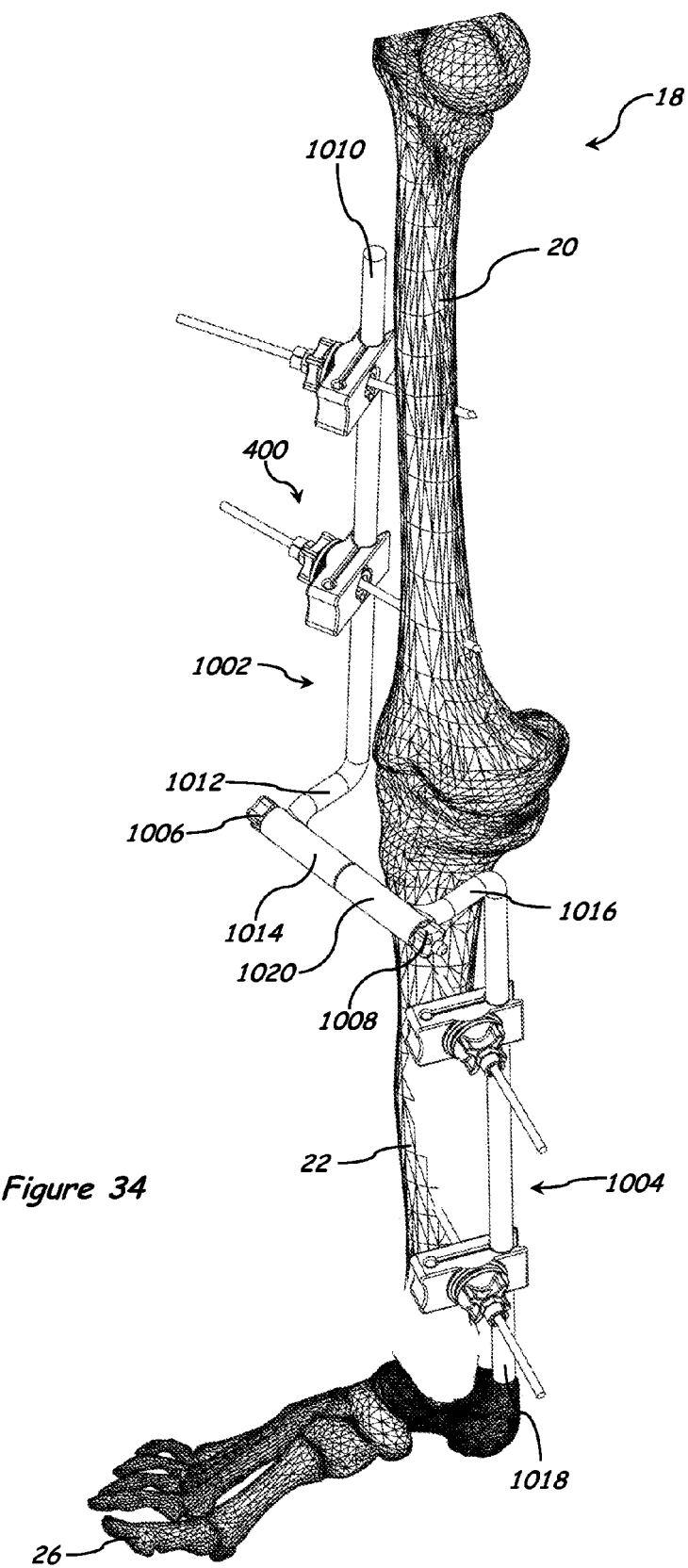
FIG. 34 is a superior-medial perspective view of a leg with the third embodiment of the knee external fixator and its associated clamps.
Figure 35:
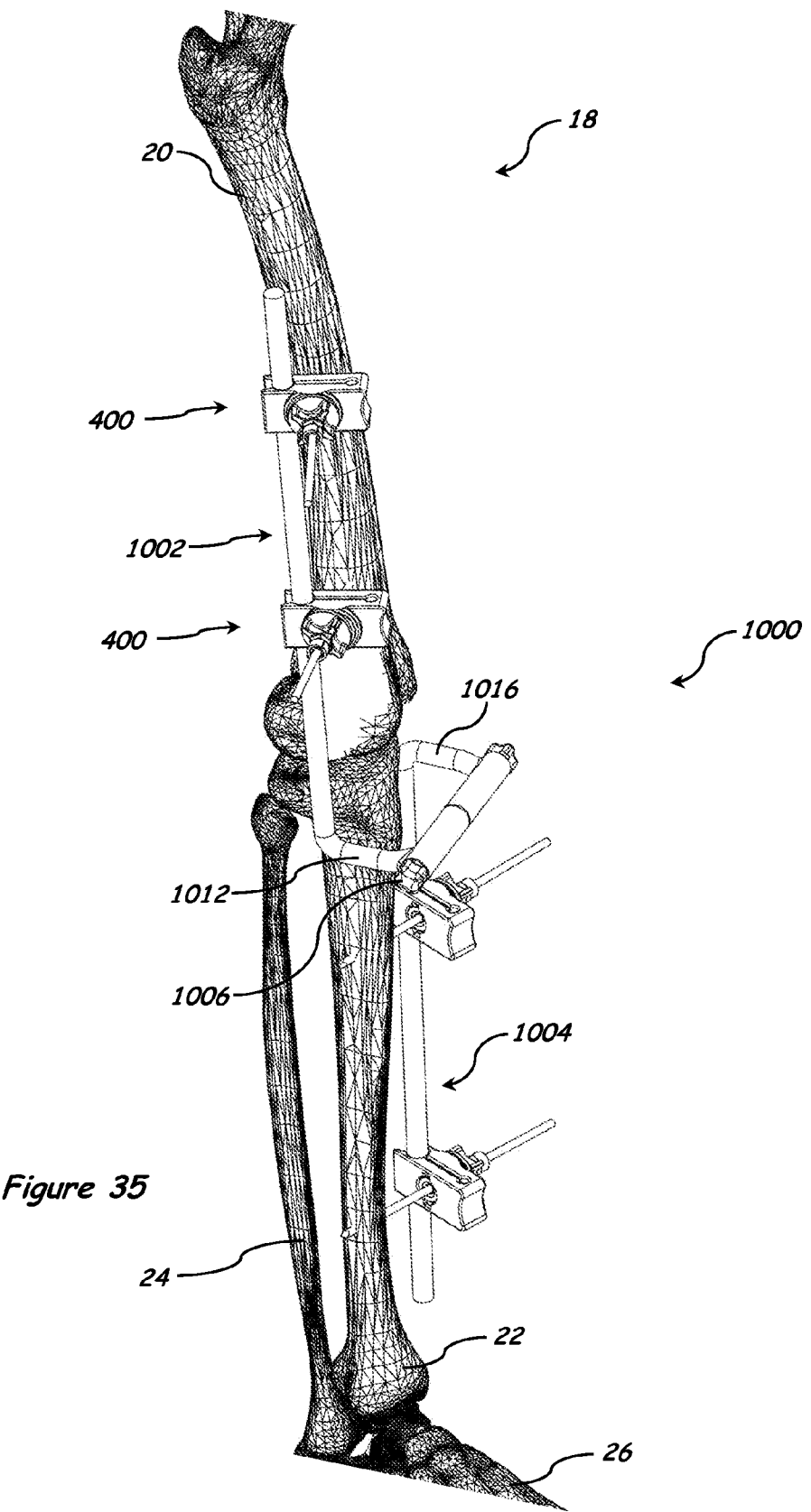
FIG. 35 is a superior-lateral perspective view of a leg with the third embodiment of the knee external fixator and its associated clamps.

Referring now to FIGS. 23-25, a first embodiment of an exemplary knee-spanning external fixation system 800 is illustrated mounted on a lower extremity 18 comprising a femur 20, tibia 22, fibula 24 and a foot 26.

FIGS. 23-27 illustrate a first embodiment of an exemplary knee-spanning external fixation system 800 comprising a first external fixation component 802, a second external fixation component 804, a first fastener 806, a second fastener 808, a closed-end clamp system 300 and an open-end clamp system 400. The first external fixation component 802 can be adapted to couple to the femur 20, the tibia 22, the fibula 24 and/or the foot 26 by use of the closed-end clamp system 300 and/or open-end clamp system 400. The second external fixation component 804 can be adapted to attach to the femur 20, the tibia 22, the fibula 24 and/or the foot 26 by use of the closed-end clamp system 300 and/or open-end clamp system 400.

The first external fixation component 802, second external fixation component 804, first fastener 806, second fastener 808, closed-end clamp system 300 and open-end clamp system 400 can be formed of any suitable material known to one skilled in the art that provides an adequate stiffness or resistance to torsion, stress, torque and/or other forces that may be applied to the system 800, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 800 in FIGS. 23-27, the first external fixation component 802 comprises a straight portion of cylindrical structure and a curved portion also of cylindrical structure, a first component proximal (e.g., first) end 810 and a first component distal (e.g., second) end 812 comprising the curved portion formed with a pivot structure of cylindrical body 814 having a through-bore bound by smooth walls extending along its pivot axis and further having a rough end surface 834. The first component proximal end 810 can be straight or curved. The second external fixation component 804 comprises a straight portion of cylindrical structure and a curved portion also of cylindrical structure, a second component distal (e.g., first) end 818 and a second component proximal (e.g., second) end 816 comprising the curved portion formed with a pivot structure of cylindrical body 820 having a through-bore bound by smooth walls extending along its pivot axis and a rough end surface 836. The second component distal end 818 can be straight or curved. The pivot structures 814 and 820 each has a length along the pivot axis such that when the two pivot structures 814 and 820 are joined end to end at their rough surfaces by a fastener, such as 806 or 808, the first external fixation component 802 and the second external fixation component 804 are disposed on different sides of the bone or knee (e.g., right side, left side, anterior, posterior). Each of the first and second external fixation components 802 and 804 including their respective pivot structures 814 and 820 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). A fastener 806 having threads 826 on its shaft is configured to extend through the through-bore in the cylindrical pivot structure 814 of the first external fixation component 802 and the through-bore in the cylindrical pivot structure 820 of the second external fixation component 804 and into a second fastener such as a threaded nut 808, and forms a threaded connection with the nut 808. The first external fixation component 802 and second external fixation component 804 are thus attached to each other via the coupling and interactions of the pivot structures 814 and 820 and the fasteners 806 and 808 to form a movable hinge or joint 838. This movable hinge or joint 838 is then locked in position by further tightening the fasteners 806 and 808 which interlocks the rough end surface 834 of the first external fixation component 802 with the rough end surface 836 of the second external fixation component 804. The fastener 806 can have a distal end or head 822 with irregularly shaped external geometry 824 to provide a secure gripping surface, and a shaft with engagement features such as threads 826 that can interface with the engagement features such as fins or threads inside the second fastener 808. Similarly, the second fastener 808 can also have an outer surface geometry for secure gripping surface.

FIGS. 28-32 illustrate an alternative embodiment 900 of the exemplary knee-spanning external fixation system 800 comprising a first external fixation component 902, a second external fixation component 904, a first fastener 906, a second fastener 908 and an open-end clamp system 400. The first external fixation component 902 can be adapted to attach to the femur 20, the tibia 22, the fibula 24 and/or the foot 26 by use of the closed-end clamp system 300 and/or open-end clamp system 400. The second external fixation component 904 can be adapted to attach to the femur 20, the tibia 22, the fibula 24 and/or the foot 26 by use of a closed-end clamp system 300 and/or open-end clamp system 400.

The exemplary knee-spanning external fixation system 900 is similar to the foregoing described system 800 except that the lockable and movable hinge of the knee-spanning external fixation system 900 is dimensioned to accommodate a wider joint or bone size. This is made possible by designing the pivot structures 914 and 920 to have a longer length along their mechanical pivot axis for accommodating a broader range of pin sites and/or body or joint sizes.

FIGS. 33-37 show a third embodiment of an exemplary knee-spanning external fixation system 1000 for mounting on a lower extremity 18 comprising a femur 20, tibia 22, fibula 24 and a foot 26.

The third embodiment of an exemplary knee-spanning external fixation system 1000 comprises a first external fixation component 1002, a second external fixation component 1004, a first fastener 1006, a second fastener 1008 and an open-end clamp system 400 or a close-end clamp system 300. The first external fixation component 1002 can be adapted to couple to the femur 20, the tibia 22, the fibula 24 and/or the foot 26 by use of the closed-end clamp system 300 and/or open-end clamp system 400. The second external fixation component 1004 can be adapted to couple to the femur 20, the tibia 22, the fibula 24 and/or the foot 26 by use of a closed-end clamp system 300 and/or open-end clamp system 400.

The first external fixation component 1002, second external fixation component 1004, first fastener 1006, second fastener 1008 and open-end clamp system 400 and optionally close-end clamp system 300 can be formed of any suitable material known to one skilled in the art that provides an adequate stiffness or resistance to torsion, stress, torque and/or other forces that may be applied to the system 1000, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 1000 in FIGS. 33-37, the first external fixation component 1002 having an "L" shape and a circular cross-sectional shape, comprises a first component proximal (e.g., first) end portion 1010 and a first component distal (e.g., second) end portion 1012. The first component distal end portion 1012 comprises the shorter leg of the "L" shape and is coupled to or formed at its open end a pivot structure of cylindrical body 1014 having a through-bore bound by smooth walls extending along its pivot axis and a rough end surface 1034. The first component distal end portion 1012 comprises a straight middle segment connecting two curved end segments. However, these segments can all be straight or curved. The first component proximal end 1010 can be straight or curved. The second external fixation component 1004 having an inverted "L" shape, comprises a second component proximal (e.g., second) end portion 1016 and a second component distal (e.g., second) end portion 1018. The second component proximal end portion 1016 comprises the shorter leg of the inverted "L" shape and is coupled to, or formed at, its open end a pivot structure of cylindrical body 1020 having a through-bore bound by smooth walls extending along its pivot axis and a rough end surface 1036. The second component proximal end portion 1016 comprises a straight middle segment connecting two curved end segments. However, these segments can all be straight or curved. The second component distal end portion 1018 can be straight or curved. The pivot structures 1014 and 1020 each has a length along the pivot axis such that when the two pivot structures 1014 and 1020 are joined end to end at their rough surfaces 1034 and 1036 by a fastener, the first external fixation component 1002 and the second external fixation component 1004 are disposed on different sides of the bone or knee (e.g., right side, left side, anterior, posterior). Each of the first and second external fixation components 1002 and 1004 including their respective pivot structures 1014 and 1020 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy).

A fastener 1006 having threads 1026 on its shaft is configured to extend through the through-bore in the cylindrical pivot structure 1014 of the first external fixation component 1002 and the through-bore in the cylindrical pivot structure 1020 of the second external fixation component 1004 and into a second fastener such as a threaded nut 1008, and forms a threaded connection with the nut 1008. The first external fixation component 1002 and second external fixation component 1004 are thus attached to each other via fasteners 1006 and 1008 to form a movable hinge or joint 1038. This movable hinge or joint 1038 is then locked in position by further tightening the fasteners 1006 and 1008 which interlocks the rough end surface 1034 of the pivot structure 1014 with the rough end surface 1036 of the pivot structure 1020. The fastener 1006 can have a distal end or head 1022 with irregularly shaped external geometry 1024 to provide a secure gripping surface, and a shaft with engagement features such as threads 1026 that can interface with the engagement features such as fins or threads inside the second fastener 1008. Similarly, the second fastener 1008 can also have an outer surface geometry for secure gripping surface.

In this exemplary embodiment, the first component distal end portion 1012 and the second component proximal end portion 1016 form a right angle with their respective first component proximal end portion 1010 and second component distal end portion 1018. One skilled in the art can select other angles such as 60 or 120 degrees to accommodate the type of fracture or body shape, for example. Other shapes and dimensions of the first and second external fixation components 1002 and 1004 also are within the spirit and scope of various embodiments of the present invention. Similarly, the angles (θ1, θ2) between the pivot structures 1014 and 1020 and their respective first component distal end portion 1012 and second component proximal end portion 1016 are 90 degrees as schematically illustrated in FIGS. 33-37, but angles other than 90 degrees are contemplated and within the spirit and scope of various embodiments of the present invention.

The first external fixation component 1002 and the second external fixation component 1004 including their respective pivot structures 1014 and 1020 can each be formed as a unitary modular structure or a modular structure. In the case of a unitary modular structure, for example, the first external fixation component 1002 can be formed from a single rod or bar and bent into the "L" shape, and welded to the pivot structure 1014. In the case of a modular structure, the first external fixation component 1002 and the pivot structure 1014 can be formed by removably connecting plurality of straight and/or curved rod segments and the pivot structure 1014 by snap-fitting, or threading, for example. The first and second external fixation components 1002 and 1004 and the pivot structures 1014 and 1020 can have any cross-sectional shapes (e.g. hexagonal, oval, square) and dimensions other than the circular cross-sectional shape as schematically illustrated in FIGS. 33-37.

Figure 38:
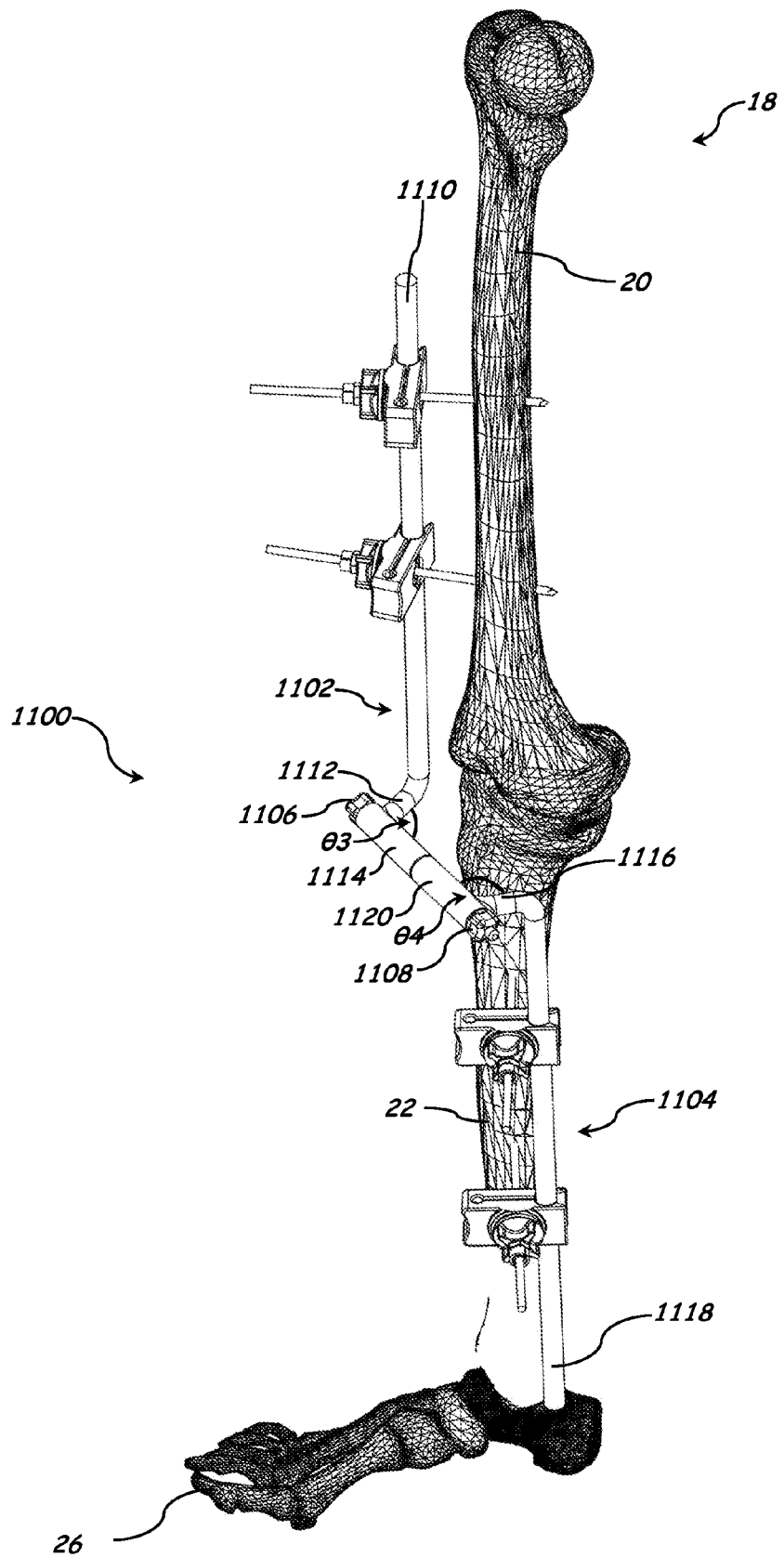
FIG. 38 is a superior-medial perspective view of a leg with a fourth embodiment of the knee external fixator and its associated clamps.
Figure 39:
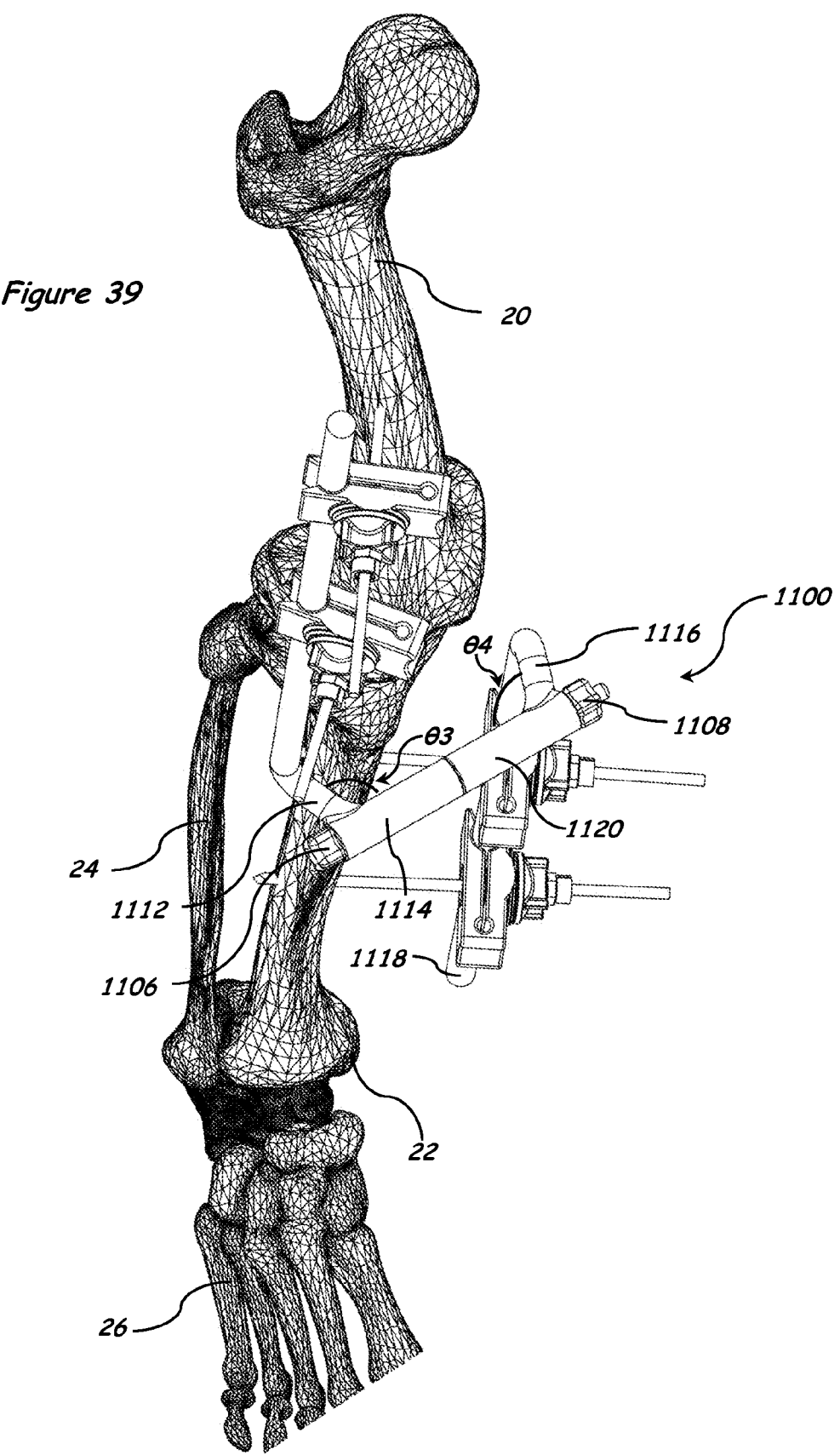
FIG. 39 is a superior-lateral perspective view of a leg with the fourth embodiment of the knee external fixator and its associated clamps.
Figure 40:
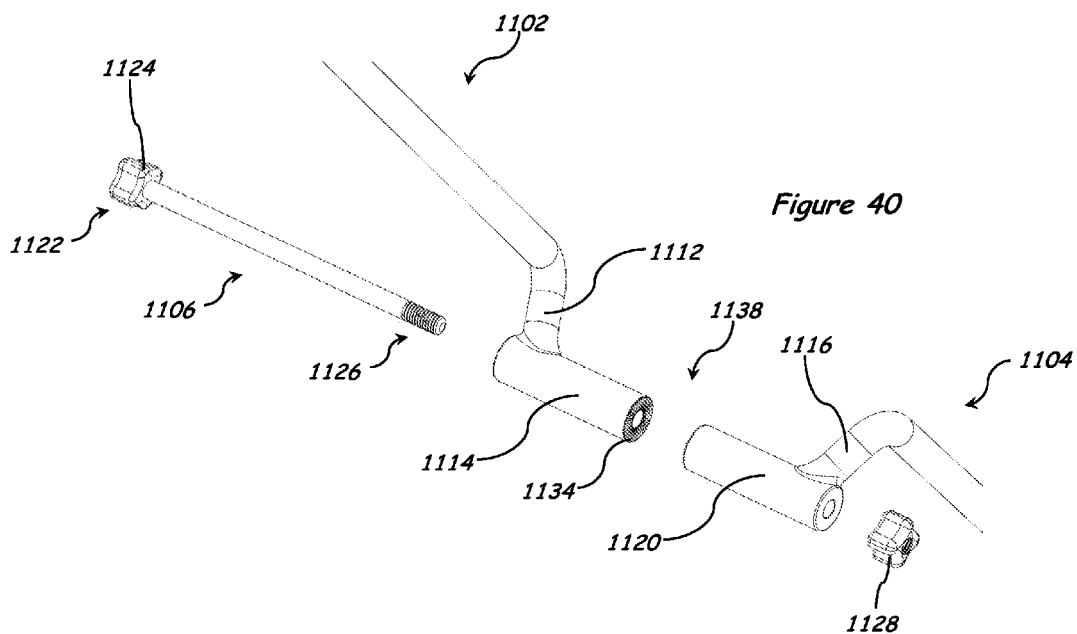
FIG. 40 is a detailed superior-medial exploded view of the fourth embodiment of the knee external fixator.
Figure 41:
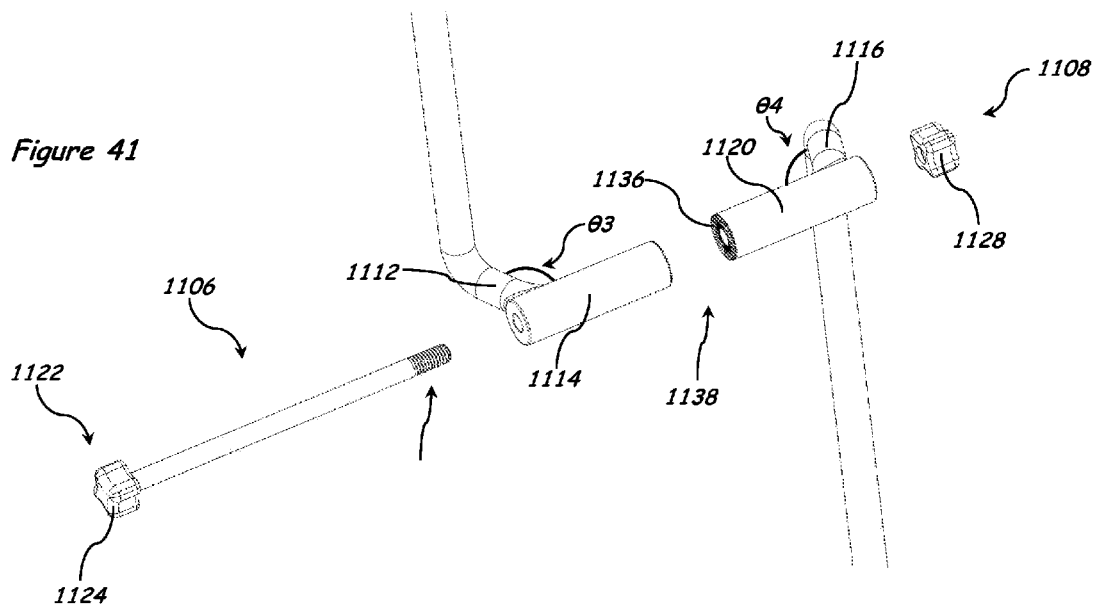
FIG. 41 is a detailed superior-lateral exploded view of the fourth embodiment of the knee external fixator.

Referring now to FIGS. 38-39, an alternative embodiment 1100 of the exemplary knee-spanning external fixation system 1000 is shown mounted by pins on the lower extremity 18 comprising a femur 20, tibia 22, fibula 24 and a foot 26.

The knee-spanning external fixation system 1100 illustrated in FIGS. 38-41 is similar to exemplary knee-spanning external fixation system 1000 in FIGS. 33-37 except that the first component distal (e.g., first) end 1112 and the second component proximal (e.g., second) end 1116 are each connected to their respective pivot structures 1114 and 1120 at an angle greater than 90 degrees (θ3, θ4).

FIGS. 42-69 show various exemplary ankle-spanning external fixation systems, some are of unitary, prefabricated modular construction (e.g. from multiple pieces welded together), or unitary construction (e.g. from a single piece of material by molding), while others are of modular construction (e.g. multiple pieces removably threaded together to allow surgeons to use the assembled system as is or to reconfigure the assembled system to match the patient anatomy). The illustrated ankle-spanning external fixation systems comprise a proximal or upper frame coupled to a distal or lower frame such as the curved foot frame including a posterior frame segment extending angularly from and above an inferior frame segment designed for placement and use substantially adjacent to the ankle area of the body to protect both the posterior and the inferior of a foot or ankle while healing is taken place. The system can be used adjacent to other joints such as the elbow or the knee, and is capable of being any shape and size that allows for support of the joint and area round the joint such as the foot, ankle, and/or lower extremity.

Figure 42:
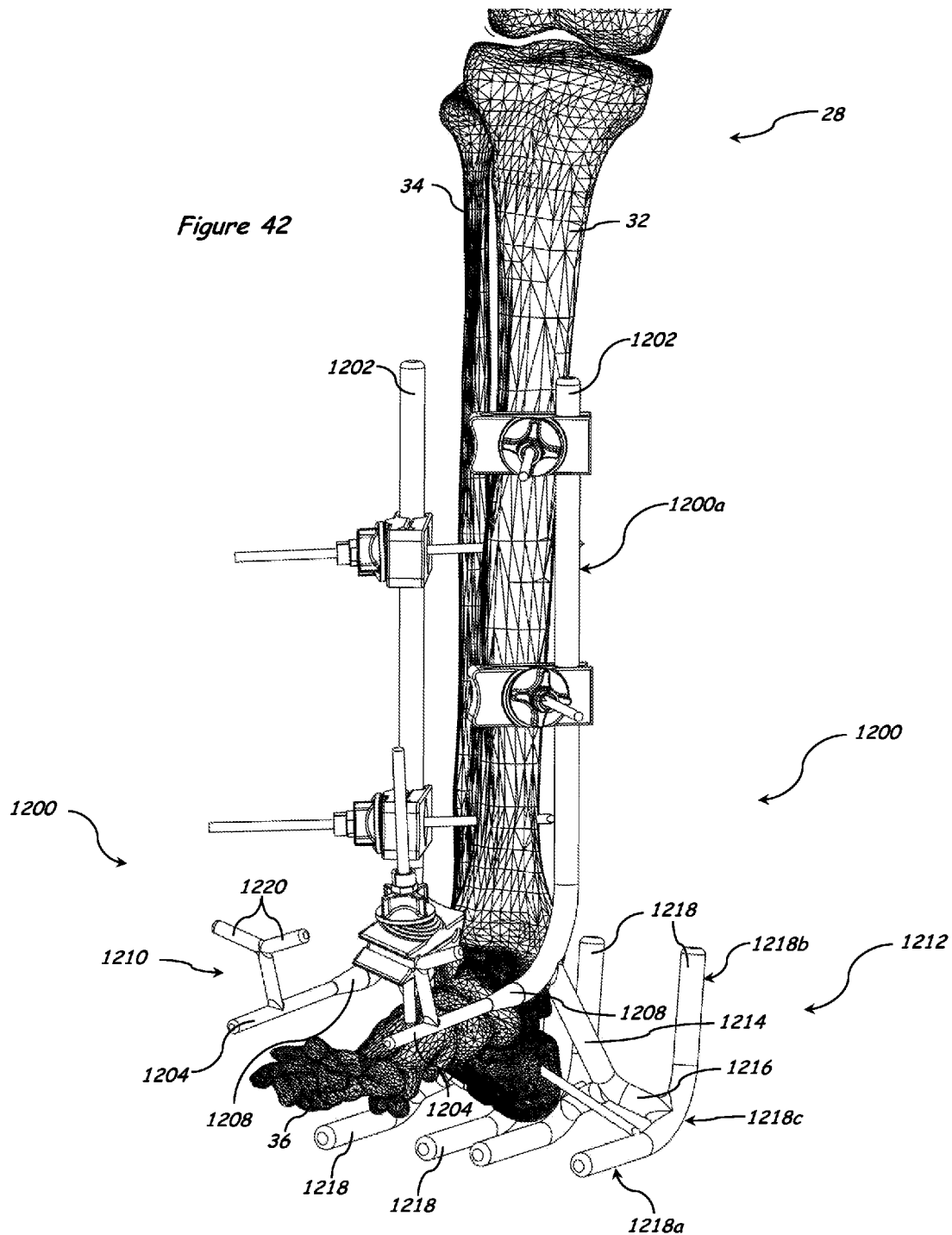
FIG. 42 is an anterior-medial perspective view of a leg with a first embodiment of the ankle external fixator and its associated clamps.
Figure 43:
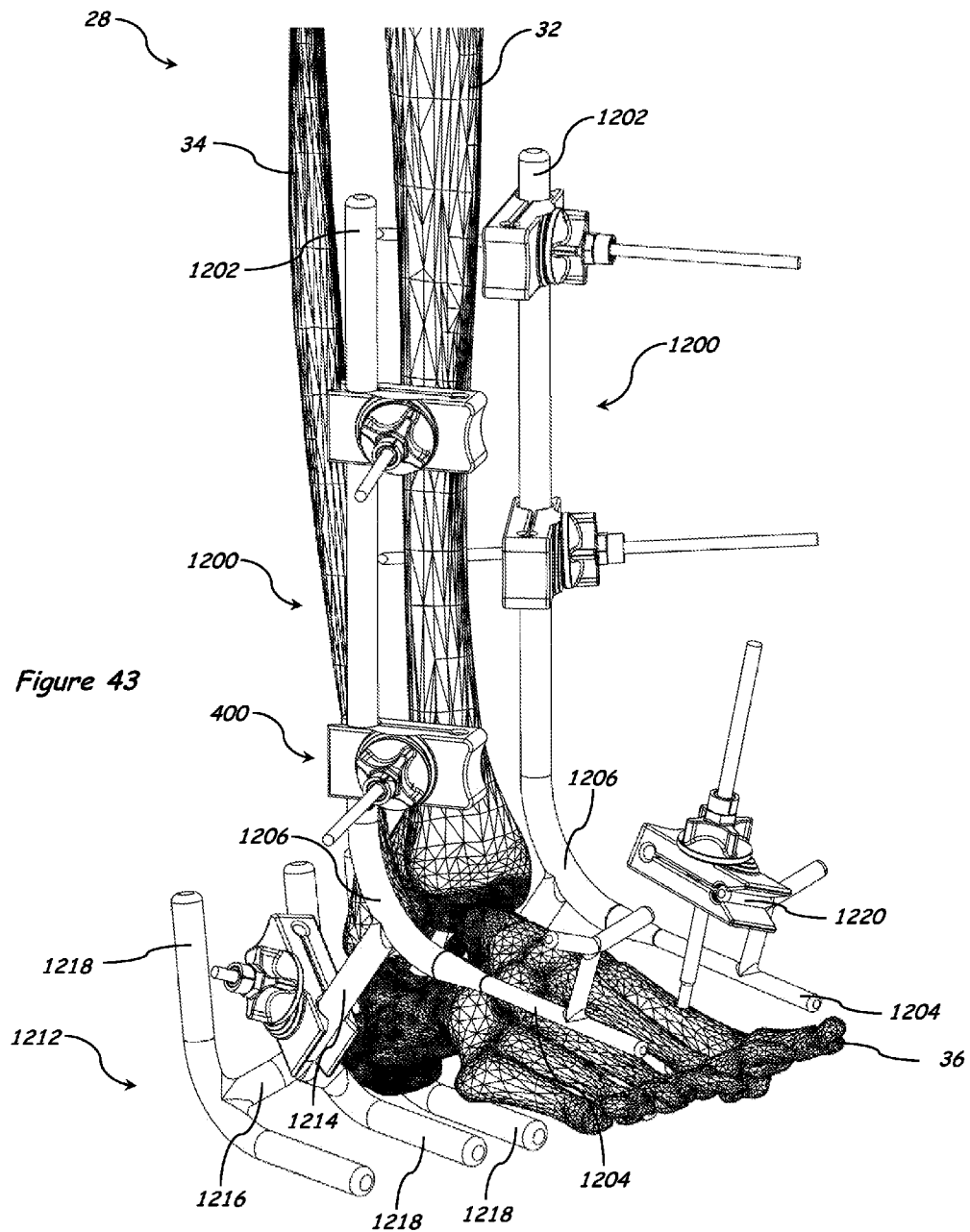
FIG. 43 is an anterior-lateral perspective view of a leg with the first embodiment of the ankle external fixator and its associated clamps.
Figure 44:
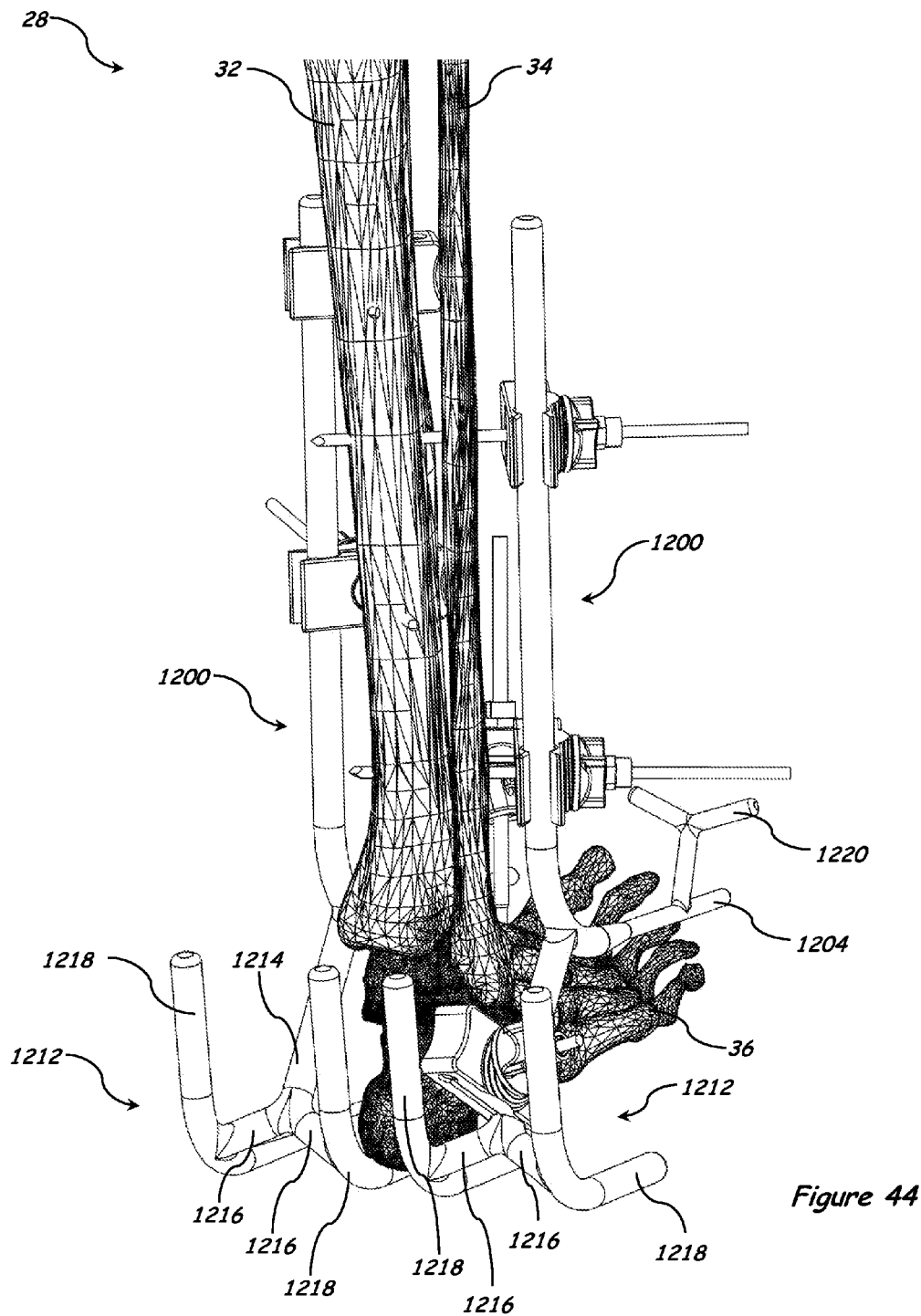
FIG. 44 is a posterior-lateral perspective view of a leg with the first embodiment of the ankle external fixator and its associated clamps.

Referring now to FIGS. 42-44, a first embodiment of an exemplary ankle-spanning external fixation system 1200 is shown mounted via pins on an exemplary lower extremity 28 comprising a tibia 32, fibula 34 and a foot 36. The fixation system 1200 includes one or more open-end clamps 400 and 1300 and optionally closed-end clamps for clamping fixation elements such as bars, rods, pins, or wires of various diameters.

The external fixation system 1200 and open-end clamp systems 400 and 1300 can be formed of any suitable material known to one skilled in the art that provides an adequate stiffness or resistance to torsion, stress, torque and/or other forces that may be applied to the system 1200, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form the system 1200 of aluminum, stainless steel and/or carbon fiber, at least because these materials have properties that are well suited to external fixation of fractures.

The illustrated embodiment 1200 in FIGS. 42-44 comprises two ankle-spanning external fixation systems 1200 which are substantially the same and mounted on each side of the foot to protect the ankle and area around the ankle. Each external fixation system 1200 comprises a single piece, unitary prefabricated modular frame comprising a proximal (e.g., first) frame 1200a, a connector 1214 and 1216 and a distal (e.g., second) frame 1212 attached together by standard means, such as welding, soldering, brazing, crimping, or adhesives. The proximal frame defines a single bar or rod such as bar 1200a including a proximal (e.g., first) end portion 1202 and a distal (e.g., second) end portion 1204 and a curved portion 1206 connecting the proximal and distal end portions 1202 and 1204. The distal end 1204 can be of a reduced diameter 1208 and comprises an extension or outrigger 1210 which can be divided into two or more branches, such as bifurcation 1220, for attaching a clamp such as the open-end clamp system 300 or closed-end clamp system 400. A distal frame, such as the foot frame 1212, configured to capture the posterior and the inferior aspects of a joint, such as the ankle, comprising two parallel curved rods 1218, is coupled to the proximal frame, such as the bar 1200a, via a Y-shaped connector having two arms 1216 and a trunk 1214. Other shapes of the connector also are within the spirit and scope of various embodiments of the present invention. Each curved rod 1218 comprises a straight inferior (e.g., first) frame section or portion 1218a and a straight posterior (e.g., second) frame section or portion 1218b and a curved frame section or portion 1218c connecting the straight inferior frame section 1218a to the straight posterior frame section 1218b, wherein said inferior frame portion 1218a and said posterior frame portion 1218b are operatively disposed in at least partially surrounding and spatial relation to the ankle or the heel of the foot 36, wherein said posterior frame portion 1218b extends angularly from and above said inferior frame portion 1218a. Each arm 1216 of the Y-shaped connector connects to one of the rods 1218 of the foot frame 1212 at the concave surface side of the curved frame section, and the trunk 1214 of the Y-shaped connector connects to the curved portion 1206 of the proximal frame such as the bar frame 1200a at the convex surface side of the curved portion 1206.

The foot frame 1212 is generally configured to capture the posterior and the inferior aspects of a foot or ankle and thus may take various shapes as illustrated in other exemplary embodiments. In the single piece, unitary modular construction, the proximal and distal frames 1200a and 1212 and connector(s) 1214 and 1216 and their subcomponents such as outrigger 1220 can be welded, soldered, crimped, brazed or glued/epoxied together during manufacturing. Alternatively, in a unitary construction, the proximal frame 1200a, the connector 1214 and 1216 and the distal frame 1212 and optionally any subcomponents such as an outrigger 1220 may be integral-machined or formed from a single piece of metal or other material by standard means such as molding or machining. In a multi-piece, or modular construction, the proximal and distal frames 1200a and 1212 and connector 1214 and 1216 and their subcomponents 1220 can be removably connected by standard means such as threads, plug-socket joint, snap-fit, interference fit or a combination thereof during manufacturing or immediately prior to use to provide surgeons the flexibility of design choices to fit the patient anatomy. The proximal and distal end portions 1202 and 1204 of the bar frame 1200a and the Y-shaped connector may be formed of various curved and/or straight pieces or subcomponents connected together and may have any profiles. The components of the system 1200 are shown as having circular cross-sectional shape. Other cross-sectional shapes such as hexagonal shape, square, rectangle, for example, are within the spirit and scope of the various embodiments of the present invention.

Figure 45:
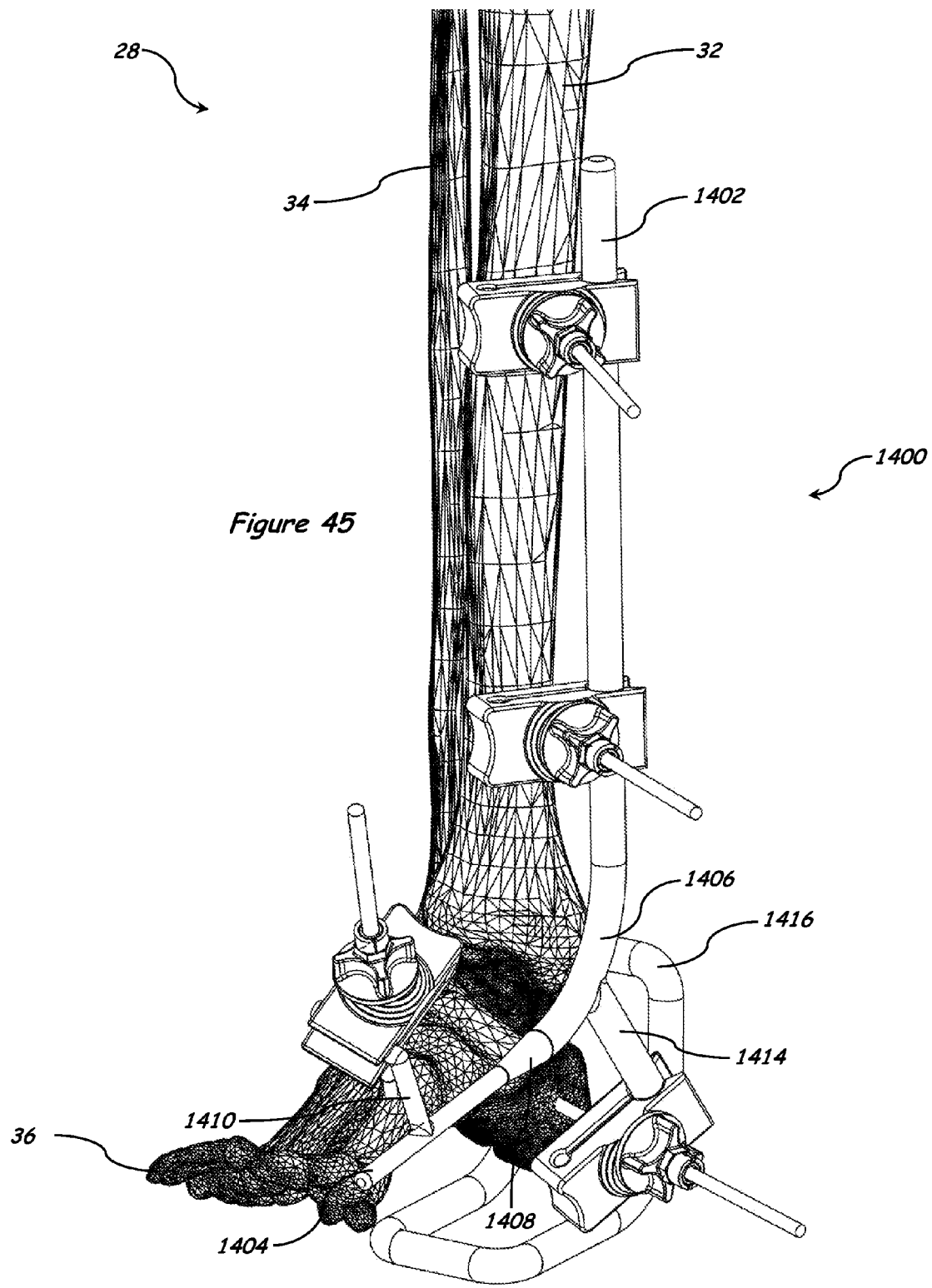
FIG. 45 is an anterior-medial perspective view of a leg with a second embodiment of the ankle external fixator and its associated clamps.
Figure 46:
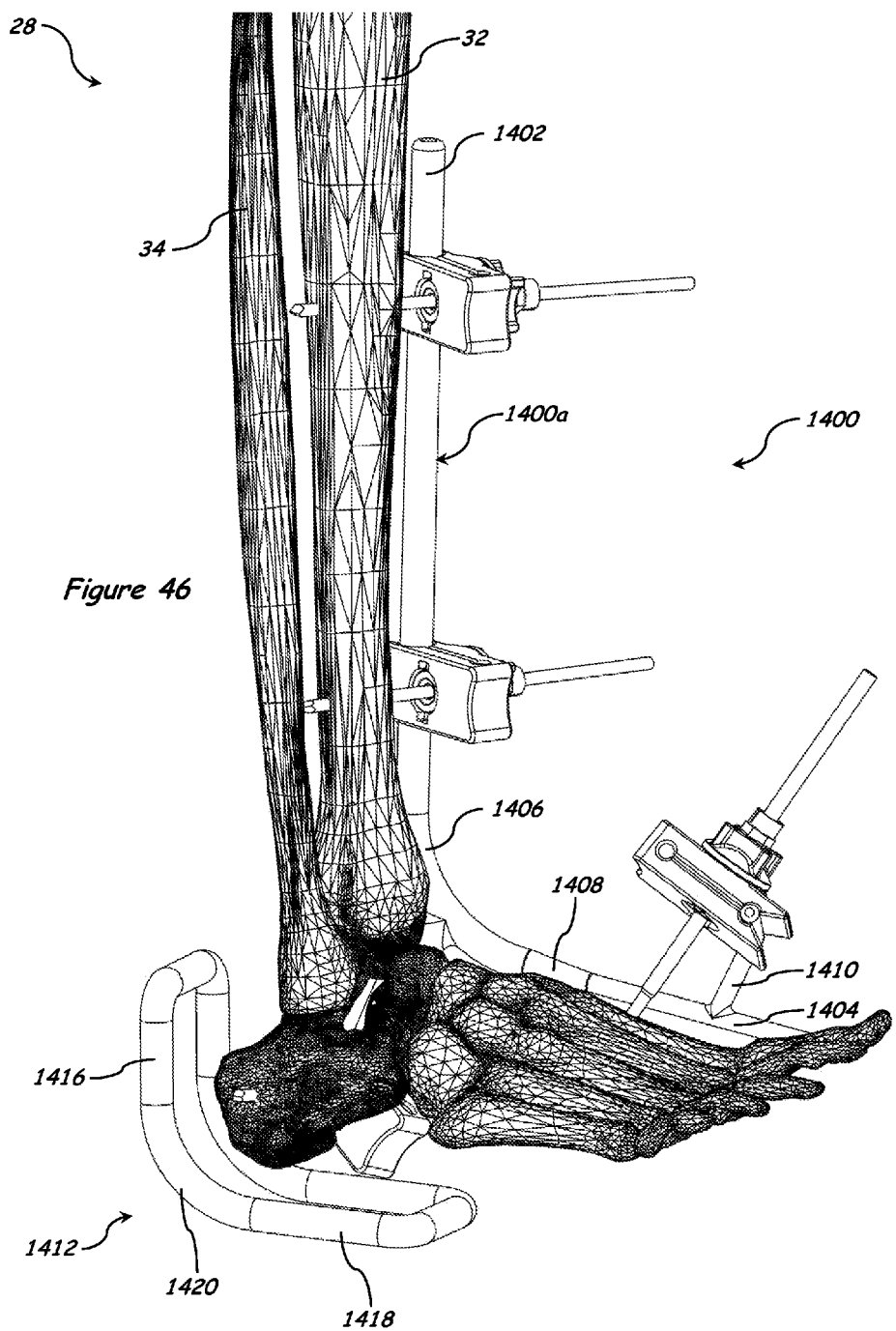
FIG. 46 is an anterior-lateral perspective view of a leg with the second embodiment of the ankle external fixator and its associated clamps.
Figure 47:
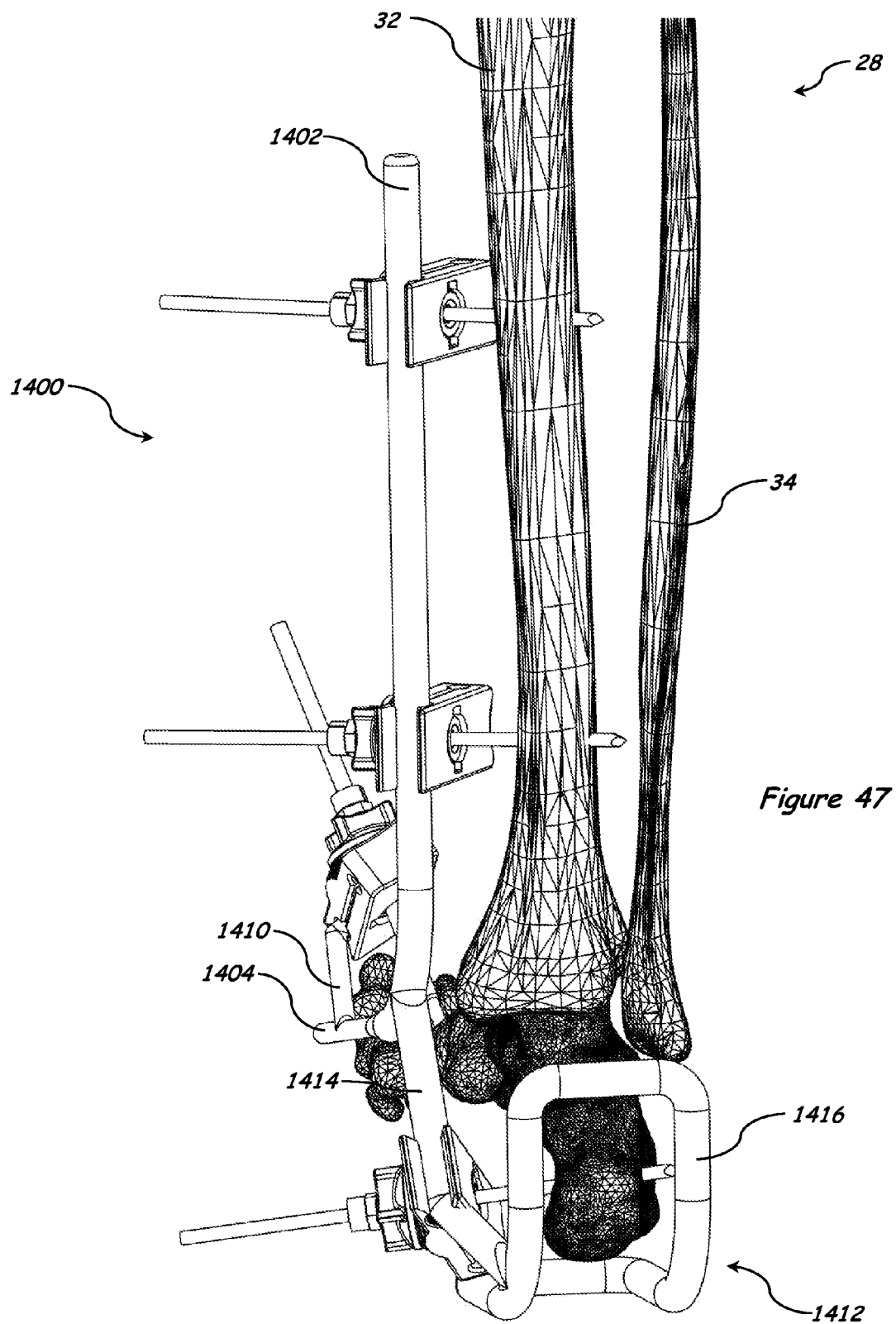
FIG. 47 is a posterior-medial perspective view of a leg with the second embodiment of the ankle external fixator and its associated clamps.

Referring now to FIGS. 45-47, an alternative embodiment 1400 of the exemplary ankle-spanning external fixation system 1200 is shown mounted by pins on the lower extremity 28 comprising a femur 30, tibia 32, fibula 34 and a foot 36, wherein the foot frame is of a different design.

The exemplary ankle-spanning external fixation system 1400 comprises a single piece, unitary prefabricated modular frame comprising a proximal (e.g., first) frame 1400a, a connector 1414 and a distal (e.g., second) frame 1412 attached together by standard means such as welding, soldering, brazing, crimping, or adhesives. Alternatively, the proximal frame, the connector and the distal frame may be integral-machined or formed from a single piece of metal or other material by standard means such as molding or machining. The exemplary ankle-spanning external fixation system 1400 comprises a proximal frame such as bar frame 1400a coupled to a distal frame such as a foot frame 1412 via a frame connector 1414 wherein the foot frame comprises a continuous elongated ring frame having a U-shaped inferior (e.g., first) frame section 1418 lying in a first plane and a U-shaped posterior (e.g., second) frame section 1416 lying in a second plane and a curved section 1420 connecting each of the legs of the U-shape inferior frame section 1418 to each of those of the U-shaped posterior frame section 1416 to form a closed loop. Other shapes of the inferior and posterior frame portions are also within the spirit and scope of various embodiments of the present invention. The first and second planes containing the inferior frame section 1418 and the posterior frame section 1416 are perpendicular to each other as schematically illustrated. However, the angle between the first and second planes can be other than 90 degrees, such as 60 degrees or 120 degrees. Said inferior frame portion 1418 and said posterior frame portion 1416 are operatively disposed in at least partially surrounding and spatial relation to the ankle or the heel of the foot 36, wherein said posterior frame portion 1416 extends angularly from and above said inferior frame portion 1418. In the single piece, unitary modular construction, the proximal and distal frames 1400*a* and 1412 and connector(s) 1414 and their subcomponents such as outrigger 1410 can be welded, soldered, crimped, brazed or glued/epoxied together during manufacturing. Alternatively, in a unitary construction, the proximal frame 1400*a*, the connector 1414 and the distal frame 1412 and optionally any subcomponents such as an outrigger 1410 may be integral-machined or formed from a single piece of metal or other material by standard means such as molding or machining. In a multi-piece, or modular construction, the proximal and distal frames 1400*a* and 1412 and connector 1414 and their subcomponents 1410 can be removably connected by standard means, such as threads, plug-socket joint, snap-fit, interference fit or a combination thereof during manufacturing or immediately prior to use to provide surgeons the flexibility of design choices to fit the patient anatomy. All the components of the frames and the frame connector can have circular cross-sectional shape as shown or can have other cross-sectional shape including square, oval, hexagon, or others. Each of the proximal and distal frames can be made from a single rod/bar or a plurality of straight and/or curved bar/rod segments or subcomponents connected together end-to-end using welding, soldering, gluing, brazing, crimping, threading, snap-fitting or the like.

Figure 48:
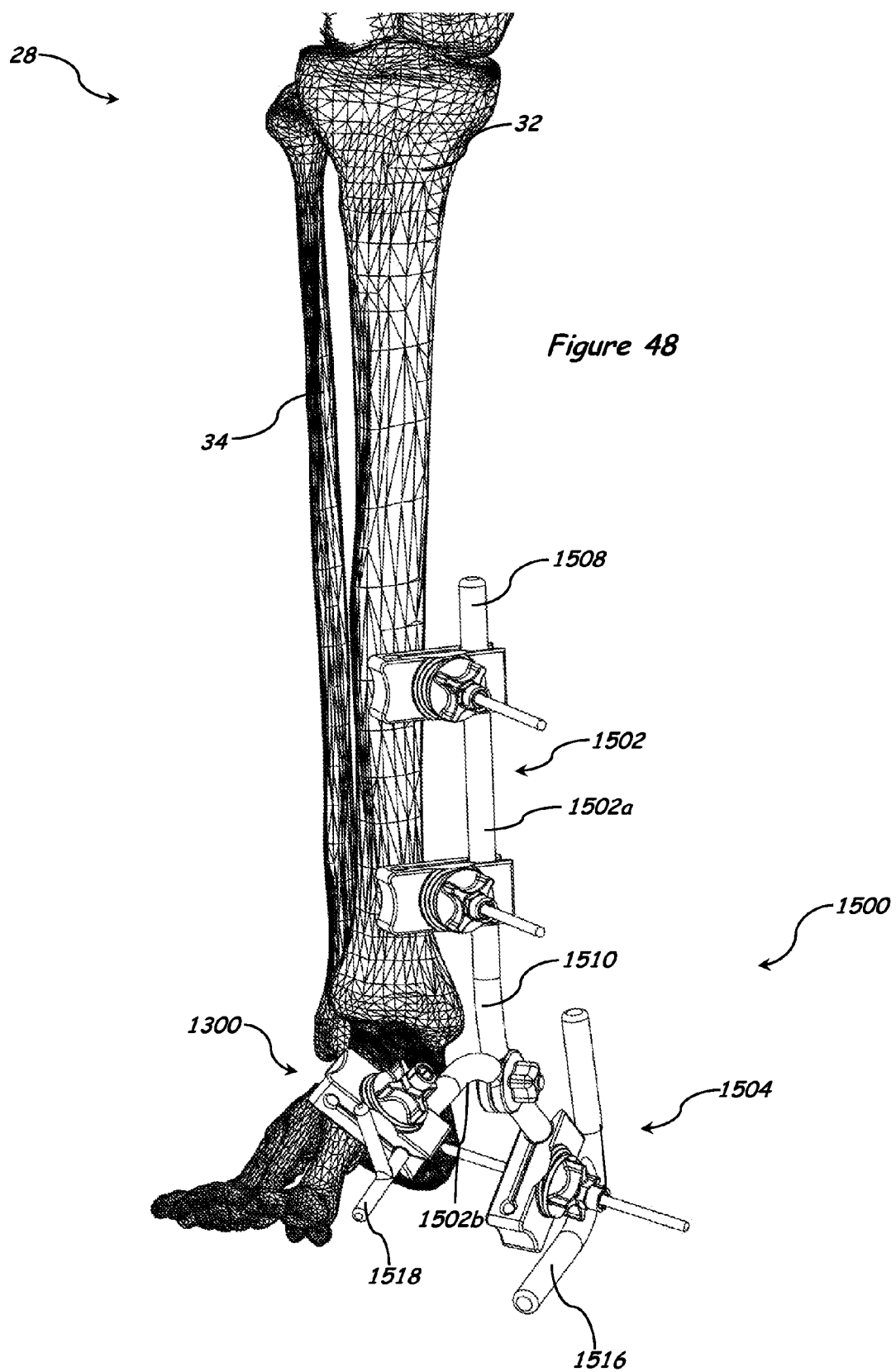
FIG. 48 is an anterior-medial perspective view of a leg with a third embodiment of the ankle external fixator and its associated clamps.
Figure 49:
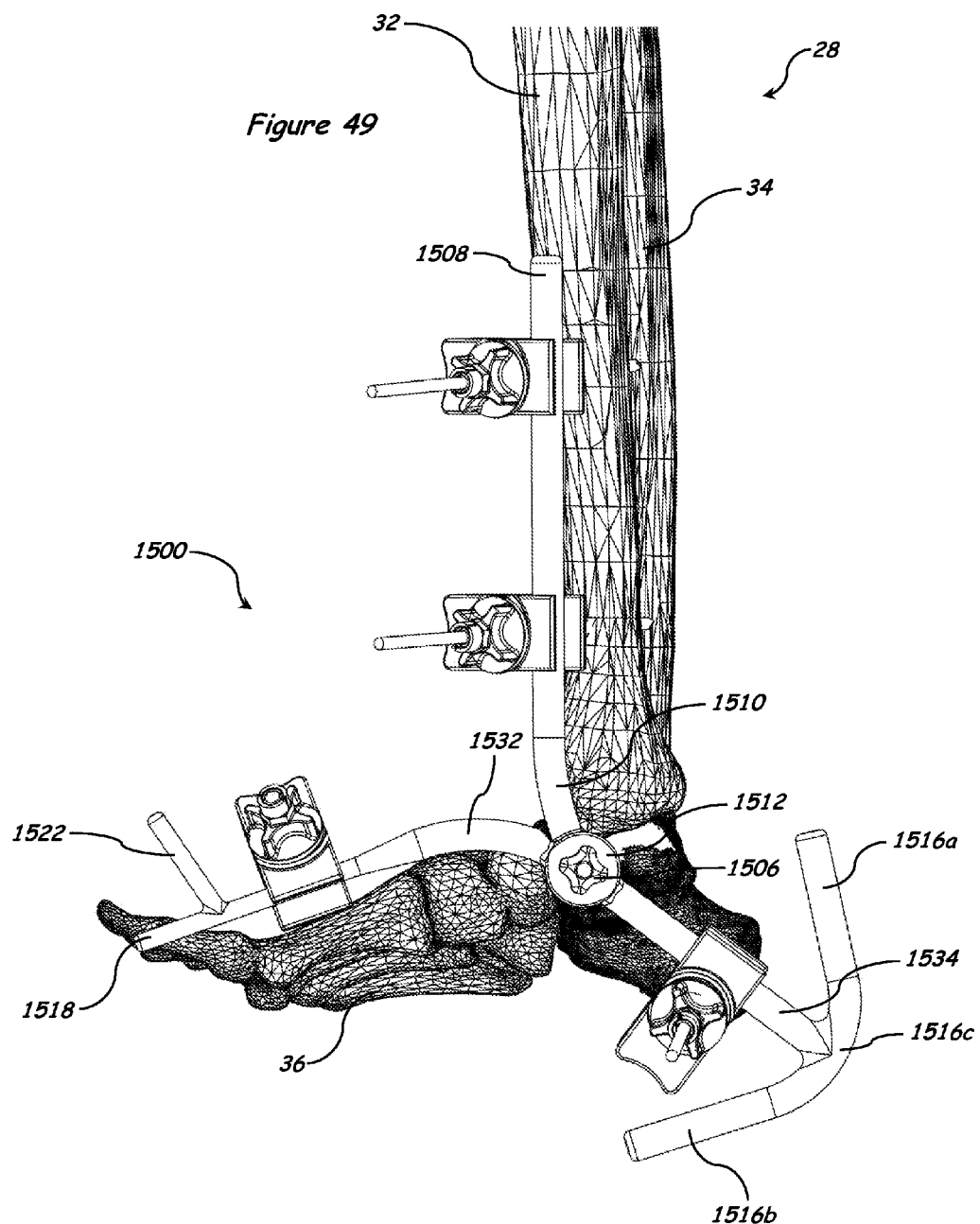
FIG. 49 is a medial perspective view of a leg with the third embodiment of the ankle external fixator and its associated clamps.
Figure 50:
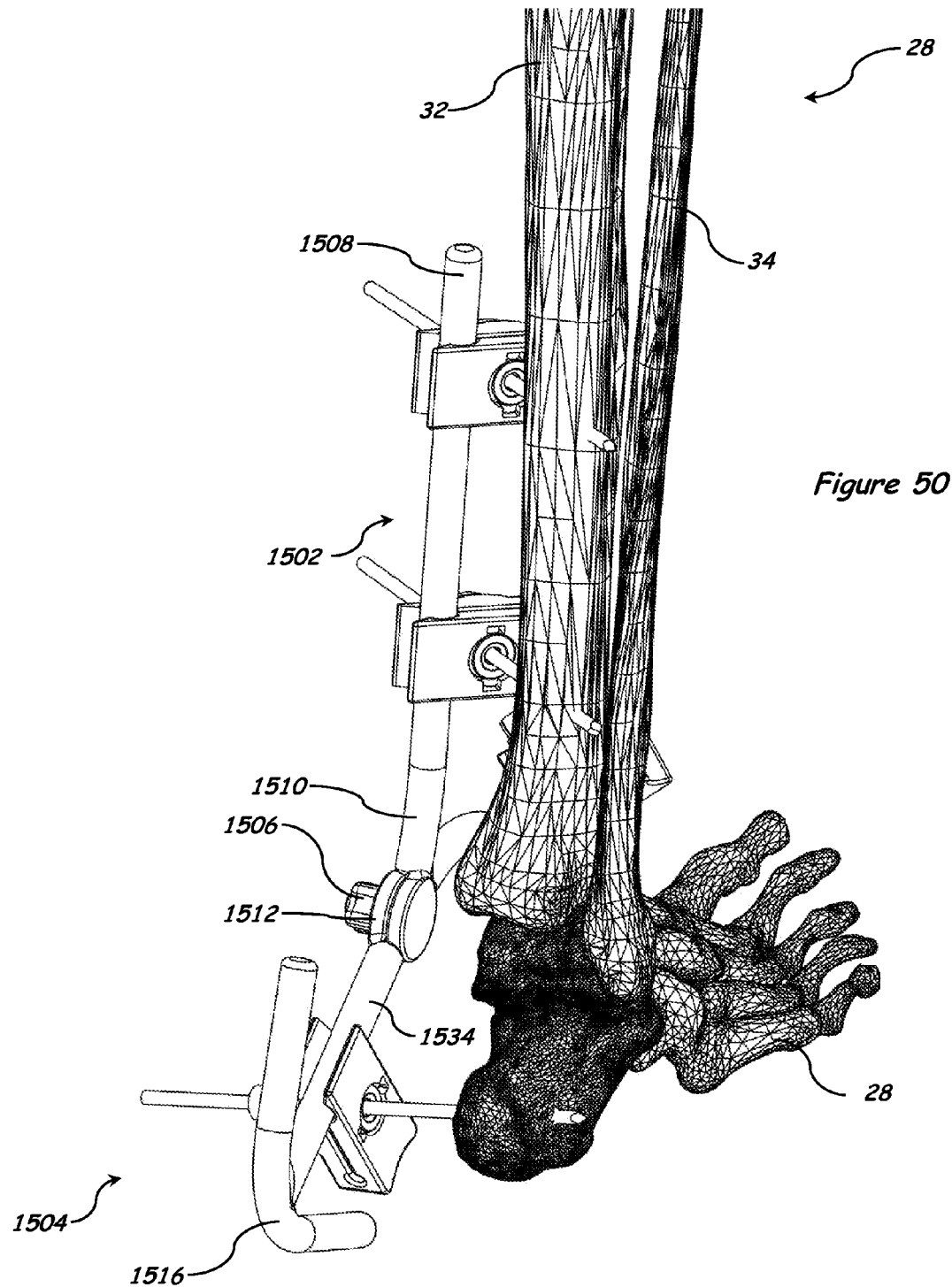
FIG. 50 is a posterior-lateral perspective view of a leg with the third embodiment of the ankle external fixator and its associated clamps.
Figure 51:
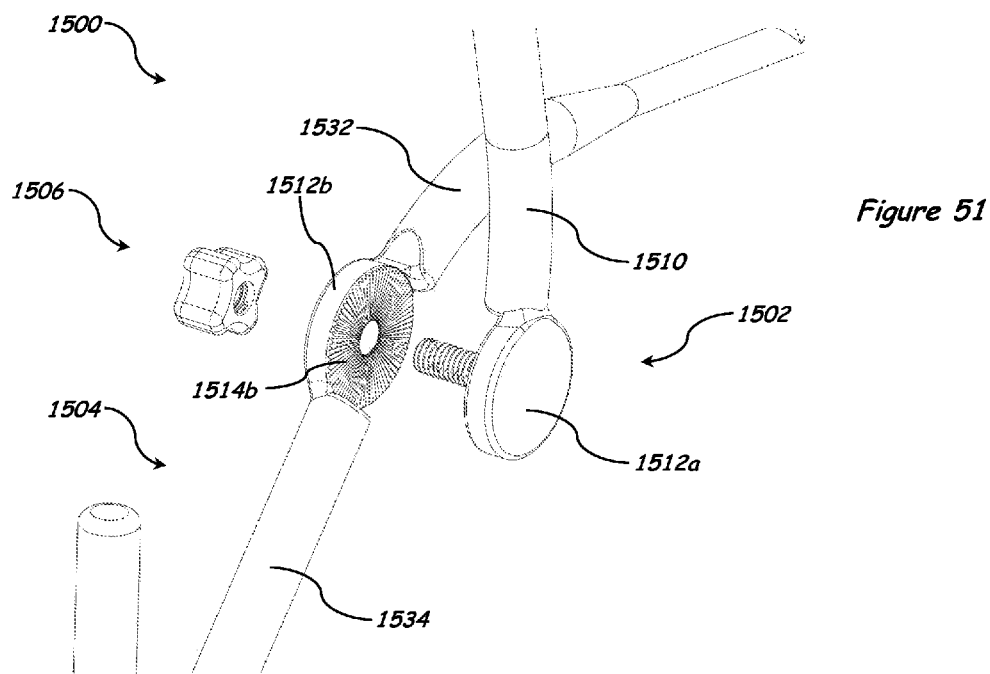
FIG. 51 is a detailed posterior-lateral exploded view of the third embodiment of the ankle external fixator.
Figure 52:
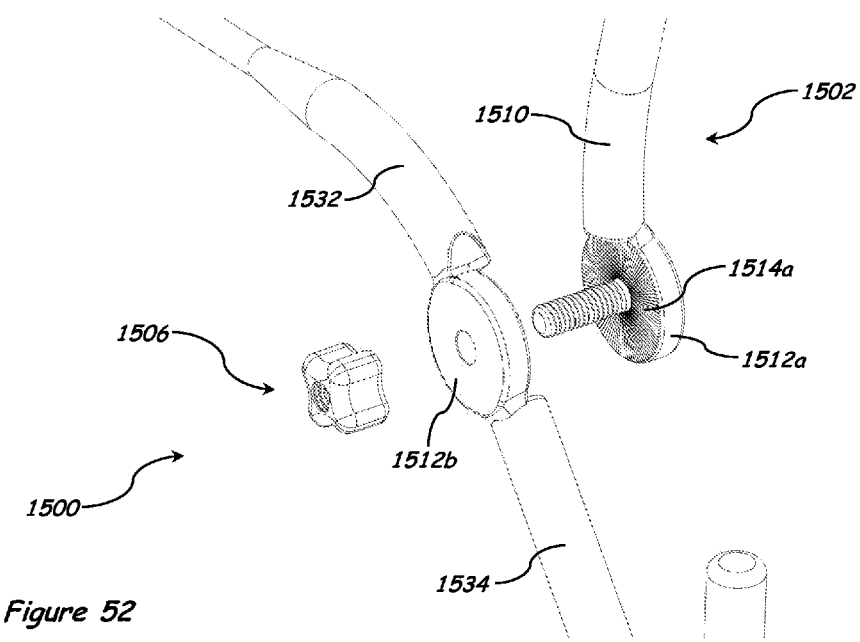
FIG. 52 is a detailed posterior-medial exploded view of the third embodiment of the ankle external fixator.
Figure 53:
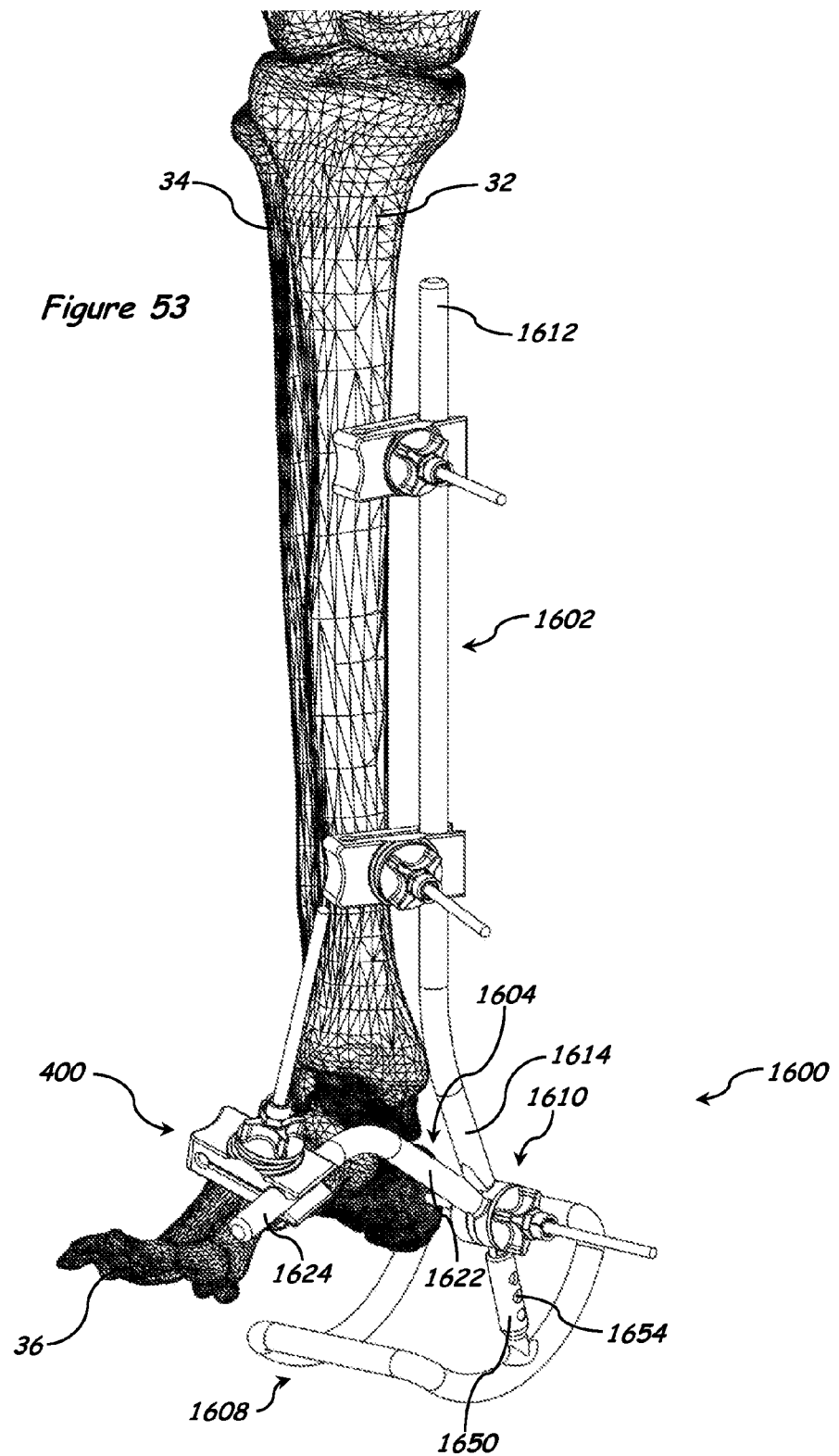
FIG. 53 is an anterior-medial perspective view of a leg with a fourth embodiment of the ankle external fixator and its associated clamps.
Figure 54:
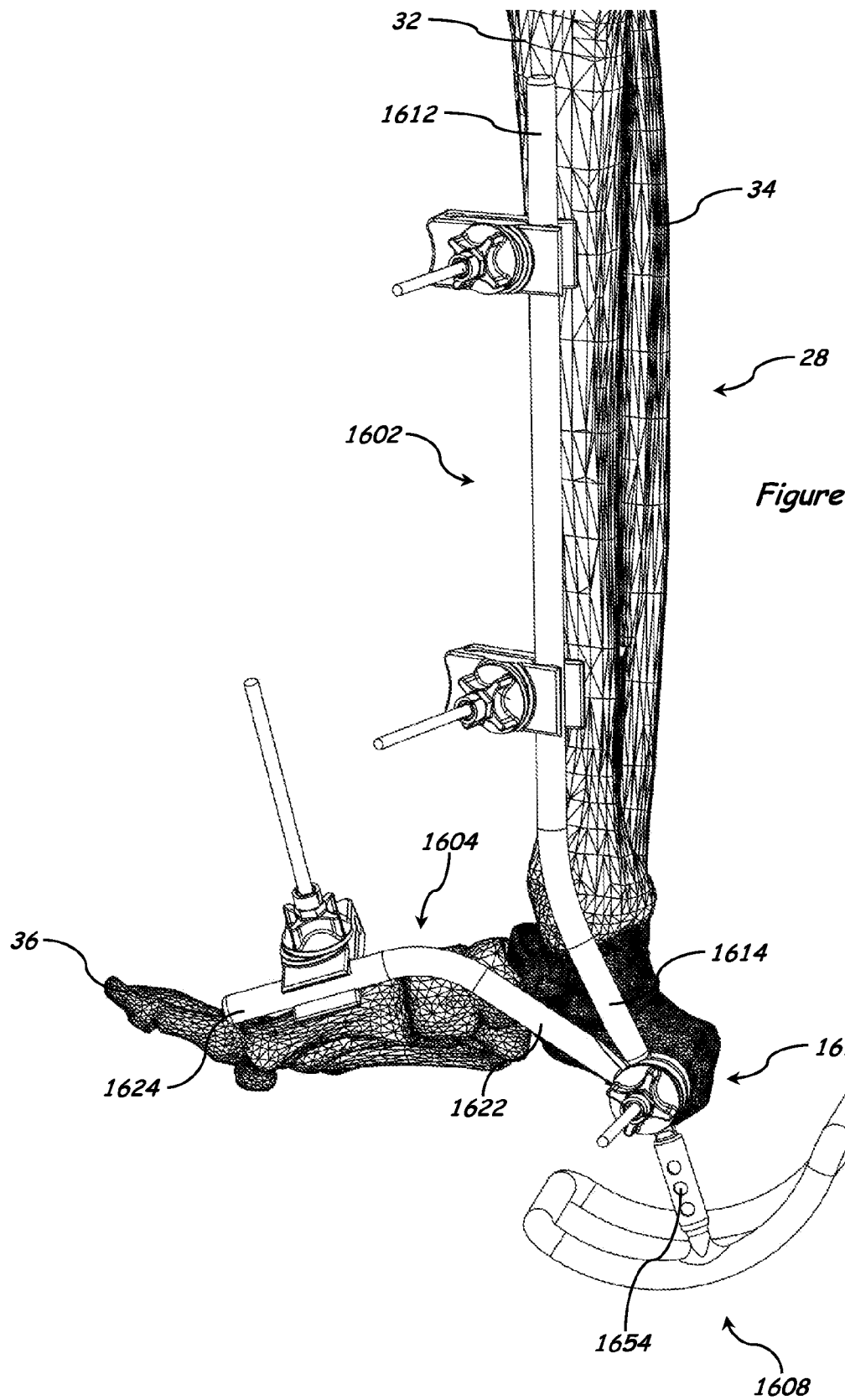
FIG. 54 is a medial perspective view of a leg with the fourth embodiment of the ankle external fixator and its associated clamps.
Figure 55:
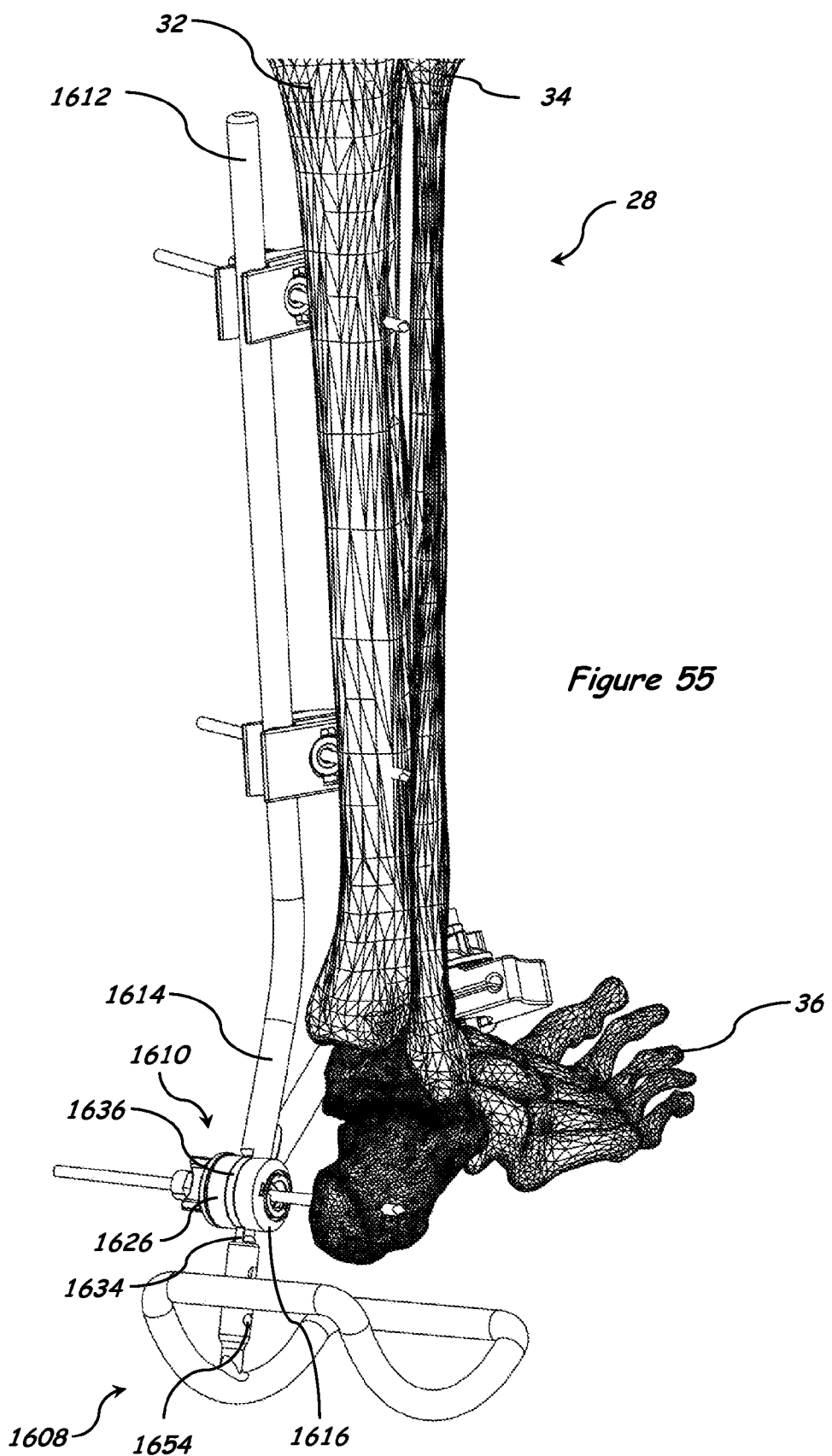
FIG. 55 is a posterior-lateral perspective view of a leg with the fourth embodiment of the ankle external fixator and its associated clamps.
Figure 56:
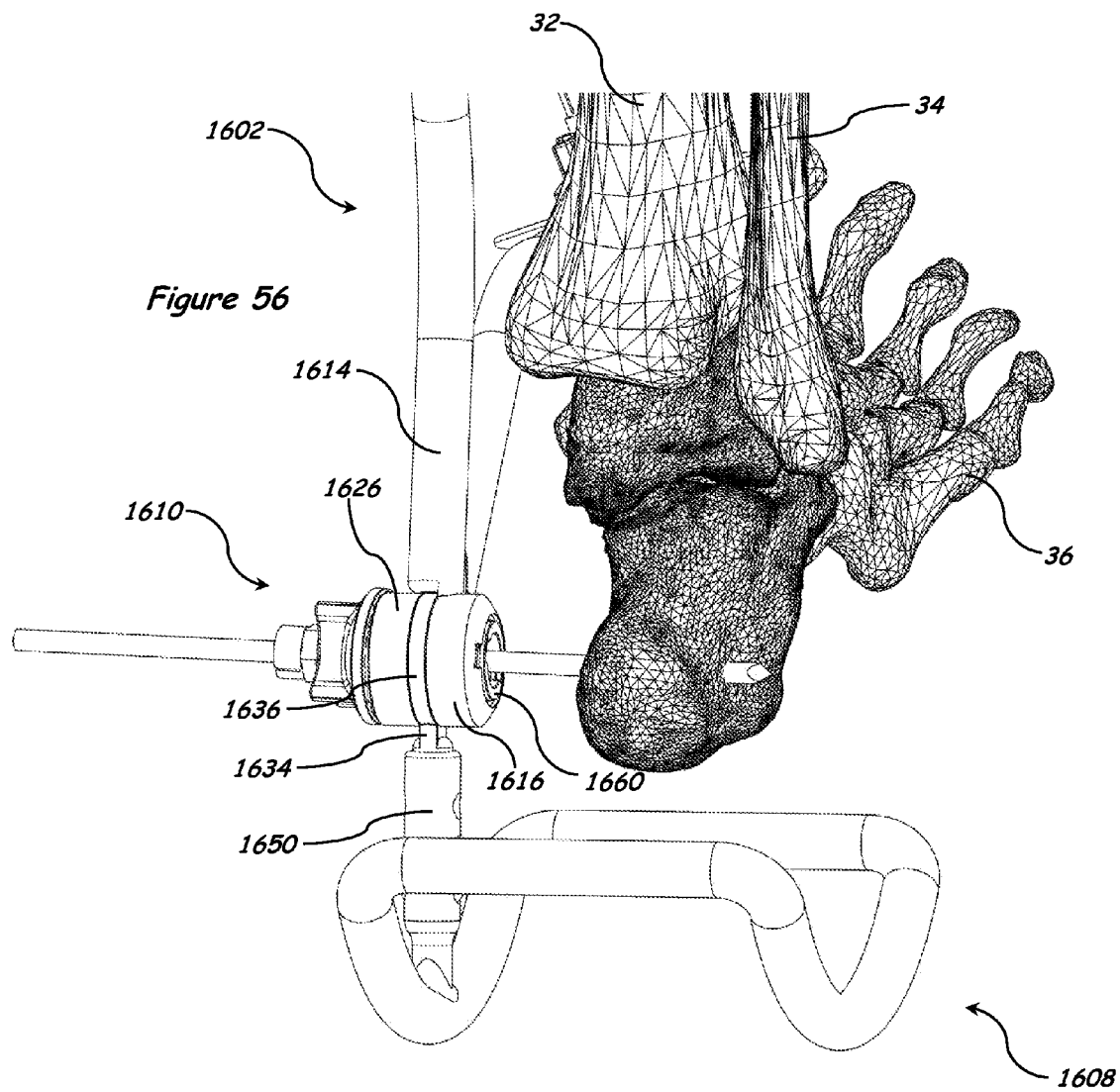
FIG. 56 is a detailed posterior-lateral view of the fourth embodiment of the ankle external fixator.
Figure 57:
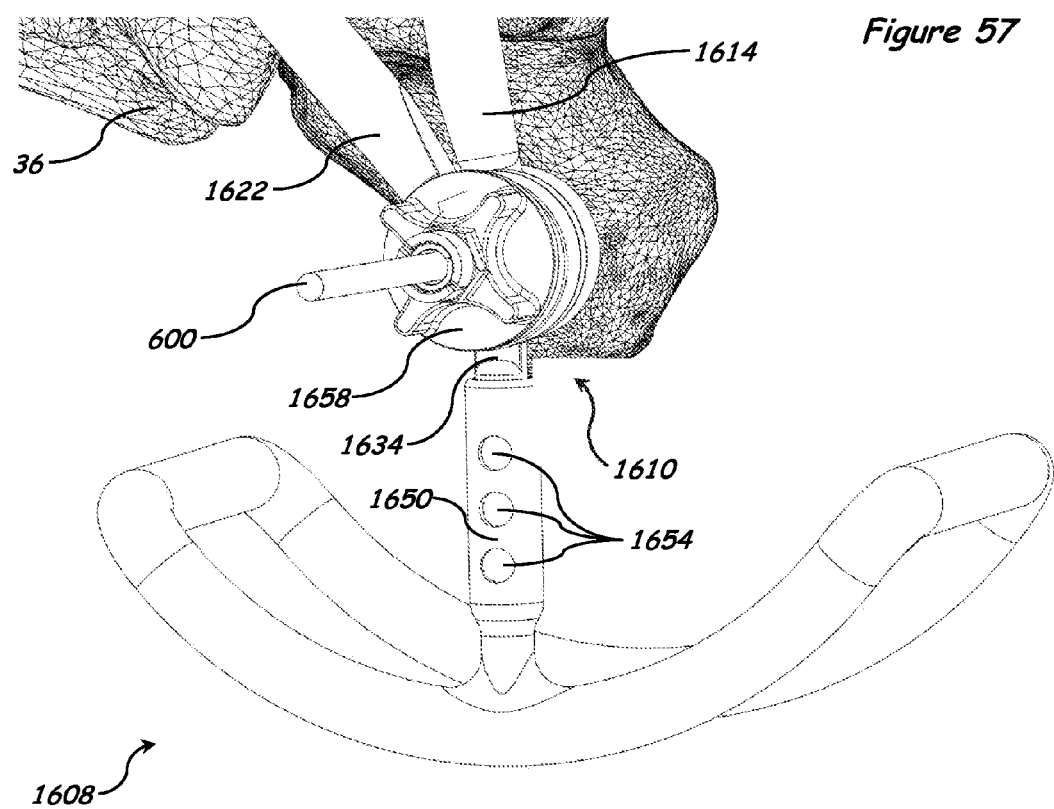
FIG. 57 is a detailed medial view of the fourth embodiment of the ankle external fixator.
Figure 60:
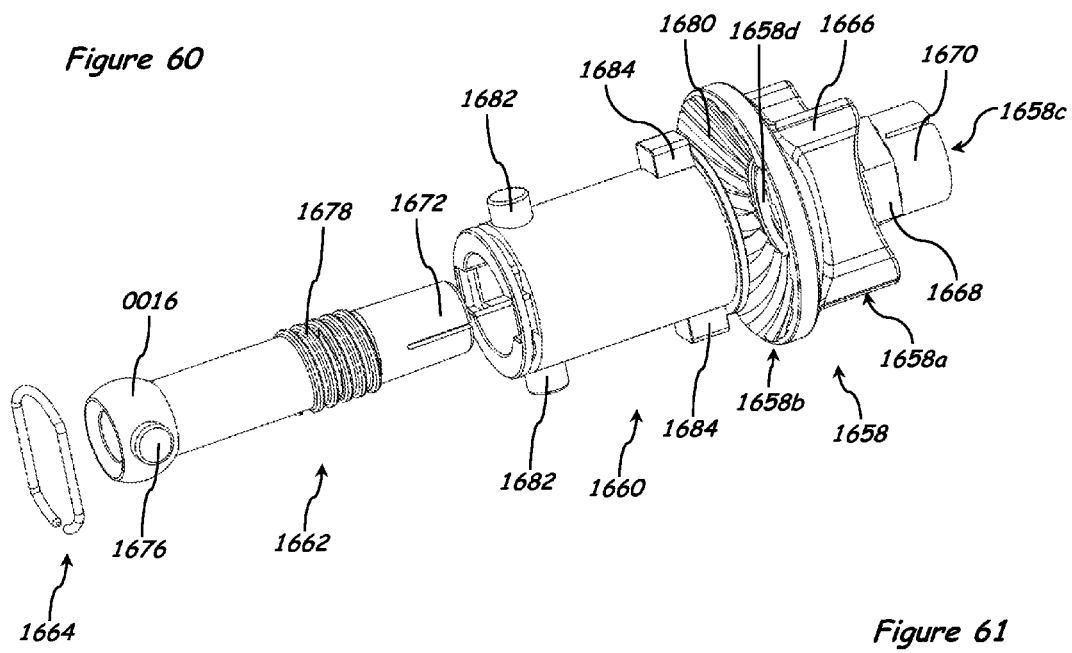
FIG. 60 is a detailed exploded view of the cartridge utilized in the fourth embodiment of the ankle external fixator.
Figure 61:
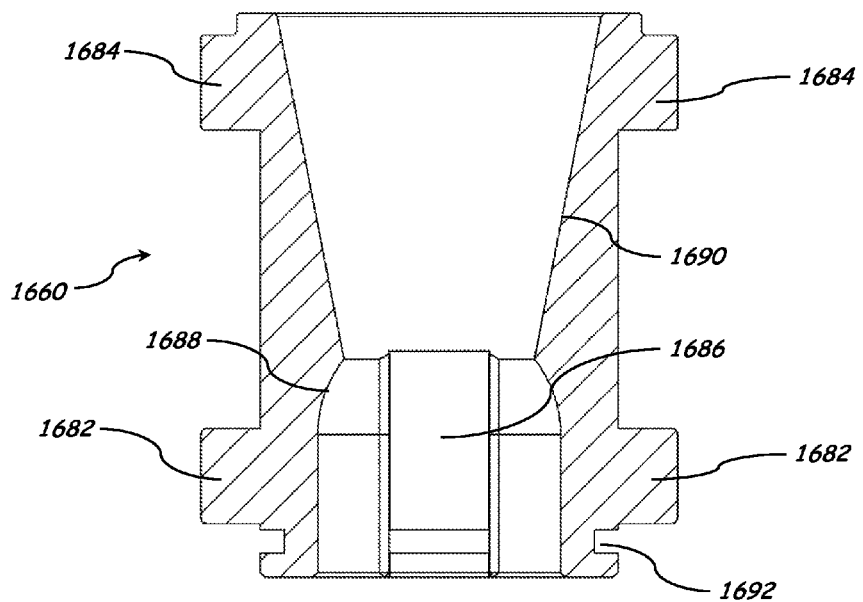
FIG. 61 is a section view of the main body of the cartridge utilized in the fourth embodiment of the ankle external fixator.

Referring now to FIGS. 48-50, a third embodiment of an exemplary ankle-spanning external fixation system 1500 is illustrated mounted on a lower extremity 28 comprising a tibia 32, fibula 34 and a foot 36.

FIGS. 48-52 illustrate a third embodiment of an exemplary ankle-spanning external fixation system 1500 comprises a proximal frame including a first external fixation component 1502*a*, a second external fixation component 1502*b*, and a fastener 1506, and connecting to a distal (e.g., first) frame such as foot frame 1504, and open-end clamp systems 400 and 1300. The ankle-spanning external fixation system 1500 can be adapted to couple to the tibia 32, the fibula 34 and/or the foot 36 by use of a closed-end clamp system 300 and/or the open-end clamp systems 400 and 1300.

The first and second external fixation components 1502*a* and 1502*b*, and the foot frame 1504, fastener 1506 and open-end clamp systems 400 and 1300 can be formed of any suitable material known to one skilled in the art that provides an adequate stiffness or resistance to torsion, stress, torque and/or other forces that may be applied to the system 1500, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form the first external fixation component, the second external fixation component, the foot frame, the fastener, and the open-end clamp systems of aluminum, stainless steel and/or carbon fiber, at least because these materials have properties that are well suited to external fixation of fractures.

In the illustrated embodiment 1500 in FIGS. 48-52, a proximal (e.g., second) bar frame comprises a first external fixation component 1502*a* comprising a straight first component proximal (e.g., first) end portion 1508 and a curved first component distal (e.g., second) end portion 1510 including a first pivot structure 1512*a* comprising a rough surface 1514*a* and a threaded shaft centered and formed perpendicularly on the rough surface 1514*a*, and said first external fixation component 1502*a* pivotedly coupled and locked to a second external fixation component 1502*b* comprising a straight second component proximal (e.g., first) end portion 1534, a straight second component distal (e.g., second) end portion 1518 of a reduced diameter, and a curved or arc portion 1532 connecting the second component proximal end portion 1534 and a second component distal end portion 1518, said arc portion 1532 having a pivot structure 1512*b* with a rough surface 1514*b* and a centered through-bore for receiving the threaded shaft of the pivot structure 1512*a* to form a movable joint or hinge. A fastener, such as threaded nut 1506, is coupled to the threaded shaft of the first pivot structure 1512*a* to form a threaded connection to lock the movable joint, thus, also locking the first and second external fixation component 1502*a* and 1502*b* in place. The interaction between the rough surfaces 1514*a* and 1514*b* in a locking state provides anti-rotation to the first and second fixation components 1502*a* and 1502*b*. The second component proximal end portion 1534 is attached by, for example, welding, soldering or gluing to a distal frame, such as the foot frame 1504, to form a unitary, prefabricated modular structure. Alternatively, the foot frame 1504 can be integrally machined or formed with the second external fixation component 1502*b* from a single piece of metal or other material to form a unitary structure. The foot frame 1504 comprises a straight posterior segment 1516*a*, a straight inferior segment 1516*b*, and a curved or arc segment 1516*c* connecting the straight posterior segment 1516*a* and the straight inferior segment 1516*b* to form a curved frame or rod or bar for protecting and supporting both the posterior and the inferior aspects of a foot or joint such as the ankle while healing is taken place. Said inferior frame portion 1516*b* and said posterior frame portion 1516*a* are operatively disposed in at least partially surrounding and spatial relation to the ankle or the heel of the foot 36, wherein said posterior frame portion 1516*a* extends angularly from and above said inferior frame portion 1516*b*. The second component distal end portion 1518 has a smaller diameter and is attached (e.g. welded, soldered or glued) to an outrigger 1522 used as a clamp attachment, for example. The outrigger 1522 can also be integrally machined or formed with the second external fixation component 1502*b*.

The first and second component proximal end portions 1508 and 1534, the first and second component distal end portions 1510 and 1518, and more generally the first and second external fixation components 1502*a* and 1502*b* and the posterior and inferior segments 1516*a* and 1516*b* can be straight or curved. The first and second external fixation components 1502*a* and 1502*b* and the foot frame 1504 of the system 1500 can have any cross-sectional shapes such as circle, square, rectangle, hexagon, etc., and can have uniform diameter or varied diameter along their lengths. The first and second external fixation components 1502*a* and 1502*b* including the foot frame 1504 of the system 1500 can each be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy).

The pivot structures 1512a and 1512b can have any cross-sectional shapes, not just limited to a circular shape as illustrated in this example. The pivot structures 1512a and 1512b can also have any lengths or thickness as measured along its pivot axis. The pivot structures 1512a and 1512b of the movable hinge or joint can each also be an integral part of (e.g. integrally formed with) or a separate part to (e.g. removably coupled to) their respective first external fixation component 1502a and second external fixation component 1502b. The rough surfaces 1514a and 1514b can include a serration or radial interdigitation or combinations thereof. In a system where both pivot structures 1512a and 1512b each comprises a through-bore, a second fastener having a head and a threaded shaft can be used to couple the pivot structures 1512a and 1512b and operably interacts with the threaded nut 1506 to lock the pivot structures 1512a and 1512b. The fastener(s) can have a secure gripping surface for ease of handling during surgery. As illustrated, the first external fixation component 1502a and the second external fixation component 1502b including the foot frame 1504 each is made as a unitary modular structure. In the modular structure, the first external fixation component 1502a and the second external fixation component 1502b and the foot frame 1504 can each be made from a plurality of straight and/or curved segments connected via threads, snap-fit or interference fit.

Referring now to FIGS. 53-57, a fourth embodiment of an exemplary ankle-spanning external fixation system 1600 is shown mounted on an exemplary lower leg 28 comprising a tibia 32, fibula 34 and a foot 36.

FIGS. 53-61 illustrate a fourth embodiment of an exemplary ankle-spanning external fixation system 1600 comprising a proximal (e.g., first) frame having a first external fixation component 1602 and a second external fixation component 1604, a proximal frame connector 1606, and a distal (e.g., second) frame or a foot frame 1608, a distal frame connector 1650, a cartridge system 1610 and an open-end clamp system 400. The ankle-spanning external fixation system 1600 can be adapted to attach to the tibia 32, the fibula 34 and/or the foot 36 by use of a closed-end clamp system 300 and/or the open-end clamp systems 400 and 1300 and other fixation elements such as bone pins 600 or 700.

The first external fixation component 1602, the second external fixation component 1604, the proximal (e.g., first) frame connector 1606, the foot frame 1608, the distal (e.g., second) frame connector 1650, the cartridge system 1610 and the open-end clamp system 400 can be formed of any suitable material known to one skilled in the art that provides an adequate stiffness or resistance to torsion, stress, torque and/or other forces that may be applied to the system 1600, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form the first external fixation component, the second external fixation component, the third external fixation component, the fourth external fixation component, the cartridge system and the open-end clamp system of aluminum, stainless steel and/or carbon fiber, at least because these materials have properties that are well suited to external fixation of fractures.

In the illustrated embodiment 1600 in FIGS. 53-61, the proximal frame comprises the first external fixation component 1602 and the second external fixation component 1604. The external fixation component 1602 comprises a first component proximal (e.g., first) end portion 1612 and a first component distal (e.g., second) end portion 1614 integrally formed with or coupled to a pivot structure 1616 having a rough surface 1618 and a through-bore bound by an inner surface having engagement features such as threads and key ways 1620 configured for receiving and connecting to at least a portion of the cartridge system 1610 for coupling to a bone and locking the system 1600. The second external fixation component 1604 comprises a second component distal (e.g., first) end portion 1624 and a second component proximal (e.g., second) end portion 1622 integrally formed with or coupled to a pivot structure 1626 having a rough surface 1628 and a through-bore bound by an inner surface having engagement features such as threads and key ways 1630 configured for receiving and connecting to at least a portion of the cartridge system 1610 for coupling to a bone and locking the external fixation components 1602 and 1604 in position.

The first and second external fixation components 1602 and 1604 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). The first and second component proximal end portions 1612 and 1622 and the first and second component distal end portions 1614 and 1624 can be straight or curved. The first and second external fixation components 1602 and 1604 can have any cross-sectional shapes such as circle, oval, triangle, rectangle, square, polygonal shape. The first and second external fixation components 1602 and 1604 can have any uniform or varied diameter or thickness along their lengths. The pivot structures 1616 and 1626 can have any external cross-sectional shapes, not limited to just circular shape as illustrated in this example. The pivot structures 1616 and 1626 can also have any lengths or thickness as measured along its pivot axis. The pivot structures 1616 and 1626 can also be integrally formed with or removably coupled to their respective first external fixation component 1602 and second external fixation component 1604. The rough surfaces 1618 and 1628 can include serration or radial interdigitation or combinations thereof.

The proximal frame connector 1606 comprises an elongated body comprising a connector proximal end portion 1634 integrally formed with or coupled to a pivot structure 1636 having a rough surface 1638 and an opposing rough surface 1640 and a through-bore connecting the two opposing surfaces 1638 and 1640 bound by an inner surface configured (e.g. key ways 1642) for receiving and locking onto at least a portion of the cartridge system 1610, and a bifurcated connector distal end portion including a pair of movable portions 1644 that are movable to flex toward and away from each other and arranged with one or more protrusions 1648 to engage with a hole 1654 in a distal frame connector 1650 of the lower frame such as the foot frame 1608.

The distal frame such as the foot frame 1608 comprises a ring frame configured to protect both the posterior and inferior aspects of a foot or the ankle. The ring frame comprises a multiple curved elongated body structure defining a first curved side rod spaced apart and parallel to a second curved side rod wherein a first end connector extending from said first curved side rod to said second curved side rod in said inferior portion and a second end connector extending from said first curved side rod to said second curved side rod in said posterior portion. Said inferior frame portion and said posterior frame portion are operatively disposed in at least partially surrounding and spatial relation to the ankle or the heel of the foot 36, wherein said posterior frame portion extends angularly from and above said inferior frame portion. The foot frame 1608 has a curvature from inferior to posterior with its concave surface orienting toward the heel of the foot. The foot frame 1608 further comprises a distal frame connector 1650 with a through-bore extending longitudinally through at least a portion of the elongated body 1650 for receiving the bifurcated connector distal end portion 1644, and one or more holes 1654 for engaging with the one or more protrusions 1648 on the bifurcated connector distal end portion 1644. The elongated body 1650 is attached to a portion of one of the first and second curve side rods. The arrangement of the multiple holes 1654 along the distal frame connector 1650 provides adjustability to the spatial relation between the foot frame 1608 and the heel or the ankle. The foot frame including the distal frame connector and the proximal frame connector can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy).

The cartridge system 1610 for coupling the system to a bone portion via a bone pin 600 or 700 and locking the pivot structures 1616, 1626, and 1636, and thus, also locking the ankle-spanning external fixation system 1600 comprises a knob 1658, a main body 1660, a variable position shaft 1662 and a retaining clip 1664.

The knob 1658 comprises a knob body 1658a having a main body facing end 1658b and an opposing end 1658c. The knob body 1658a includes a funnel-like or frusto-conical internal surface or an internal surface having one or more tapered facets to receive and alternatively circumferentially compress and release a slit end or a funnel-like or tapered external surface of the shaft 1662 for clamping a fixation element such as bone pin 600. The funnel-like or frusto-conical internal surface or more generally the through-bore bound by walls extending from the main body facing end 1658b to the opposing end 1658c of the knob body 1658a is designed to be larger toward the main body facing end 1658b than toward the opposing end 1658c of the knob body 1658a, and includes a first locking feature such as threads 1658d. The tapered or conical internal surface inside the knob body 1658a can be replaced with a taper insert. The opposing end 1658c of the knob body 1658a can include one or more slits or breakable lines for accommodating a broader range of dimensional tolerances of the bone pin 600 or 700. The knob 1658 can have irregularly shaped geometry 1666 for providing a secure grip surface and optionally a hexagonally shaped geometry 1668 that interfaces with a wrench.

The variable position shaft or shaft 1662 includes an end portion including a stopper or an enlarged structure or structures such as a head 0016 for preventing the shaft 1662 from passing completely through the main body 1660, and a locking or engagement feature such as threads 1678 on the external surface of the shaft 1662, and one or more breakable lines or slits 1672 on an opposing end portion of the shaft. The slit end 1672 of the shaft 1662 can be tapered to match the tapered internal surface of the knob body 1658a. The funnel like or tapered internal surface of the knob body 1658a preferably interacts via the engagement features, such as the threads 1658d and 1678, with the externally tapered or funnel-like surface or the slit end 1672 of the shaft 1662 to provide clamping. The through-bore or opening in the opposing end 1658c of the knob 1658 has a diameter smaller than the uncompressed diameter of the slit end 1672 of the shaft 1662 to provide interference fit among the inner surface of the knob 1658, the slit end 1672 and the bone pin such as bone pin 600 or 700. The shaft 1662 is configured to extend through the main body 1660 and into the through-bore of the knob 1658 such that the stopper 0016 is disposed in the main body 1660 and at least a portion of the threads 1678 of the shaft 1662 and the slit end 1672 disposed outside the main body 1660 and inside the knob body 1658a. The shaft threads 1678 operably engage the internal threads 1658d of the knob 1658 in forming a threaded connection with the knob 1658 to form a cannulation or reception for receiving a bone pin, such as bone pin 600, of uniform diameter, or bone pin 700 of varying diameter. A portion of the shaft 1662 or the stopper 0016 can include an at least partially spherical surface to permit the bone pin 600 or 700 to orient relative to the main body 1660, and can have at least one anti-rotation feature such as protrusion 1676 adapted to sit in a key way in the main body 1660.

In operation, the tightening of the knob 1658 pushes the slit end 1672 of the shaft 1662, guided by the tapered internal surface or structure of the knob body 1658a, toward or through the opposing end 1658c of the knob 1658. The slit end 1672 is compressed circumferentially onto the bone pin 600 or 700 at the opposing end 1658c of the knob 1658 as the slit end 1672 is pushed through the smaller opening at the opposing end 1658c of the knob 1658, and thus, clamping onto the bone pin 600 or 700 by interference fit.

The main body 1660 is configured to extend through the pivot structures 1616, 1626, and 1636 of the first and second external fixation components 1602 and 1604 and the connector 1606. The main body 1660 has a cylindrical body with proximal protrusions 1682 for engaging with key ways 1620 on the inner surface of the pivot structure 1616 of the first external fixation component 1602 and distal protrusions 1684 for engaging with key ways 1630 on the inner surface of the pivot structure 1626 of the second external fixation component 1604. The main body 1660 has inner surface configured to operably interact with the shaft 1662 to provide both angular rotation of the shaft 1662 relative to the main body 1660 and anti-rotation of the shaft 1662 during locking. The inner surface of the main body includes one or more key way 1686 for capturing the protrusions 1676 of the shaft 1662 for rotational stability, concave surfaces 1688 for interacting with the at least partially spherical stopper 0016 of the shaft 1662 and tapered or conical surface 1690 for providing angular rotation of the shaft 1662, and slotted geometry 1692 that accepts a ring clip 1664 for preventing the variable position shaft 1662 to exit the main body 1660 once the cartridge system 1610 is completely assembled.

The ankle-spanning external fixation system 1600 is assembled by firstly, snap-fitting together the first external fixation component 1602, the second external fixation component 1604 and the connector 1606 via male/female ends on their pivot structures 1616, 1626 and 1636. When the first external fixation component 1602, the second external fixation component 1604 and the connector 1606 are rotated into their closed state, the key ways 1620, 1630 and 1642 of the respective pivot structures 1616, 1626 and 1636 become aligned and allow the assembled cartridge system 1610 to slide in. Once the cartridge system 1610 is in place, the first external fixation component 1602, the second external fixation component 1604 and the connector 1606 can be opened up to the desired position according to anatomical considerations. Once the current embodiment 1600 is deployed and in position, the cartridge system can be adjusted and then locked in place by further tightening knob 1658, which in turn locks the first external fixation component 1602, the second external fixation component 1604 and the connector 1606 via the interactions of rough surfaces 1618, 1638, 1640 and 1628.

Figure 62:
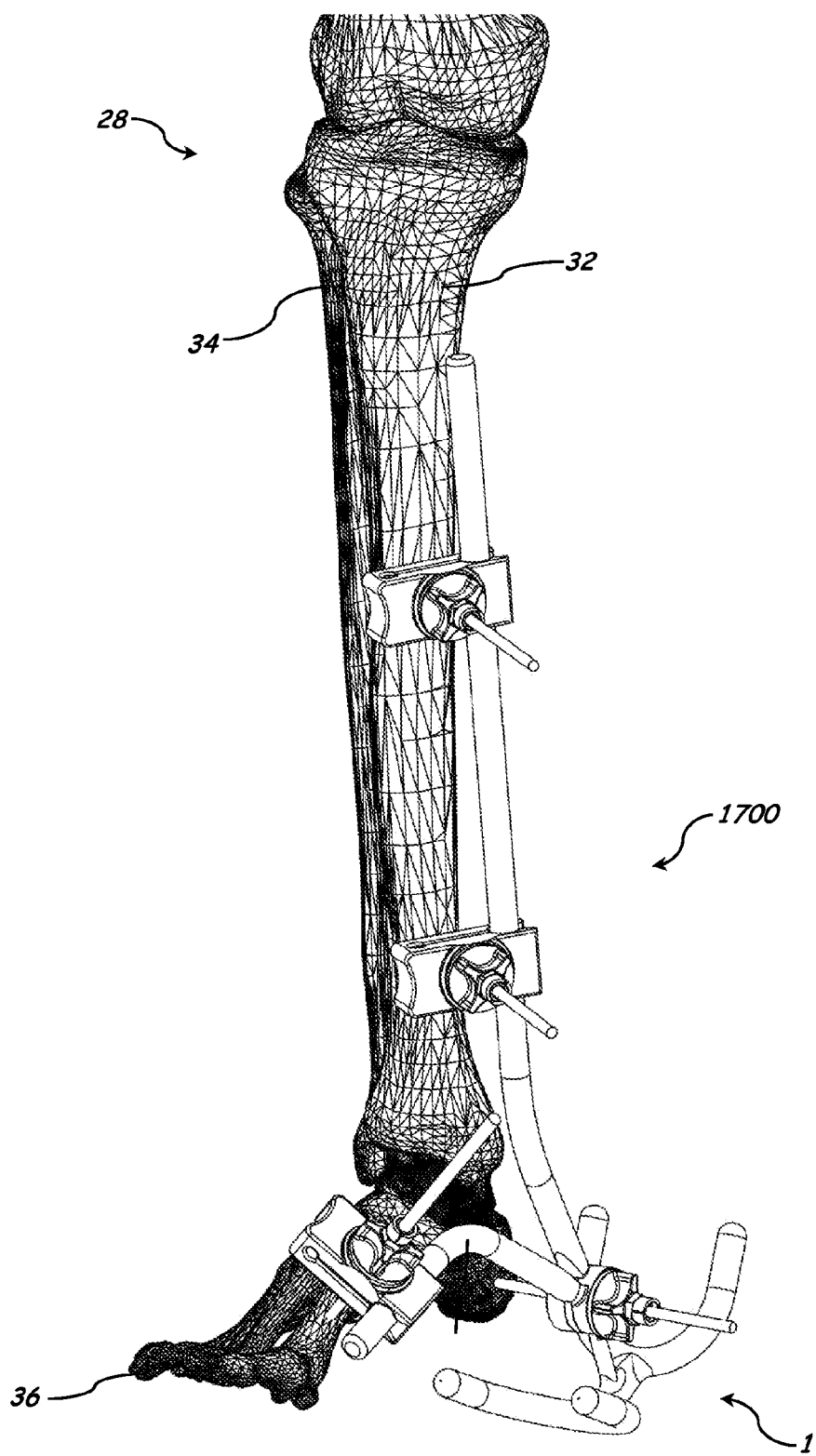
FIG. 62 is an anterior-medial perspective view of a leg with a fifth embodiment of the ankle external fixator and its associated clamps.
Figure 63:
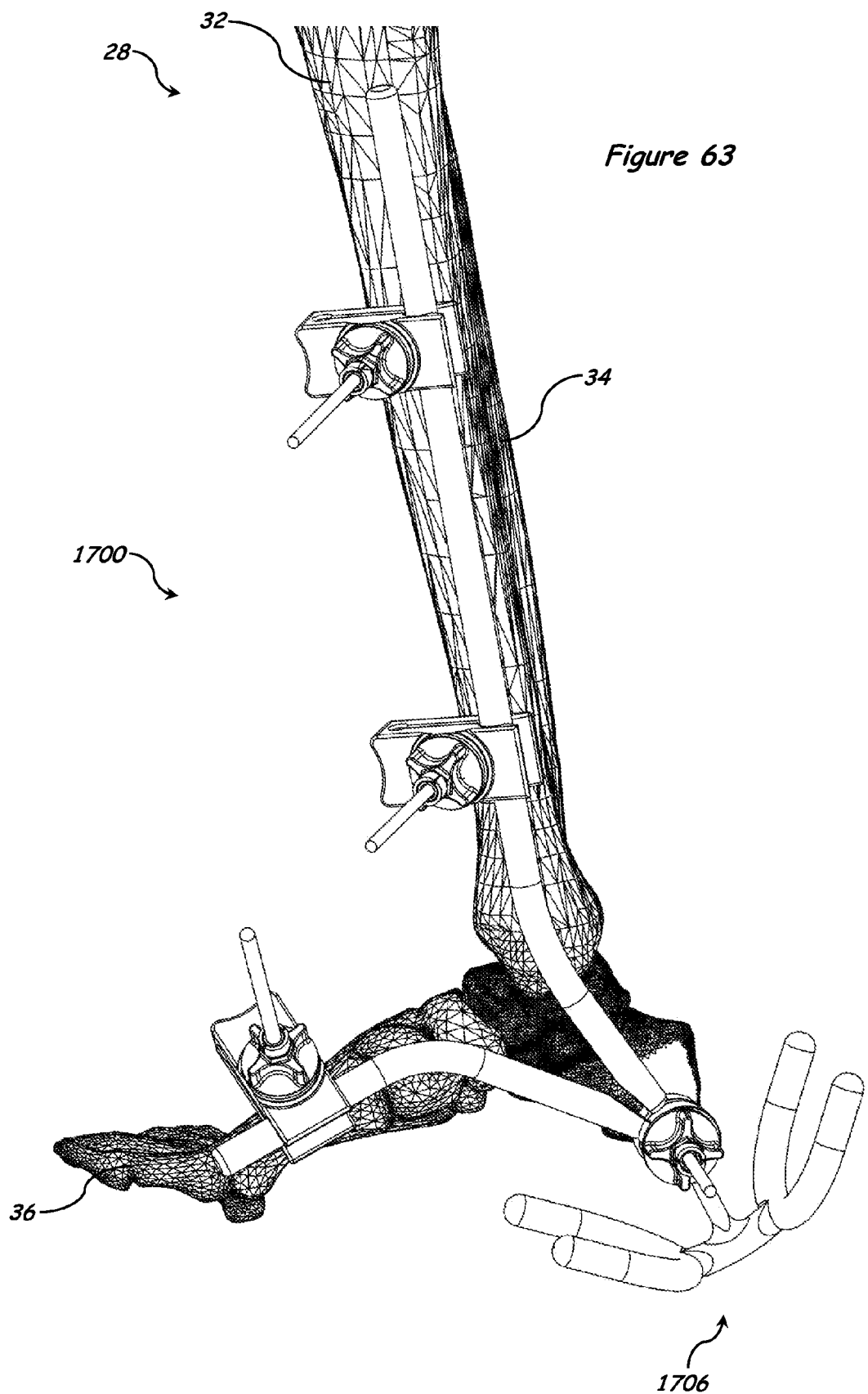
FIG. 63 is a medial perspective view of a leg with the fifth embodiment of the ankle external fixator and its associated clamps.
Figure 64:
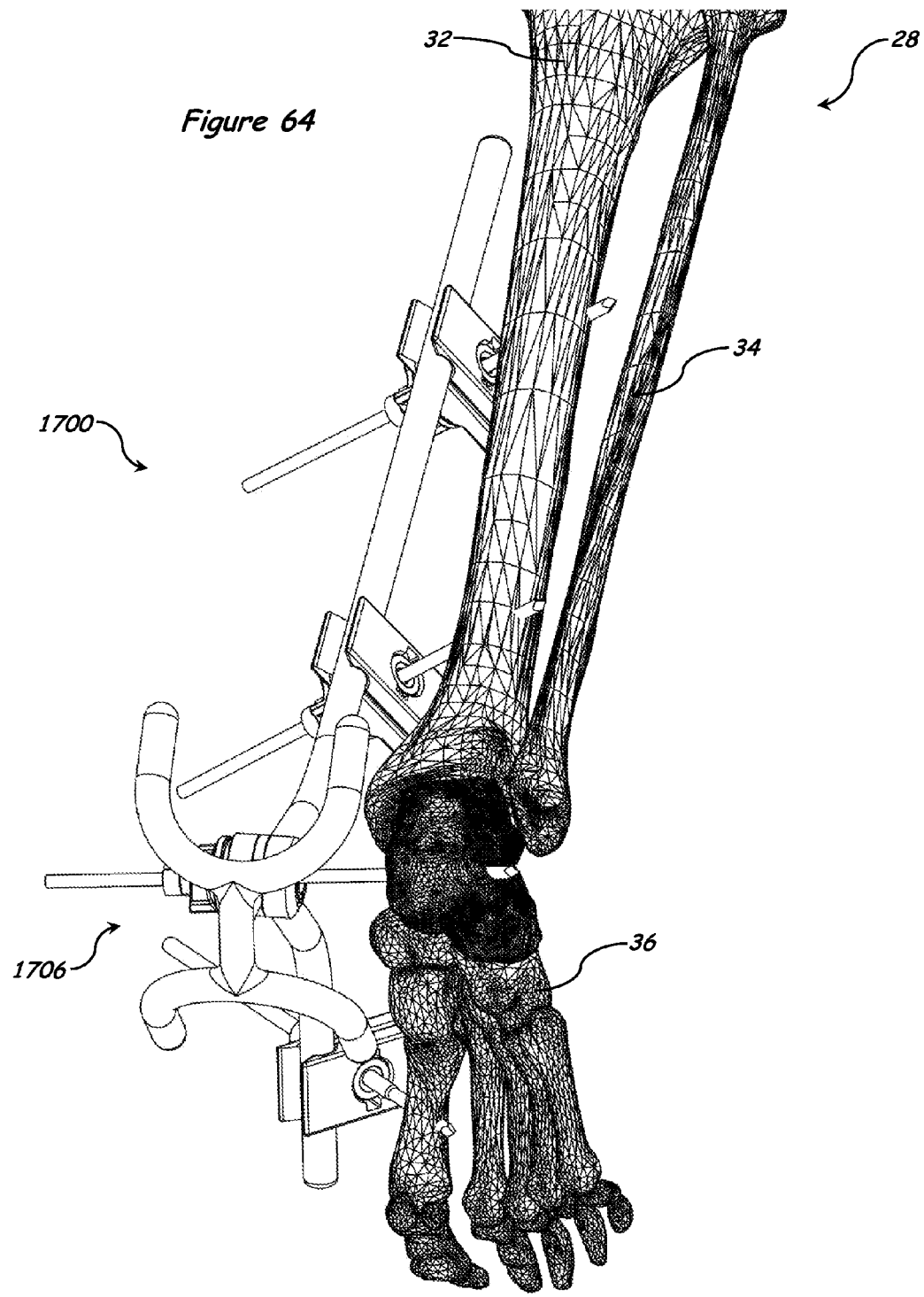
FIG. 64 is a posterior-inferior perspective view of a leg with the fifth embodiment of the ankle external fixator and its associated clamps.
Figure 65:
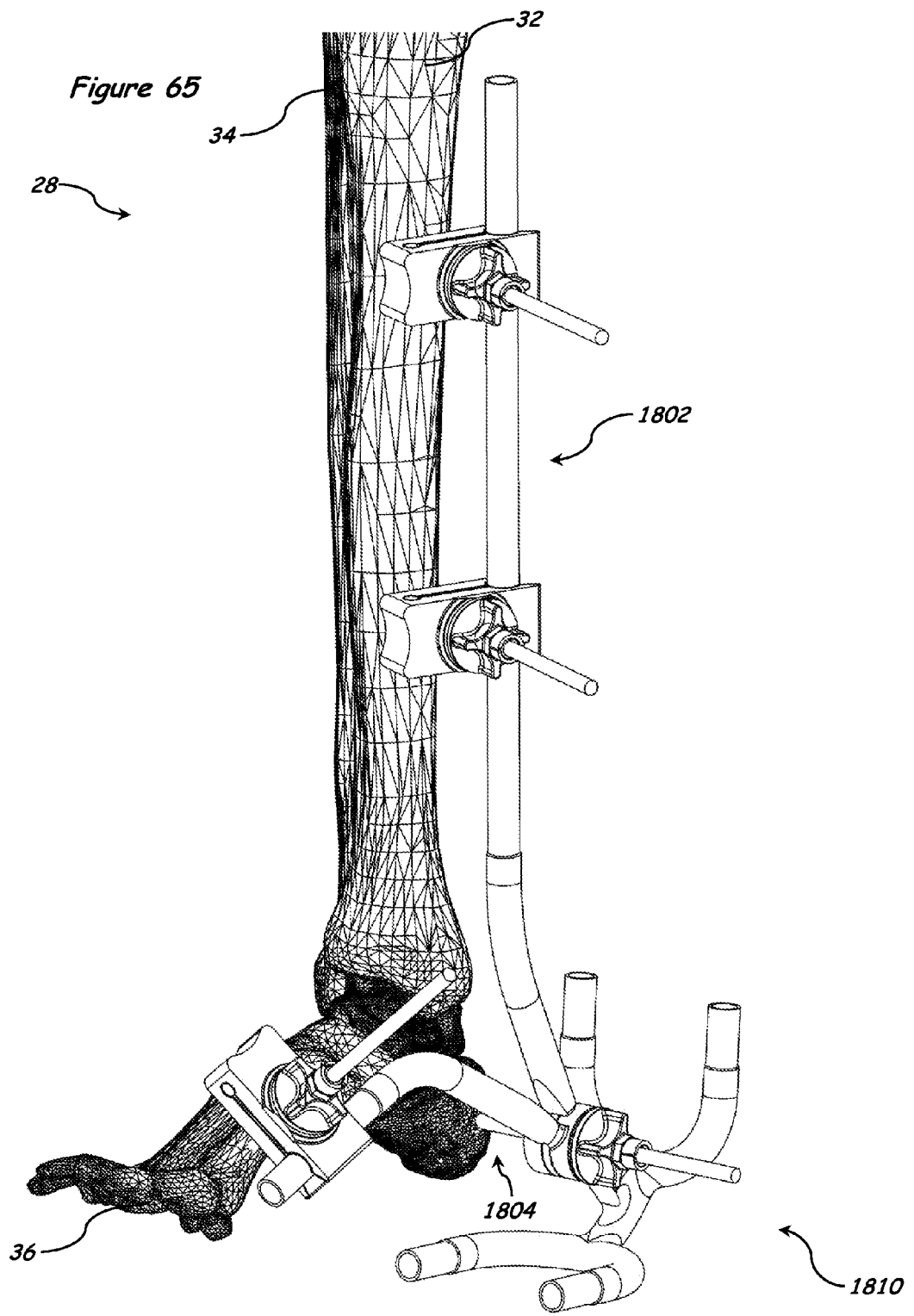
FIG. 65 is an anterior-medial perspective view of a leg with a sixth embodiment of the ankle external fixator and its associated clamps.
Figure 66:
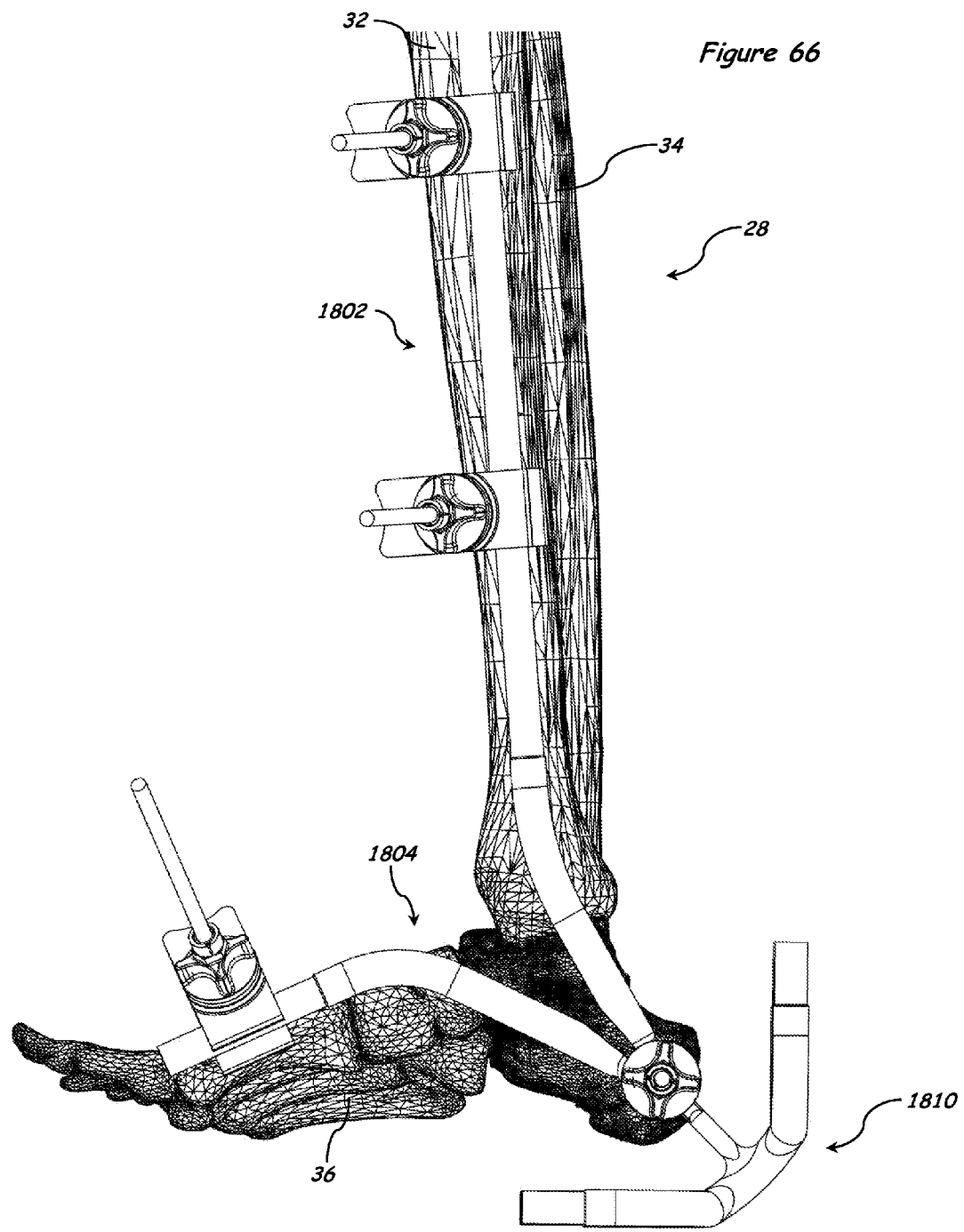
FIG. 66 is a medial perspective view of a leg with the sixth embodiment of the ankle external fixator and its associated clamps.
Figure 67:
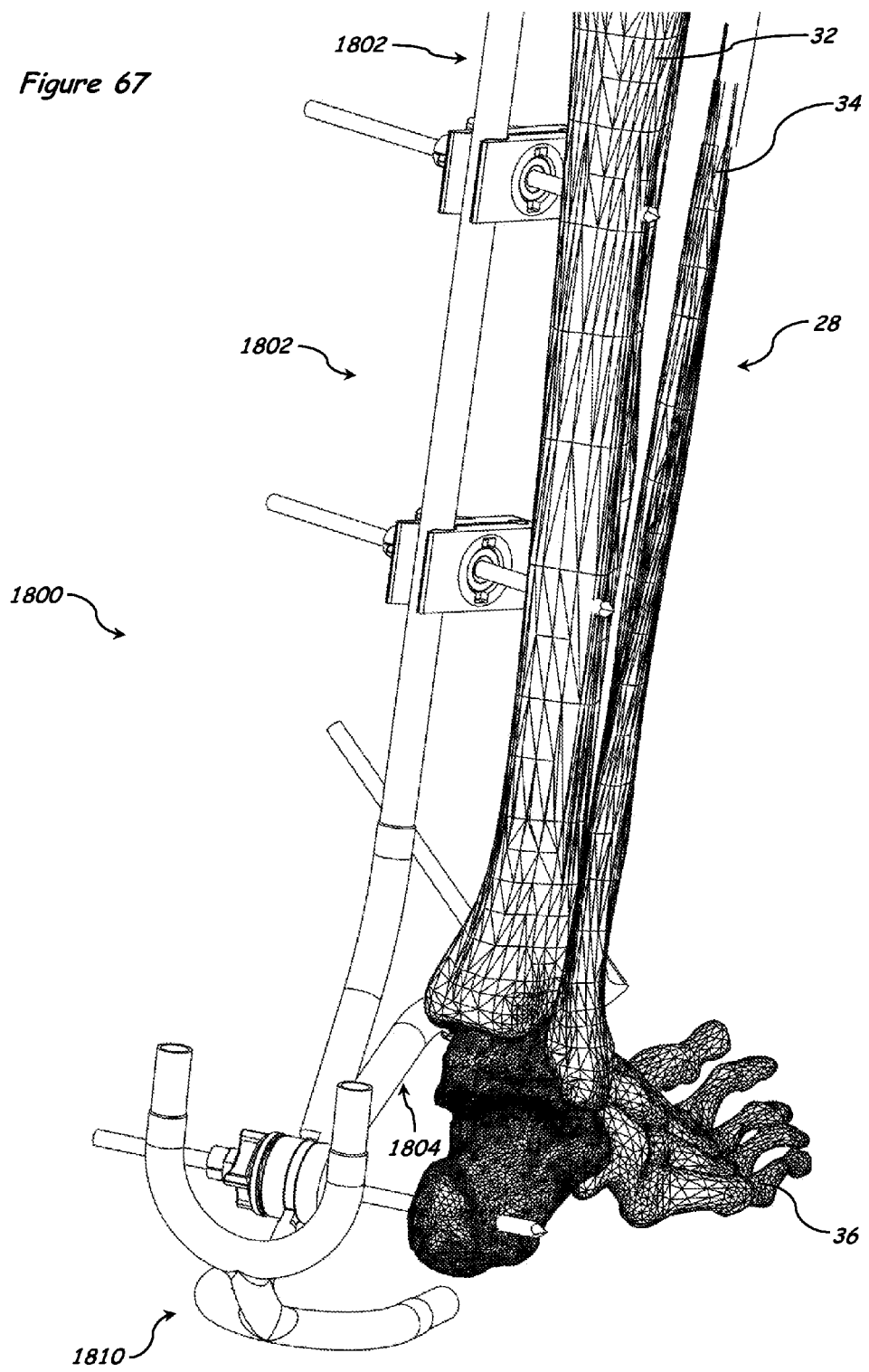
FIG. 67 is a posterior-lateral perspective view of a leg with the sixth embodiment of the ankle external fixator and its associated clamps.
Figure 69:
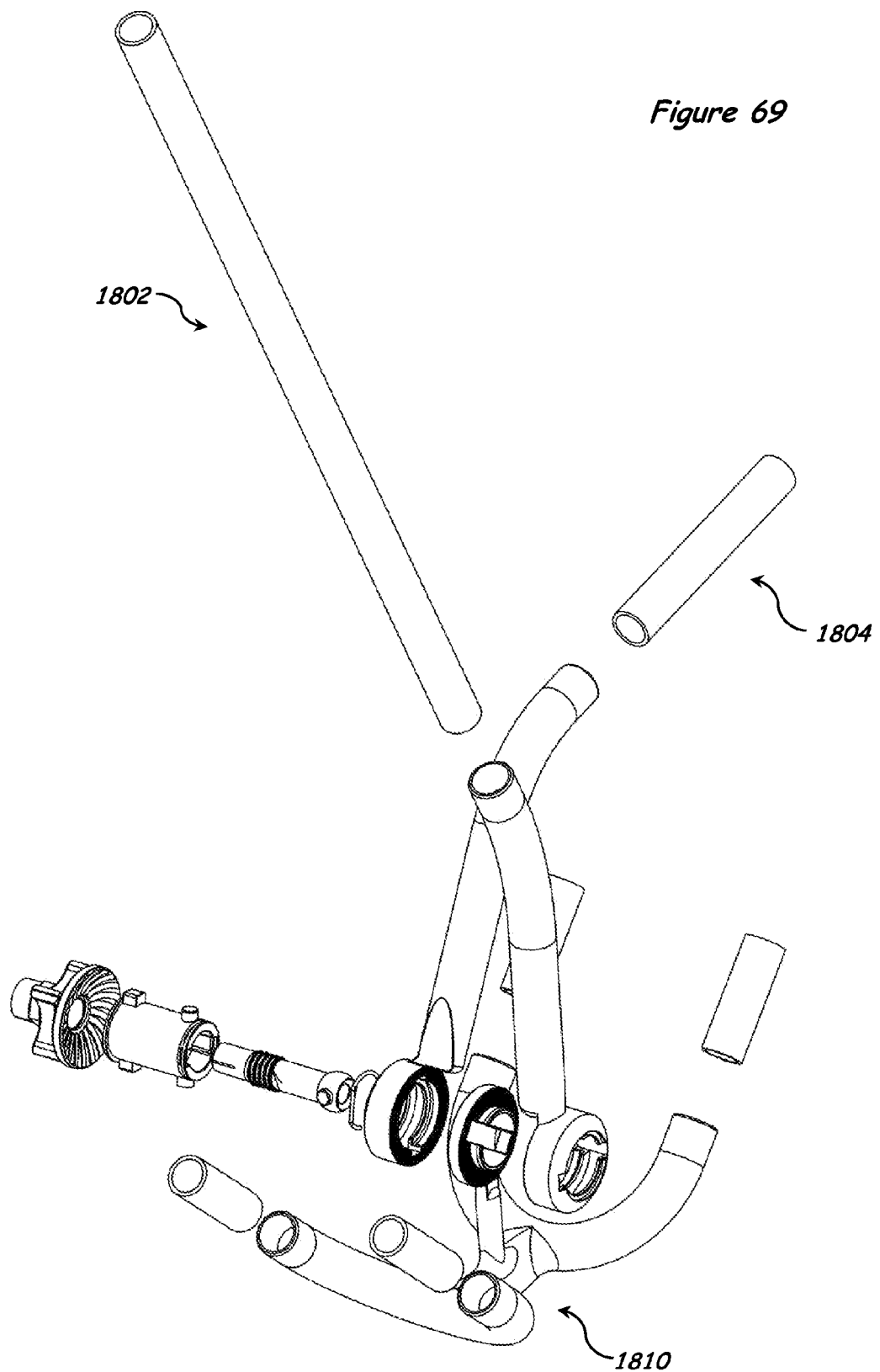
FIG. 69 is a detailed posterior-lateral exploded view of the sixth embodiment of the ankle external fixator.

Referring now to FIGS. 62-64, an alternative embodiment 1700 of the ankle-spanning external fixation system 1600 is illustrated wherein the system 1700 includes the curved foot frame 1706 comprising a U-shaped posterior (e.g., first) frame section and a U-shaped inferior (e.g., second) section connected at the base by a straight frame section. The two U-shaped frame sections are arranged to lie on different planes forming an angle of about 90 degrees. Other angles also lie within the spirit and scope of the various embodiments of the present invention.

Referring now to FIGS. 65-69, an alternative embodiment 1800 of the ankle-spanning external fixation system 1700 is illustrated wherein the first external fixation component 1802, second external fixation component 1804, and the foot frame 1810 are each of modular construction, comprising two or more straight and/or curved segments joined together via plug-socket joints and fixed in place by threading, snap-fitting or interference-fitting. Each of the first external fixation component 1802, second external fixation component 1804, and the foot frame 1810 of the system 1800 can also be made into a unitary structure or unitary modular structure by molding or forming permanent connection among the subcomponents or segments by welding, soldering, crimping, brazing, and gluing/epoxying. The system 1800 can be single-use or disposable.

Figure 70:
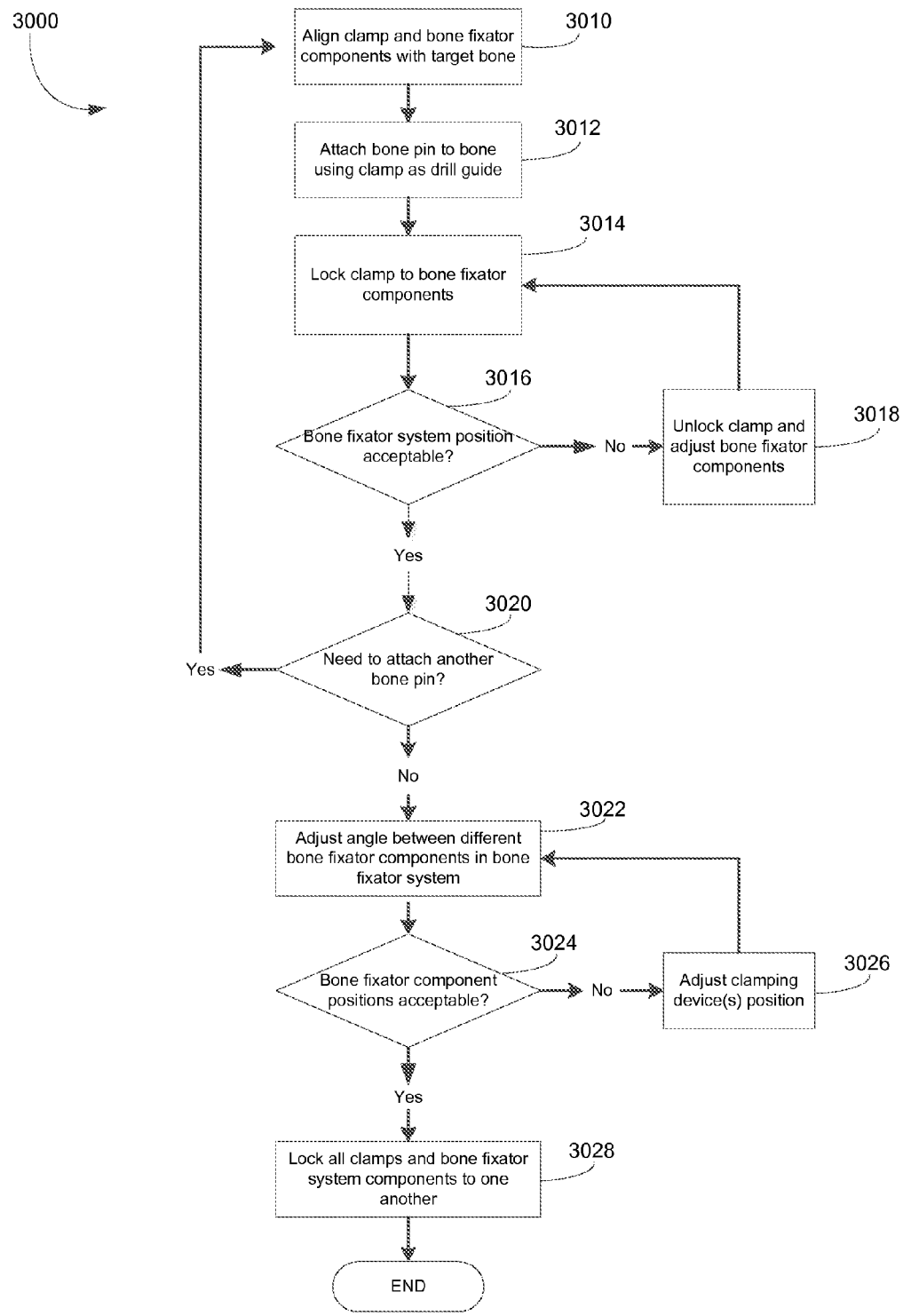
FIG. 70 is a flow diagram of a method of fixating a bone fixator system to a target joint of a subject.

Referring now to FIG. 70, a flow diagram of an embodiment of a method 3000 for fixating a bone fixator system about a target joint is shown. The method may be performed by a variety of users, including healthcare professionals, technicians, and patients installing and/or adjusting the bone fixator system. The bone fixator system used to implement the method may be or include features of any of the fixation systems disclosed herein (e.g., external fixation systems 100, 200, 800, 900, 1000, 1100, 1200, 1400, 1500, 1600, 1700, 1800, etc.) and the clamping devices used herein to implement the method may be or include features of any of the clamping devices and systems disclosed herein (e.g., clamp systems 300, 400, 500, 1300, 2600, etc.).

At 3010, components of a bone fixator system are aligned with target bone(s) about a target joint to be fixated. The target joint may be an elbow, a knee, an ankle, etc. For example, the bone fixator system may include a first fixation component and a second fixation component, the first fixation component may be aligned relative to a first target bone disposed adjacent to the target joint, and the second fixation component may be aligned relative to a second target bone disposed adjacent to the target joint on another side of the knee from the first target bone.

A clamp is also aligned relative to a target bone. For example, a clamp may be aligned with the target bone based on a desired position and/or orientation of a bone pin to be attached to the bone and secured or otherwise received by the clamp. The clamp may also be received on one of the fixation components of the bone fixator system while aligning the clamp.

At 3012, a bone pin is attached (e.g., secured, coupled, drilled in, etc.) to a target bone using a clamp as a drill guide. For example, the clamp may define a through-bore configured to receive the bone pin. The through-bore may be used to sight or otherwise identify a target position on a surface of the target bone at which the bone pin is to be attached to the target bone. The bone pin is received through the through-bore of the clamp, and may be drilled into the bone. The clamp may be locked about the bone pin.

At 3014, the clamp is locked to the bone fixation component. For example, the clamp may include a pair of jaws defining an aperture through which the bone fixation component may pass, and a locking device may be used to force the jaws to compress the bone fixation component in order to lock the clamp to the bone fixation component.

At 3016, it is determined whether the bone fixation system is disposed in a desired orientation (e.g., position and/or angle relative to target joint, target bones, etc.). If the bone fixation system is not disposed in a desired orientation (e.g., the orientation is not acceptable), then at 3018, clamp(s) may be unlocked, providing degrees of freedom allowing for adjustment of the bone fixation system and components of the bone fixation system.

In some embodiments, determining whether the bone fixation system is disposed in a desired orientation includes comparing an observed joint status of the target joint to a desired joint status of the target joint. For example, a clinical goal for the joint may include a particular joint status (e.g., a degree of flexure of the joint, relative angles of the bones about the joint, etc.) to be achieved using the bone fixation system.

If it is determined that the bone fixation is disposed in a desired orientation, then at 3020, it is determined whether an additional bone pin needs to be attached. If it is determined that an additional bone pin is needed, then the procedure outlined in steps 3010, 3012, 3014, 3016, and 3018 may be followed to provide an additional clamp and attach an additional bone pin.

If it is determined that an additional bone pin is not needed, then at 3022, angle(s) between various components in the bone fixation system, such as between a first fixation component and a second fixation component, may be adjusted.

At 3024, after adjusting angles of the bone fixation system, it is determined whether the bone fixation system is disposed in a desired orientation. If it is determined that the bone fixation system is not disposed in a desired orientation, then at 3026, any locked clamp(s) and bone fixation component(s) are unlocked, allowing for adjustment of the orientation of the bone fixation system, such as by adjusting angle(s) between bone fixation components. An angle of a clamp relative to a bone fixation component may be adjusted, such as by adjusting an angle defined by a longitudinal axis of the bone fixation component and a plane transverse to a through-bore of the clamp in which the bone fixation component is received. A position of the clamp relative to the bone fixation component may be adjusted as well, such as by shifting and/or sliding the bone fixation component and the clamp relative to one another.

In some embodiments, the bone fixation system is configured to be fixated about a target ankle joint. The bone fixation system includes a first frame which may be aligned about a first target bone of the lower extremity adjacent to the target ankle joint. The bone fixation system also includes a second frame which may be aligned to at least partially surround the target ankle. For example, the second frame may include an inferior frame portion and a posterior frame portion. Fixating such a bone fixation system may include aligning the first frame with a first target bone of the lower extremity, aligning the second frame such that the inferior frame is disposed in an inferior position relative to the target ankle joint and such that the posterior frame is disposed in a posterior position relative to the target ankle joint, aligning a first clamp with the first target bone, attaching a first bone pin to the first target bone using the first clamp as a drill guide, and locking the first clamp to the first frame. In some embodiments, such a bone fixation system may be further fixated by aligning a second clamp with a second target bone (e.g., a bone of the foot or of the heel), attaching a second bone pin to the second target bone using the second clamp as a drill guide, and locking the second clamp to the second frame.

If it is determined that the bone fixation system is disposed in a desired orientation, then at 3028, all clamp(s) and bone fixation component(s) are locked. For example, locking devices may be used to lock clamp(s) to respective bone fixation component(s). In some embodiments, bone fixation components may be engaged and locked using fasteners or other engagement devices as disclosed herein.

In some embodiments, a bone fixator system includes: a first fixation component having a first length and coupled to a first bone portion, including a first component proximal end portion, a first component distal end portion, and a first pivot structure having a first axis of rotation and a first rough surface; a second fixation component having a second length and coupled to a second bone portion, including a second component proximal end portion, a second component distal end portion, and a second pivot structure having a second axis of rotation and a second rough surface; a first fastener for coupling and locking the first and second pivot structures, including a first engagement feature; and optionally a second fastener. At least one of the first and second pivot structures includes one of a protrusion, a recess, and a through-bore along its axis of rotation. At least one of the first and second pivot structures and second fastener includes a second engagement feature. The first engagement feature operably interacts with the second engagement feature to lock the first and second fixation components in position.

In some embodiments, the first pivot structure includes a first through-bore along its axis of rotation and the second pivot structure includes a second through-bore along its axis of rotation.

In some embodiments, the first fastener is one of an elongated body with an enlarged structure and a nut-like structure.

In some embodiments, one of the first and second pivot structures includes a protrusion defining a threaded shaft extending along its axis of rotation and the other of the first and second pivot structures includes a threaded through-bore along its axis of rotation.

In some embodiments, the first component distal end portion is formed with the first pivot structure and the second component proximal end portion is formed with the second pivot structure.

In some embodiments, the first and second pivot structures each define an outer surface, an inner surface, and an end surface, and at least one of the outer surface and the end surface includes the rough surface.

In some embodiments, a third fixation component is formed with a third pivot structure including a third through-bore along its axis of rotation and a third rough surface and a fourth, opposing rough surface.

In some embodiments, the first and second engagement features are selected from a group consisting of helical threads, fins, protrusions, tabs, slots, and a combination thereof.

In some embodiments, the first component distal end portion and the second component proximal end portion are curved.

In some embodiments, the rough surfaces are selected from a group consisting of serration and radial interdigitation.

In some embodiments, the first and second pivot structures have a laterally cross-sectional shape selected from a group consisting of circle, semi-circle, oval, square, rectangle, triangle, star, and polygon.

In some embodiments, the first and second through-bores have the laterally cross-sectional shape of a circle.

In some embodiments, the first pivot structure has a first pivot structure length along its axis of rotation, the second pivot structure has a second pivot structure length along its axis of rotation, and the first pivot structure length and the second pivot structure length are one of same and different.

In some embodiments, the sum of the first pivot structure length and the second pivot structure length is in the range of about 1 cm-20 cm.

In some embodiments, at least one of the first and second through-bores extends the full length of the pivot structure.

In some embodiments, the bone fixator system is disposed on either side or across both sides of a bone or a joint to be fixed.

In some embodiments, at least one of the first pivot structure and the second pivot structure is positioned between the proximal end portion and the distal end portion of the respective fixation component.

In some embodiments, the first and second fixation components include tubular structures.

In some embodiments, the first component distal end portion and the second component proximal end portion each includes a cross-sectional shape of a semi-circle.

In some embodiments, each of the first and second external fixation components is one of unitary construction, unitary modular construction, and modular construction.

In some embodiments, the bone fixator system is disposable.

In some embodiments, an external fixator system includes: a first fixation component coupled to a first bone portion, the first fixation component including a first component proximal end portion and a first component distal end portion formed with a first pivot structure with a first through-bore along an axis of rotation and a first rough surface; a second fixation component coupled to a second bone portion, including a second component distal end portion and a second component proximal end portion formed with a second pivot structure with a second through-bore along an axis of rotation and a second rough surface; a first fastener, including a head and a shaft having an external thread; and optionally a second fastener. At least one of the first through-bore, the second through-bore and the second fastener includes an internal thread. The first fastener extends through the through-bores and optionally, the second fastener to position the rough surfaces adjacent to each other and to pivotally couple and lock the fixation components in position. The threaded one of the first through-bore, the second through-bore and the second fastener is disposed farthest away from the head of the fastener.

In some embodiments, the rough surfaces define one of serration and radial interdigitation.

In some embodiments, the second fastener includes a threaded nut.

In some embodiments, the first and second pivot structures are located between the head and the nut, and the rough surfaces operably engage to each other in a locking state to provide anti-rotation to the fixation components.

In some embodiments, the first pivot structure includes a tubular structure having a first tube length, the second pivot structure including a tubular structure having a second tube length, and sum of the first and second tube lengths is in the range of about 1 cm-20 cm.

In some embodiments, each of the first component distal end portions and the second component proximal end portions includes a curved portion.

In some embodiments, at least one of the first fastener and the second fastener is dimensioned and configured to provide a secure grip surface.

In some embodiments, the external fixation components are one of unitary construction, unitary modular construction, modular construction and a combination thereof.

In some embodiments, the external fixator system is used on either side or across both sides of a bone or a joint.

In some embodiments, a surgical kit includes a an external fixation system including a first fixation component coupled to a first bone portion, the first fixation component including a first component proximal end portion and a first component distal end portion formed with a first pivot structure with a first through-bore along an axis of rotation and a first rough surface; a second fixation component coupled to a second bone portion, including a second component distal end portion and a second component proximal end portion formed with a second pivot structure with a second through-bore along an axis of rotation and a second rough surface; a first fastener, including a head and a shaft having an external thread; and optionally a second fastener. At least one of the first through-bore, the second through-bore and the second fastener includes an internal thread. The first fastener extends through the through-bores and optionally, the second fastener to position the rough surfaces adjacent to each other and to pivotally couple and lock the fixation components in position. The threaded one of the first through-bore, the second through-bore and the second fastener is disposed farthest away from the head of the fastener.

In some embodiments, a clamping device for an external fixation system includes: a clamp body, including an upper jaw and a lower jaw and a first groove for accommodating a first fixation element along a longitudinal axis of the groove and a slot in communication with the groove, and the upper and lower jaws each include a through-bore configured for receiving at least a portion of a locking assembly; a locking assembly extends through the through-bores and is configured to receive a second fixation element. The tightening of the locking assembly simultaneously clamps both the first and second fixation elements in a locking position.

In some embodiments, the locking assembly includes: a knob, including a clamp body facing end and a first opposing end, and first engagement feature, and a first bore formed therethrough bound by walls. At least a portion of the walls includes a taper structure, and the taper structure is larger toward the clamp body facing end than toward the first opposing end. The locking assembly also includes an elongated shaft including a stopper and one or more slits, and a second engagement feature, and a second bore formed longitudinally therethrough. The shaft is configured to extend through the through-bores of the upper and lower jaws and into the knob such that at least a portion of the stopper is positioned inside the clamp body and at least a portion of slit is disposed inside the knob. The shaft operatively interacts with the knob to compress the one or more slits.

In some embodiments, the through-bore of one of the upper and lower jaws, includes a first diameter and a second diameter, and the first diameter is smaller and disposed closer to the slot than the second diameter. The locking assembly includes: a knob, including a clamp body facing end and a first opposing end, and first engagement feature, and a first bore formed longitudinally therethrough; an elongated shaft includes a stopper formed with one or more slits, and a second engagement feature, and a second bore formed longitudinally therethrough. The shaft is configured to extend through the through-bores of the upper and lower jaws and into the knob such that at least a portion of the stopper is in contact with at least a portion of an internal surface containing the second diameter. The shaft operatively interacts with the knob to compress the stopper.

In some embodiments, at least one of the stopper and the internal surface is one of at least partially spherical, conical, frusto-conical, faceted and tapered.

In some embodiments, at least a portion of the second engagement feature of the shaft is disposed inside the knob in a locking state.

In some embodiments, at least one of the stopper and at least a portion of the shaft includes one of an at least partially spherical external surface, conical external surface, and a first anti-rotation feature and a combination thereof.

In some embodiments, one or more slits is disposed on the stopper.

In some embodiments, the first opposing end of the knob includes one or more slits.

In some embodiments, the stopper is disposed on one end of the shaft and at least one or more slits is disposed on an opposing end of the shaft.

In some embodiments, the slit end of the shaft is tapered.

In some embodiments, the through-bore of one of the upper and lower jaws includes a first diameter and a second diameter, and the first diameter is smaller and disposed closer to the slot than the second diameter. The shaft is configured to extend through the through-bores of the upper and lower jaws and into the knob such that at least a portion of the stopper is in contact with at least a portion of an internal surface containing the second diameter. The shaft operatively interacts with the knob to compress the stopper.

In some embodiments, at least one of the through-bores of the upper and lower jaws includes a second anti-rotation feature to operably interact with the first anti-rotation feature on the shaft.

In some embodiments, the first and second anti-rotation features are selected from a group consisting of protrusions, recesses, key ways, splines, and a combination thereof.

In some embodiments, the first and second engagement features are selected from a group consisting of threads, fins, tabs, slots and a combination thereof.

In some embodiments, the shaft is substantially threaded along its length.

In some embodiments, the clamp body facing end includes friction enhancing features.

In some embodiments, the friction enhancing features are selected from a group consisting of serration, interdigitation, splines, and a combination thereof.

In some embodiments, the knob defines a larger diameter toward the clamp body facing end than toward the first opposing end.

In some embodiments, the taper structure extends a substantial length of the knob.

In some embodiments, the clamp body further includes an annular protrusion for interfacing with the clamp body facing end of the knob.

In some embodiments, the annular protrusion is an insert.

In some embodiments, the annular protrusion includes a convex outer surface.

In some embodiments, the convex outer surface includes serration, radial interdigitation, or the like.

In some embodiments, the clamp body has a free end and a hinged end connecting the upper and lower jaws, and the groove is disposed adjacent to the free end.

In some embodiments, the outer edges of sides of the upper and lower jaws at the free end are chamfered.

In some embodiments, the clamp body has a free end and a hinged end, and the groove is disposed adjacent to the hinged end.

In some embodiments, the fixation elements are selected from a group consisting of pins, wires, rods and bars.

In some embodiments, at least a portion of an inner surface of the groove includes friction enhancing features.

In some embodiments, the clamp body is one of a unitary construction, unitary modular construction, and modular construction.

In some embodiments, the upper and lower jaws are coupled together via a spring-like structure disposed adjacent to the through-bores.

In some embodiments, the second fixation element is a bone pin.

In some embodiments, the clamp body further includes a second groove defining a diameter of one of same dimension and different dimension from a diameter of the first groove.

In some embodiments, the second groove defines a cross-sectional shape being one of same and different from a cross-sectional shape of the first groove.

In some embodiments, the clamping device includes an insert disposed between the upper and lower jaws for modifying the space therein.

In some embodiments, the insert includes a material different from a material of the clamp body.

In some embodiments, the insert includes an open end and a hinged end connecting an upper jaw of the insert to a lower jaw of the insert, and a groove for laterally receiving the first fixation element. The groove of the insert is disposed adjacent to the open end of the insert, and outer edges of sides of the groove of the insert are chamfered.

In some embodiments, the clamping device is disposable.

In some embodiments, an external fixator system includes a clamping device including a clamp body, including an upper jaw and a lower jaw and a first groove for accommodating a first fixation element along a longitudinal axis of the groove and a slot in communication with the groove. The upper and lower jaws each include a through-bore configured for receiving at least a portion of a locking assembly. The clamping device also includes a locking assembly extends through the through-bores and is configured to receive a second fixation element. The tightening of the locking assembly simultaneously clamps both the first and second fixation elements in a locking position.

In some embodiments, a bone fixator system for use adjacent to a joint area of the body includes: a proximal frame defining a first external fixation component coupled to a first bone portion, the first fixation component having a first length, a first component proximal end portion, and a first component distal end portion, and a distal frame coupled to the proximal frame, including an inferior frame portion and a posterior frame portion. The inferior frame portion and the posterior frame portion are operatively disposed in at least partially surrounding and spatial relation to a joint.

In some embodiments, a bone fixator system for use adjacent to a joint area of the body includes: a proximal frame defining a first external fixation component coupled to a first bone portion, the first fixation component having a first length, a first component proximal end portion, and a first component distal end portion, and a distal frame coupled to the proximal frame, including an inferior frame portion and a posterior frame portion. The posterior frame portion extends angularly from and above the inferior frame portion.

In some embodiments, the posterior frame portion extends angularly from and above the inferior frame portion.

In some embodiments, at least one of the inferior portion and the posterior portion includes a curvature.

In some embodiments, the distal frame defines a curvature extending from the inferior frame portion to the posterior frame portion.

In some embodiments, the proximal frame is pivotally and lockingly coupled to the distal frame.

In some embodiments, the proximal frame includes a second external fixation component.

In some embodiments, the second fixation component is one of an integral component of and a separate component from the distal frame.

In some embodiments, the distal frame includes one of a single curved elongated body structure and a multiple curved elongated body structure defining at least a first curved elongated body spaced apart and parallel to a second curved elongated body.

In some embodiments, the distal frame includes a first connector portion extending from the first curved elongated body to the second curved elongated body in the inferior portion and a second connector portion extending from the first curved elongated body to the second curved elongated body in the posterior portion.

In some embodiments, the distal frame includes a distal frame connector.

In some embodiments, the distal connector defines a length and includes a bore formed longitudinally and one or more mounting holes.

In some embodiments, the proximal frame includes a proximal frame connector for coupling with the distal frame connector.

In some embodiments, the proximal frame connector has a length and a bifurcated end portion and protrusions on an external surface for extending into the bore of the distal frame connector and operatively interacting with the one or more mounting holes for adjusting the at least partially surrounding and spatial relation to the joint.

In some embodiments, the proximal frame includes a second external fixation component coupled to a second bone portion, the second external fixation component having a second length, a second component proximal end portion and a second component distal end portion, and optionally, an outrigger.

In some embodiments, the first and second external fixation components and the proximal frame connector each includes a through-bore extending perpendicularly to the respective lengths and configured for receiving a locking device for pivotally coupling and locking the system.

In some embodiments, the locking device includes: a cylindrical main body, including a bore formed therethrough along a length of the main body and an external surface configured to operably interact with an internal surface of at least one of the through-bores of the first and second external fixation components and the proximal frame connector; and a knob including a main body facing end and an opposing end and a first engagement feature, and a bore formed therethrough bound by walls. At least a portion of the walls includes a taper structure that is larger toward the main body facing end than toward the opposing end. The locking device includes an elongated shaft including a stopper and one or more slits, and a second engagement feature, and a bore formed longitudinally therethrough. The shaft is configured to extend through the main body and into, and to operatively interact with, the knob to pivotally couple and lock the first and second external fixation components and the proximal frame connector, and to clamp a fixation element.

In some embodiments, the shaft is configured to extend through the main body and into the knob such that at least a portion of the stopper is positioned inside the main body and at least a portion of slit is disposed inside the knob in a locking state.

In some embodiments, the main body includes an internal taper structure.

In some embodiments, the shaft includes a partially spherical external surface.

In some embodiments, the locking device includes: a cylindrical main body, including a bore formed therethrough along a length of the main body, and an external surface configured to operably interact with an internal surface of at least one of the through-bores of the first and second external fixation components and the proximal frame connector. The locking device also includes a knob including a main body facing end and an opposing end, and a first engagement feature, and a bore formed longitudinally therethrough. The locking device also includes an elongated shaft includes a stopper formed with one or more slits, and a second engagement feature, and a bore formed longitudinally therethrough. The bore of the main body includes a first diameter and a second diameter, the first diameter is smaller than the second diameter. The shaft is configured to extend through the bore of the main body and into the knob such that at least a portion of the stopper is in contact with at least a portion of an internal surface containing the second diameter. The shaft operatively interacts with the knob to compress the stopper and to pivotally couple and lock the first and second external fixation components and the proximal frame connector, and to clamp a fixation element.

In some embodiments, the shaft includes one of a slit end and a tapered end.

In some embodiments, the first and second engagement features include threads.

In some embodiments, the bone fixator system includes a bone pin extending through the locking device and inserted into a calcaneous.

In some embodiments, the knob includes one or more slits on the opposing end.

In some embodiments, the first and second external fixation components and the proximal frame connector each include at least a rough external surface portion disposed adjacent to their respective the through-bores.

In some embodiments, at least one of the first and second external fixation components and the proximal and distal frame connectors and distal frame includes two or more segments joined together by one of permanent connection means and removable connection means.

In some embodiments, the bone fixator system includes a frame connector of one of unitary construction, unitary modular construction, and modular construction, has at least a portion of the frame connector is integrally formed with or permanently attached to at least a portion of one of the proximal frame and the distal frame.

In some embodiments, at least a portion of the distal frame is integrally formed with or permanently attached to at least a portion of the proximal frame.

In some embodiments, the joint is one of the ankle, the elbow, the knee, the wrist, the shoulder, and the hip.

In some embodiments, the bone fixator system is one of unitary construction, unitary modular construction, and modular construction.

In some embodiments the bone fixator system is disposable.

In some embodiments, a kit includes a bone fixator system for use adjacent to a joint area of the body. including: a proximal frame defining a first external fixation component coupled to a first bone portion, the first fixation component having a first length, a first component proximal end portion, and a first component distal end portion, and a distal frame coupled to the proximal frame, including an inferior frame portion and a posterior frame portion. The inferior frame portion and the posterior frame portion are operatively disposed in at least partially surrounding and spatial relation to a joint.

The principles, preferred embodiments and modes of operation of the present invention have been made apparent in the foregoing description.

Although the embodiments are numbered with, for example, "first," "second," or "third," or "fourth," the ordinal numbers do not imply priorities of the embodiments.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A clamping device for an external fixation system, comprising:
a clamp body including a first jaw and a second jaw, the first jaw and second jaw defining a slot extending between a first surface of the first jaw and a second surface of the second jaw and in communication with a first channel, the first channel configured to accommodate a first fixation element along a first longitudinal axis of the first channel, the first jaw defining a first opening and the second jaw defining a second opening that are sized to receive a portion of a locking assembly;
the locking assembly including a first fastening element configured to pass through the first opening and the second opening when a second longitudinal axis of the first fastening element is aligned with the first longitudinal axis, and defining a second channel configured to accommodate a bone pin for insertion into a bone of a subject,
the locking assembly including a second fastening element configured to engage with the first fastening element, wherein the locking assembly is configured to restrict movement of the first fixation element relative to the clamp body and restrict movement of the bone pin relative to the clamp body in response to tightening of the locking assembly;

wherein the second jaw further defines at least one recess of the second opening, and the first fastening element includes at least one protrusion, the at least one recess configured to:
- (1) receive the at least one protrusion when the at least one protrusion is aligned with the at least one recess and the second longitudinal axis is aligned with the first longitudinal axis to prevent rotation of the first fastening element relative to the second jaw, and
- (2) prevent the at least one protrusion from being received by the at least one recess when the at least one protrusion is not aligned with the at least one recess.

2. The clamping device of claim 1, wherein the first channel is defined by a first recess of the first surface, a second recess of the second surface, and a gap extending from a first edge of the first recess to a second edge of the second recess, the gap disposed on an opposite side of the first channel from the slot.

3. The clamping device of claim 1, wherein the first jaw further includes an annular protrusion defining a portion of the first opening, and the second fastening element includes a first engagement feature configured to lock angularly with the annular protrusion in response to tightening of the locking assembly.

4. The clamping device of claim 3, wherein the first engagement feature includes one of radial interdigitation or serration.

5. The clamping device of claim 1, wherein the first fastening element includes a threaded shaft configured to threadingly engage an inner surface of the second fastening element in response to tightening of the locking assembly.

6. The clamping device of claim 1, wherein the first fastening element defines a slit extending into the second channel, the slit configured to compress against the bone pin in response to tightening of the locking assembly.

7. The clamping device of claim 1, wherein the first jaw and the second jaw each include one of radial interdigitation or serration facing into the first channel to frictionally engage the first fixation element.

8. The clamping device of claim 1, wherein the first fastening element includes a first tapered shape configured to match a second tapered shape of the second fastening element such that an outer surface of the first fastening element is configured to contact along an inner surface of the second fastening element in response to tightening of the locking assembly.

9. The clamping device of claim 1, wherein the second opening includes a first diameter proximate to the slot and a second diameter distal from the slot, the second diameter greater than the first diameter, the first diameter configured to secure a stopper of the first fastening element in the second opening and prevent the stopper from passing through the second opening.

10. The clamping device of claim 1, wherein the first fastening element includes an elongated shaft defining the second channel and a ring structure having an outer surface defining an outer diameter that is greater than an outer diameter of the shaft, the at least one protrusion extending radially outward in a direction transverse to the second longitudinal axis from a portion of the outer surface.

11. The clamping device of claim 10, wherein the protrusion defines a planar end surface on an opposite side of the protrusion from the ring structure.

12. The clamping device of claim 1, wherein the second opening is sized such that a bottom surface of the first fastening element does not extend beyond a bottom surface of the second jaw when the at least one protrusion is completely received in the at least one recess.

13. A surgical kit, comprising:
a clamp body including a first jaw and a second jaw, the first and second jaw defining a slot extending between a first surface of the first jaw and a second surface of the second jaw and in communication with a first channel, the first channel configured to accommodate a first fixation element configured to support a clamp body along a first longitudinal axis of the first channel, the first jaw defining a first opening and the second jaw defining a second opening;

a first fastening element configured to pass through the first opening and the second opening when a second longitudinal axis of the first fastening element is aligned with the first longitudinal axis, and defining a second channel configured to accommodate a bone pin insertable into a bone connected to a joint of a subject; and a second fastening element configured to engage with the first fastening element, wherein the fastening elements are configured to restrict movement of the first fixation element relative to the clamp body and restrict movement of the bone pin relative to the clamp body in response to tightening of the second fastening element to the first fastening element;

wherein the second jaw further defines at least one recess of the second opening, and the first fastening element includes at least one protrusion the at least one recess configured to:
- (1) receive the at least one protrusion when the at least one protrusion is aligned with the at least one recess and the second longitudinal axis is aligned with the first longitudinal axis to prevent rotation of the first fastening element relative to the second jaw, and
- (2) prevent the at least one protrusion from being received by the at least one recess when the at least one protrusion is not aligned with the at least one recess.

14. The surgical kit of claim 13, wherein the first channel is defined by a first recess of the first surface, a second recess of the second surface, and a gap extending from a first edge of the first recess to a second edge of the second recess, the gap disposed on an opposite side of the first channel from the slot.

15. The surgical kit of claim 13, further comprising an annular protrusion configured to be coupled to a third surface of the first jaw opposite the first surface and to define a portion of the first opening, wherein the second fastening element includes a first engagement feature configured to lock angularly with the annular protrusion in response to tightening of the second fastening element to the first fastening element.

16. The surgical kit of claim 13, wherein the first fastening element includes a threaded shaft configured to threadingly engage an inner surface of the second fastening element in response to tightening of the second fastening element to the first fastening element.

17. The surgical kit of claim 13, wherein the first fastening element defines a slit extending into the second channel, the slit configured to compress against the bone pin in response to tightening of the locking assembly.

* * * * *